United States Patent [19]

Wehmeyer et al.

[11] Patent Number: 5,939,494
[45] Date of Patent: Aug. 17, 1999

[54] POLYMERIC SUBSTRATE CONTAINING MERCAPTO AND SULFONIC GROUPS

[75] Inventors: Richard M. Wehmeyer, Lake Jackson; Marlin E. Walters, West Columbia; Emmett L. Tasset, Lake Jackson, all of Tex.

[73] Assignee: The Dow Chemical Company, Midland, Mich.

[21] Appl. No.: 09/067,644

[22] Filed: Apr. 27, 1998

Related U.S. Application Data

[63] Continuation of application No. 08/468,863, Jun. 6, 1995, abandoned, which is a continuation of application No. 08/298,622, Aug. 31, 1994, Pat. No. 5,463,140.

[51] Int. Cl.⁶ .................................. C08F 8/36; C08F 12/08
[52] U.S. Cl. ............................. 525/333.5; 502/400
[58] Field of Search ................ 525/333.5, 332.2

[56] References Cited

U.S. PATENT DOCUMENTS

| | | |
|---|---|---|
| 2,468,982 | 5/1949 | Jansen . |
| 2,923,744 | 2/1960 | Scriabine et al. . |
| 3,029,221 | 4/1962 | Welch . |
| 3,172,916 | 3/1965 | Wagner . |
| 3,205,285 | 9/1965 | Turbak et al. . |
| 3,311,602 | 3/1967 | Raley, Jr. . |
| 3,321,536 | 5/1967 | Plesmid . |
| 3,366,711 | 1/1968 | Mazzolini et al. . |
| 3,394,089 | 7/1968 | McNutt et al. . |
| 3,426,104 | 2/1969 | Masson . |
| 3,546,165 | 12/1970 | Morgan . |
| 3,706,707 | 12/1972 | Trapasso . |
| 4,228,106 | 10/1980 | Martan ............................ 570/197 |
| 4,294,995 | 10/1981 | Faler et al. ....................... 568/728 |
| 4,369,293 | 1/1983 | Heydenreich et al. ........... 525/333.5 |
| 4,387,251 | 6/1983 | Meyer et al. ..................... 568/727 |
| 4,396,728 | 8/1983 | Faler et al. ....................... 521/32 |
| 4,423,252 | 12/1983 | Maki et al. ....................... 568/728 |
| 4,455,409 | 6/1984 | Faler et al. ....................... 525/351 |
| 4,467,122 | 8/1984 | Szabolcs .......................... 568/727 |
| 4,503,266 | 3/1985 | Szabolcs .......................... 568/719 |
| 4,568,724 | 2/1986 | Dean ................................ 525/203 |
| 4,587,304 | 5/1986 | Thaler et al. .................... 525/285 |
| 4,675,458 | 6/1987 | Riemann et al. ................. 568/727 |
| 4,725,420 | 2/1988 | Tachikawa et al. . |
| 4,764,557 | 8/1988 | Eichenauer et al. ............. 525/72 |
| 4,822,923 | 4/1989 | Li .................................... 568/724 |
| 4,825,010 | 4/1989 | Li .................................... 568/724 |
| 4,859,803 | 8/1989 | Shaw ............................... 568/727 |
| 4,912,170 | 3/1990 | Niwa et al. ...................... 525/337 |
| 4,931,594 | 6/1990 | Knebel et al. ................... 568/727 |
| 4,967,026 | 10/1990 | Daren ............................... 570/194 |
| 4,996,373 | 2/1991 | Bottenbruch et al. ............ 568/727 |
| 5,001,281 | 3/1991 | Li .................................... 568/727 |
| 5,105,026 | 4/1992 | Powell et al. .................... 568/727 |
| 5,124,490 | 6/1992 | Cipullo ............................ 568/758 |
| 5,210,328 | 5/1993 | Freitag et al. ................... 568/721 |
| 5,212,206 | 5/1993 | Randolph et al. ................ 521/32 |
| 5,248,838 | 9/1993 | Massirio et al. ................. 568/727 |
| 5,269,887 | 12/1993 | Jakob et al. ...................... 203/91 |
| 5,302,774 | 4/1994 | Berg et al. ........................ 568/727 |
| 5,463,140 | 10/1995 | Wehmeyer ........................ 568/727 |

FOREIGN PATENT DOCUMENTS

| | | |
|---|---|---|
| 1146870 | 4/1963 | Germany . |
| 2948222 | 7/1981 | Germany . |
| 172775 | 7/1965 | Russian Federation . |
| 1185223 | 3/1970 | United Kingdom . |

OTHER PUBLICATIONS

Abstract: *Chem. Abs.* 95:133593d (1981).
Abstract: *Chem. Abs.* 64:670h (1966).
Abstract: *Chem. Abs.* 59:11259e (1963).
Ellis et al., "The Preparation and Properties of a Double Series of Aliphatic Mercaptans," *J. Am. Chem. Soc.*, vol. 54 (1932), pp. 1674–1687.
Schramm et al., "The Synthesis of mercaptoalkanesulfonic Acids," *J. Am. Chem. Soc.*, vol. 77 (1955), pp. 6231–6233.
Frank et al., "The Preparation of Mercaptans from Alcohols," *J. Am. Chem. Soc.*, vol. 68 (1946), pp. 2103–2104.
*Chem. Abs.*, 90:86742m (1979) (Bruszewski).
R. Fischer, "Propanesultone," *Ind. Eng. Chem.*, vol. 56 (1964), pp. 41–45.
A. Mustafa, "The Chemistry of Sultones and Sultams," *Chemical Reviews*, vol. 54 (1954), pp. 195–223.
G. Manecke et al., *Chem. Abs.* 53:2083c (1959).
E. Goethals, "Synthesis and Polymerization of Allyl Vinyl Sulfonate," *Polymer Letters*, vol. 4 (1966), pp. 691–693.
E. Goethals et al., "Polymerization and Copolymerization of Allyl Allyl Sulfonate," *J. Macromol. Sci. —Chem.*, vol. A5 (1971), pp. 63–72.

(List continued on next page.)

*Primary Examiner*—Christopher Henderson

[57] ABSTRACT

A catalyst useful for the condensation of an aldehyde or ketone starting material with a phenol is an insoluble mercaptosulfonic acid compound. The heterogeneous catalysts comprise catalytically-active species represented by the formula:

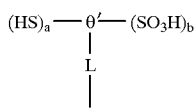

L is an optional linking group and — is a bond, which catalytically-active species is attached by the bond — to an insoluble organic or inorganic support;

or a catalytically-active species represented by the formula:

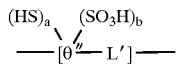

wherein L' is an optional linking group, — is a bond and θ' and θ" are residues of θ, and a and b are independently selected from integers equal to or greater than 1.

2 Claims, No Drawings

OTHER PUBLICATIONS

A. Warshawsky et al., "Functionalization of Polystyrene. I. Alkylation with Substituted Benzyl Halide and Benzyl Alcohol Compounds," *J. Org. Chem.*, vol. 43 (1978), pp. 3151–3157.

Akelah et al., "Application of Functionalized Polymers in Organic Synthesis," *Chem. Rev.*, vol. 81 (1981), pp. 557–587.

Fréchet et al., "Functionalization of Crosslinked Polystyrene Resins by Chemical Modification: A Review," in "Chemistry and Properties of Crosslinked Polymers" S. Labana, ed., Academic Press, New York (1977), pp. 59–83.

Maréchal, "Chemical Modification of Synthetic Polymers," in "Comprehensive Polymer Science," vol. 6, Allen, ed., Pergamon Press, New York, pp. 1–47.

M. B. Smith et al., "Lithium Aluminum Hydride–Aluminum Hydride Reduction of Sultones," *J. Org. Chem.*, vol. 46 (1981), pp. 101–106.

T. Durst et al., "Metallation of 5–and 6–membered ring sultones," *Can. J. Chem.*, vol. 47 (1969), pp. 1230–1233.

T. Durst et al., "A new route to 5–and 6–membered ring sultones," *Can. J. Chem*, vol. 48 (1970), pp. 845–851.

Tomoi et al., "A Novel One–pot Synthesis of Spacer–modified Polymer Supports and Phase–transfer Catalytic Activity of Phosphonium Salts Bound to the Polymer Supports," *Reactive Polymers*, vol. 3 (1985), pp. 341–349.

M. S. Chiles et al., "Phase Transfer Catalysts Anchored to Polystyrene," *Tetrahedron Letters* (1979), pp. 3367–3370.

M. Tomoi et al., "Novel Synthesis of Spacer–Modified Polymer Supports and Activity of Phase–Transfer Catalysts Derived from the Polymer Supports," *J. Polymer. Sci. Polymer Chem. Ed.*, vol. 20 (1982), pp. 3015–3019.

M. J. Farrall et al., "Bromination and Lithiation: Two Important Steps in the Functionalization of Polystyrene Resins," *J. Org. Chem.*, vol. 41 (1976), pp. 3877–3882.

S. P. McManus et al., "Reactions of Cyclic Halonium Ions and Alkylene Dihalides with Polystyryllithium. Preparation of Haloalkylated Polystyrene," *J. Org. Chem.*, vol. 45 (1980), pp. 2717–2719.

M. Haratake et. al. "Sorption of Phenols on Anion–Exchange Resins Having .omega.–Oxoalkyl or .omega.–Hydroxyalkyl Spacer," *Analytical Sciences*, vol. 4 (1988), pp. 591–594.

M. Gauthier et al., "Alkylated Styrene Ionomers with Variable Length Spacers. I. Synthesis," *J. Polymer Sci. : Part A: Polymer Chem.*, vol. 28 (1990), pp. 1549–1568.

P. Tundo, "Easy and Economical Synthesis of Widely Porous Resins; Very Efficient Supports for immobilized Phase–Transfer Catalysts," *Synthesis* (1978), pp. 315–316.

G. Zheng, et. al. "Synthesis of Bromoalkylated Crosslinked Polystyrene," *Xinan Shifan Daxue Xuebao, Ziran Kexueban*, vol. 2 (1986) pp. 68–70 *Chem. Abs.* 105:192049.

M. L. Hallensleben, "Preparation of Poly(p–(.omega.–lithiumalkyl)styrenes) and Their Use as Polymer Metalating Agents," *Angew. Makromol. Chem.*, vol. 31 (1973), pp. 147–159 *Chem. Abs.* 79:54020.

F. Döscher et al., "Synthesis of Sulfoalkylated Styrene–Divinylbenzene Copolymers," *Makromol. Chem., Rapid Commun.*, vol. 1 (1980), pp. 297–302.

E. De Witte et al., Telomerization Studies with Allyl Ethene Sulfonate and Allyl Allyl Sulfonate, *J. Makromol. Sci.–Chem.*, vol. A5 (1975), pp. 73–88.

Camps et al.; "Separation of a commercial mixture of isomers of chloromethylstyrene into its constituents, 3–chloro–methyl styrene and 4–chloromethylstyrene", 1982; *Fr. Makromol. Chem., Rapid Commun.*; 3(1), pp. 35–40.

Pham Quang Tho Lab Chim Org Macromol, Unites Enseign Rech Sci, Saint–Etienne, 42023.

Chemical Abstract 32290x (1970).

Selva et al., "Improved Selectivity in the Chloromethyllation of Alkylbenzenes in the Presence of Quaternary Ammonium Salts", *Synthesis*, pp. 1003–1004.

Shinkai et al., "Enhanced Reactivity and Affinity of Polymeric 3–Carbamoylpyridinium toward Cyanide Ion", *Polymer Letters Edition*, John Wiley and Sons, vol. 14, pp. 1–3, (1976).

POLYMERIC SUBSTRATE CONTAINING MERCAPTO AND SULFONIC GROUPS

CROSS-REFERENCE TO RELATED APPLICATION

This Application is a Continuation of application Ser. No. 08/468,863, filed Jun. 6, 1995, now abandoned, which is a continuation of Ser. No. 298,622, filed Aug. 31, 1994, now U.S. Pat. No. 5,463,140.

BACKGROUND OF THE INVENTION

This invention relates to preparation of polyphenols, more particularly to the preparation of polyphenols from ketones or aldehydes and phenols.

Acid-catalyzed condensation of phenols with aldehydes or ketones is well known. Acid catalysts include acidic ion exchange resin catalysts and soluble acid catalysts. Soluble acid catalysts can be, for example, hydrogen chloride, sulfuric acid, hydrochloric acid, phosphoric acid, hydrobromic acid, nitric acid, dimethyl sulfate, sulfur dioxide, 4-toluenesulfonic acid, boron trifluoride, alkanesulfonic acids, boron trifluoride complexes and other acid-acting compounds, including compounds which are hydrolyzed by water to form acids, e.g. aluminum chloride, sulfonyl chloride and phosgene.

A number of compounds are known to promote such an acid-catalyzed condensation. These promoters include mercaptan groups which are either free or bound to a resin. Alkyl mercaptans and bis-mercaptoethanolamine are examples of reported promoters.

It has been proposed by Scriabine et al. (U.S. Pat. No. 2,923,744) to produce Bisphenol A using sulfuric acid, promoted by mercaptoalkanesulfonic acids or salts or corresponding sulfonate esters at a level of 0.1–5% by weight of the base charge, to catalyze condensation of acetone and phenols, when used in amounts of 0.1 to 5 percent by weight based on total charge. Sulfuric acid is used in amounts of about 2 moles per mole of acetone.

Riemann et al. (U.S. Pat. No. 4,675,458) have proposed making 9,9-bis-(4-hydroxyphenyl)fluorene in the presence of sulfuric acid, preferably concentrated sulfuric acid, and a mercaptan, particularly 3-mercaptopropionic acid, as promoter.

Massirio et al. (U.S. Pat. No. 5,248,838) have disclosed the use of a combination of methanesulfonic acid and a mercaptan/mercaptoalkanoic acid for catalyzing the condensation of phenols with fluorenone. High levels of methanesulfonic acid with respect to the feed and the mercaptan/ mercaptoalkanoic acid, are used. The reactions can be run in halogenated hydrocarbon solvents.

Bottenbruch et al. (U.S. Pat. No. 4,996,373) have proposed a process for producing dihydroxyaryl compounds from carbonyl compounds and phenols under high pressure, in the presence of various catalysts, including sulfonic acid resins. Catalysts containing sulfhydryl functionality, e.g. ion exchangers treated with mercapto compounds, have been disclosed for this use.

Meyer et al. (U.S. Pat. No. 4,387,251) have proposed processes for making 4,4'-dihydroxydiphenyl alkanes using aromatic sulfonic acids as condensing agents. Mercapto groups are included within the definition of $R_3$ and are characterized as being inert. Freitag et al. (U.S. Pat. No. 5,210,328) disclose using the same types of sulfonic acid catalysts for making cycloalkylidene bisphenols.

Jansen (U.S. Pat. No. 2,468,982) has proposed preparation of bisphenols using anhydrous hydrogen chloride in combination with a mercaptoalkanoic acid, which may be formed in situ by reaction of a mercaptol with the ketone, as condensing agent.

Knebel et al. (U.S. Pat. No. 4,931,594) disclose the use of large amounts of sulfonic acid resin, mixed with uncombined 3-mercaptopropionic acid, to cause the condensation to occur.

It has been proposed in British Patent 1,185,223 to use a mixture of insoluble resins, one a sulfonic acid resin and the other a resin containing mercapto groups, for making bisphenols.

Randolph et al. (U.S. Pat. No. 5,212,206) disclose a catalyst, made by treating a sulfonated ion-exchange resin with a dialkylaminomercaptan. Other references, representative of references on modification of sulfonic acid ion-exchange resins, include Wagner (U.S. Pat. No. 3,172,916). McNutt et al. (U.S. Pat. No. 3,394,089), Faler et al. (U.S. Pat. Nos. 4,455,409; 4,294,995 and 4,396,728); Heydenrich et al. (U.S. Pat. No. 4,369,293); Berg et al. (U.S. Pat. No. 5,302,774) and Maki et al. (U.S. Pat. No. 4,423,252). The reactive catalysts generally include mercapto-functions attached to a sulfonic acid group in the form of a sulfonamido or ammonium sulfonate salt.

Shaw (U.S. Pat. No. 4,859,803) discloses preparing bisphenols from phenol and a ketone in the presence of an acidic (sulfonic acid) ion-exchange resin and a mercaptan, the mercaptan being added at particular locations of a specified reactor configuration to prevent the formation of cyclic diners.

Li has disclosed (U.S. Pat. No. 4,825,010) isomerization of by-products of condensates of phenols and ketones, using a catalytic amount of acidic sulfonated cationic-exchange resin having sulfonic acid sites ionically bonded to alkylmercaptoamines. Other patents by Li (U.S. Pat. Nos. 4,822, 923 and 5,001,281) further suggest the state of the art of using ion-exchange resins to isomerize by-products of bisphenol syntheses.

Powell et al. (U.S. Pat. No. 5,105,026) disclose using acidic ion-exchange resins to isomerize undesirable products of bisphenol synthesis to desirable products, e.g. to Bisphenol A. Morgan (U.S. Pat. No. 3,546,165) has disclosed condensation of phenol with various ketones, including fluorenone and indanone, using high levels of hydrochloric acid or hydrogen chloride, in the presence of minor amounts of 3-mercapto-propionic acid. The products are used for the preparation of polyester resins.

Szabolcs (U.S. Pat. Nos. 4,467,122 and 4,503,266) discloses washing crude product, containing BHPF, from a hydrochloric acid/zinc chloride catalyzed process, to remove HCl, $ZnCl_2$ and excess phenol, prior to recrystallization from dichloroethane. See also the abstract for DE OLS 2,948,222 (Jul. 30, 1981).

Korshak et al. (SU 172,775) disclose washing a mixture of phenol, BHPF and HCl with water, after which phenol is removed by distillation.

The following references, herein incorporated by reference, disclose the preparation of resins, containing sulfonic acid functionality, introduced either by copolymerization or by sulfonation after polymerization:

| | |
|---|---|
| U.S. Pat. No. 3,205,285 | Turbak et al. |
| U.S. Pat. No. 3,366,711 | Mazzolini et al. |
| U.S. Pat. No. 3,426,104 | Masson |
| U.S. Pat. No. 4,587,304 | Thaler et al. |
| U.S. Pat. No. 4,764,557 | Eichenauer et al. |

Trapasso (U.S. Pat. No. 3,706,707) discloses the preparation of adducts from a polymerized cyclic ether and a sultone. Dean (U.S. Pat. No. 4,568,724) is of similar interest with respect to reaction products from an EPDM rubber and a sultone.

Welch (U.S. Pat. No. 3,029,221) and Niwa et al. (U.S. Pat. No. 4,912,170) disclose processes for modifying polystyrene resins.

It is an object of this invention to provide a process for the condensation of aldehydes or ketones with phenols, to achieve high yields of preferred bis-(4-hydroxyaryl) isomers with low reaction times while avoiding use of strong inorganic acids.

Further objects of the invention include the development of processes for the synthesis of polyphenols, characterized by high yields of high purity products under reaction conditions, which are not corrosive to vessels in which the processes are conducted. In addition, avoiding the use of sulfuric acid, eliminates the possibility of side reactions, including sulfonation of phenols.

DISCLOSURE OF THE INVENTION

In one aspect, this invention relates to a process for the condensation of an aldehyde or ketone starting material with a phenol, unsubstituted in at least one position, comprising reacting the aldehyde or ketone starting material with the phenol in a reaction mixture in the presence of a soluble or insoluble mercaptosulfonic acid compound under conditions sufficient to bring about formation of a geminal bisphenolic moiety at each aldehyde or ketone moiety in the starting material;

provided that the soluble mercaptosulfonic acid compound is characterized by the formula

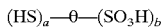

wherein θ is an alkylene, cycloaliphatic, arylene, alkylenearylene, alkylenecycloaliphatic, alkylenearyl, heterocyclic or alkyleneheterocyclic residue and a and b are independently selected from integers from 1 to about 20; and the insoluble mercaptosulfonic acid comprises a catalytically-active species represented by the formula

in which θ' is an alkylene, cycloaliphatic, arylene, alkylenearylene, alkylenecycloaliphatic, alkylenearyl, heterocyclic or alkyleneheterocyclic residue; a and b are independently selected from integers from 1 to about 20; L is an optional linking group and — is a bond, which catalytically-active species is attached by the bond — to an insoluble organic or inorganic support;

or a catalytically-active species represented by the unit formula

wherein θ" is an alkylene, arylene, cycloaliphatic, alkylenearylene, alkylenecycloaliphatic, alkylenearyl, heterocyclic or alkyleneheterocyclic residue; a and b are independently selected from integers from 1 to about 20; L' is an optional linking group and — is a bond.

This invention further relates to novel catalytically-active polystyrene resins, characterized by bearing at least one of each of a mercapto function and a sulfonic acid function on some individual styrene units of a polymer chain.

In yet another aspect, this invention relates to processes for preparing the catalytically-active polystyrene resins. These processes preferably comprise steps of (b) sulfonating a haloalkylpolystyrene to produce an intermediate having sulfo functional groups; (c) optionally converting the sulfo functional groups to corresponding alkali metal salts; (d) thiolating the thus-produced sulfostyrene intermediate by reacting the halo function with a reactive thiolate to produce a corresponding mercapto group or precursor thereof; (e) optionally hydrolyzing the thus-thiolated intermediate with an acid or base when the thiolated group so requires and (f) optionally acidifying (if so required) to produce sulfonic acid functional groups units.

The process of the invention permits use of very low levels of a single acidic condensing agent. The process permits simplified product isolation procedures, recycle procedures, and/or waste management. The process does not require a neutralization step to remove hydrochloric or sulfuric acid and does not produce a waste salt stream. The acidic condensing agents used in the process of this invention are readily removed from the reaction mixtures and can be recovered and recycled.

The process of this invention results in high selectivity toward preferred bis-(4-hydroxyaryl) isomers and very fast reaction rates.

The process of this invention is particularly useful for the preparation of bis(hydroxyaryl) compounds, such as bisphenol A and 9,9-bis-(4-hydroxyphenyl)fluorene, both of which are useful in the preparation of polycarbonates and other commercially significant polymers.

The heterogeneous catalysts disclosed herein advantageously are more reactive than heterogeneous catalysts currently used. They advantageously allow using lower temperatures with correspondingly greater selectivity for desired product than is currently experienced. Greater selectivity reduces purification necessary to produce a desired or preselected purity of product. Thus for a commercially produced bisphenol like Bisphenol A, a heterogeneous catalyst disclosed herein can be advantageously substituted in an existing commercial process, run with the same or higher throughput at a lower temperature with less purification to achieve at least equally pure product.

DETAILED DESCRIPTION OF THE INVENTION

Ketones or aldehydes and phenolic compounds (hereinafter phenol, phenols, a phenol or phenolic starting material) useful in process of the invention are known in the art and are described in the literature, for instance Jansen '982, supra, Maki et al., '252, supra, Morgan '165, supra, and Knebel et al. '594, supra, all of which are herein incorporated by reference.

The condensations of this invention can be represented by the equation for a representative condensation, that of phenol with 9-fluorenone:

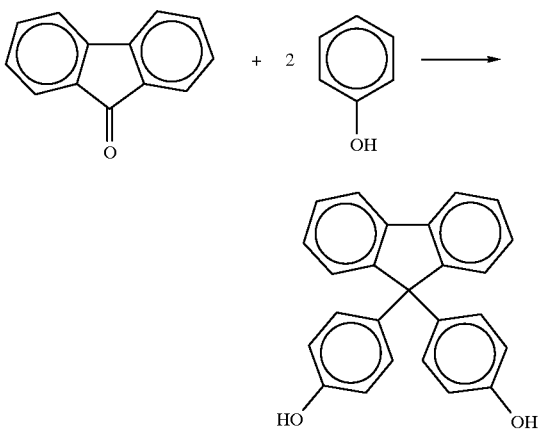

The process for making bisphenol A can be represented by the equation:

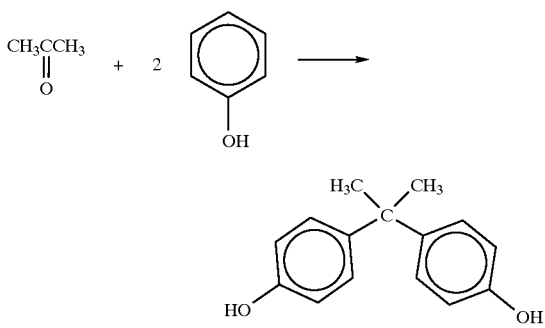

Phenol starting materials are advantageously any aromatic hydroxy compounds which have at least one unsubstituted position, and optionally have one or more inert substituents such as hydrocarbyl or halogen at the one or more ring positions. An inert substituent is a substituent which does not interfere undesirably with the condensation of the phenol and ketone or aldehyde and which is not, itself, catalytic. Preferably, the phenols are unsubstituted in the position, para to the hydroxyl group.

Alkylene (alk), alkyl, cycloaliphatic, aryl, arylene (ar), alkylarylene (alkar), arylalkylene (aralk), alkylcycloaliphatic and alkylenecycloaliphatic are hydrocarbyl functions, that is, functions containing carbon and hydrogen atoms. The alkylene functions can be straight or branched chain and saturated or unsaturated, that is alkylene, alkenylene, or alkynylene. Cycloaliphatic hydrocarbon residues include both saturated and unsaturated cyclic residues, that is, cycloalkylene and cycloalkenylene. Arylene includes mono- and polycyclic aromatic residues, e.g. those of benzene, biphenyl, biaryl, naphthyl, phenanthrenyl, anthracenyl or aryl groups, including those bridged by an alkylene group. Alkaryl residues include alkyl, alkenyl and alkynyl-substituted aromatic rings. Aralkyl includes alkyl, alkenyl or alkynyl residues, substituted by one or more aromatic groups.

Alkyl groups include both straight- and branched-chain isomers of methyl, ethyl, propyl, butyl, pentyl, hexyl, heptyl, octyl, nonyl, decyl, undecyl, dodecyl, tridecyl, tetradecyl, pentadecyl, hexadecyl, heptadecyl, nonadecyl and eicosyl groups, as well as the corresponding unsaturated (alkenyl or alkynyl) groups, as well as higher homologues. Preferably, the alkyl groups are of 1–20 carbon atoms, more preferably of 1–5 carbon atoms, most preferably those of 1–3 carbon atoms. Alkyl of 1–5 carbon atoms includes the various methyl, ethyl, propyl, butyl and pentyl isomers.

Alkyl, aryl, alkaryl and aralkyl substituents are suitable hydrocarbyl substituents on the phenol reactant.

Other inert substituents on the phenols include, but are not limited to alkoxy, aryloxy or alkaryloxy, wherein alkoxy includes methoxy, ethoxy, propyloxy, butoxy, pentoxy, hexoxy, heptoxy, octyloxy, nonyloxy, decyloxy and polyoxyethylene, as well as higher homologues; aryloxy, phenoxy, biphenoxy, naphthyloxy, etc. and alkaryloxy includes alkyl, alkenyl and alkylnyl-substituted phenolics.

Additional inert substituents on phenols include halo, such as bromo, chloro or iodo.

Cyano and nitro substituents may deactivate the phenols and aldehyde and carboxylic acid substituents may cause interfering reactions. Additional hydroxyl substituents may be suitable in some cases.

Preferred substituents include alkyl moieties containing from 1 to about 10 carbon atoms, more preferably, lower alkyl moieties, containing from 1 to about 5 carbon atoms, most preferably from 1 to 3 carbon atoms. The alkyl substituents may be straight or branched chain isomers.

Exemplary phenols include, but are not limited to, phenol, 2-cresol, 3-cresol, 4-cresol, 2-chlorophenol, 3-chlorophenol, 4-chlorophenol, 2-tert-butylphenol, 2,4-dimethylphenol, 2-ethyl-6-methylphenol, 2-bromophenol, 2-fluorophenol, 2-phenoxyphenol, 3-methoxyphenol, 2,3,6-trimethylphenol, 2,3,5,6-tetramethylphenol, 2,6-xylenol, 2,6-dichlorophenol, 3,5-diethylphenol, 2-benzylphenol, 2,6-di-tertbutylphenol, 2-phenylphenol, 1-naphthol, 2-naphthol and the like. Preferred phenols include phenol, 2- or 3-cresol, 2,6-dimethylphenol, resorcinol, naphthols, and mixtures thereof. Most preferably, the phenol is unsubstituted.

The ketones which are advantageously used include any ketone having a single ketone carbonyl (C=O) group or several ketone carbonyl groups, and which are reactive under the conditions used. The ketones can be substituted with substituents, which are inert under the conditions used. Inert substituents are as set forth above for the reactive phenols.

The ketones are advantageously selected from aliphatic, aromatic, alicyclic or mixed aromatic-aliphatic ketones, diketones or polyketones, of which acetone, methyl ethyl ketone, diethyl ketone, benzil, acetylacetone, methyl isopropyl ketone, methyl isobutyl ketone, acetophenone, ethyl phenyl ketone, cyclohexanone, cyclopentanone, benzophenone, fluorenone, indanone, 3,3,5-trimethylcyclohexanone, anthraquinone, 4-hydroxyacetophenone, acenaphthenequinone, quinone, benzoylacetone and diacetyl are representative examples.

Ketones having halo, nitrile or nitro substituents can also be used, for example, 1,3-dichloroacetone or hexafluoroacetone.

Aliphatic ketones which are useful starting materials include, but are not limited to acetone, ethyl methyl ketone, isobutyl methyl ketone, 1,3-dichloroacetone, hexafluoroacetone and the like. A preferred aliphatic ketone is acetone, which condenses with phenol to produce 2,2-bis-(4-hydroxyphenyl)-propane, commonly known as bisphenol A. Another preferred aliphatic ketone is hexafluoroacetone, which reacts with two moles of phenol to produce 2,2-bis-(4-hydroxyphenyl)-hexafluoropropane (bisphenol AF).

A preferred class of ketones has at least one hydrocarbyl group containing an aryl group, for example, a phenyl, tolyl, naphthyl, xylyl or 4-hydroxyphenyl group.

Other preferred ketones include those in which the hydrocarbon radicals connected to the carbonyl groups of the ketone is in a cycloaliphatic group. Examples of specific preferred ketones include 9-fluorenone, cyclohexanone, 3,3,5-trimethylcyclohexanone, indanone, indenone, anthraquinone and the like.

Most preferred ketones include 9-fluorenone, benzophenone, acetone, acetophenone, 4-hydroxyacetophenone and 4,4'-dihydroxybenzophenone. Most preferably, the process of this invention is used to make bisphenol A by reaction of phenol with acetone or to make 9,9-bis-(4-hydroxyphenyl)fluorene (BHPF) by reaction of phenol with 9-fluorenone.

The process of this invention can also be used for the condensation of phenols with aldehydes, for example, with formaldehyde, acetaldehyde, propionaldehyde, butyraldehyde or higher homologues of the formula RCHO, wherein R is alkyl of 1–20 carbon atoms. The condensation of two moles of phenol with one mole of formaldehyde produces bis-(4-hydroxyphenyl)methane, also known as Bisphenol F.

It will be understood that dialdehydes and ketoaldehydes, for example, glyoxal, phenylglyoxal or pyruvic aldehyde, can also be used.

The products are generally geminal bisphenols, that is, compounds having one or more single carbon atoms to which are attached nuclei of two phenolic moieties. This single carbon atom corresponds to the carbonyl carbon of the ketone or aldehyde reactant. In the case of starting materials, containing more than one aldehyde or ketone carbonyl, the product will contain more than one geminal bisphenolic moiety. For example, the condensate from acetyl acetone and phenol is 2,2,4,4-tetrakis-(hydroxyphenyl) pentane and the condensate from benzoylacetone is 2,2,4,4-tetrakis-(hydroxyphenyl)-4-phenylbutane.

The mercaptosulfonic acid catalyst is any species, whether soluble or insoluble in the reaction mixture, containing at least one thiol (SH) group and at least one sulfonic acid ($SO_3H$) group, including any group which can be converted to a sulfonic acid group under the reaction conditions used.

In the specification and claims, the soluble mercaptosulfonic acid moiety is represented by the formula

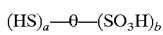

$(HS)_a$—θ—$(SO_3H)_b$ wherein θ is an alkylene, cycloaliphatic, arylene, alkylenearylene, alkylenecycloaliphatic, alkylenearyl, heterocyclic or alkyleneheterocyclic residue and each of a and b is independently an integer from 1 to about 20.

"Soluble mercaptosulfonic acid," as used in the specification and claims, means a compound which has some solubility in the reaction mixture and which can be removed from the mixture, at the end of the reaction, by extraction, ion-exchange, precipitation, absorption, etc.

"Insoluble mercaptosulfonic acid," as used in the specification and claims, means a material, which is insoluble in the reaction mixture. These materials are generally polymeric organic resins, or catalytically-active compounds, bonded to an inorganic support.

When θ is alkylene, the alkylene can be of 2 to up to about 20 carbon atoms, including straight and branched chain alkylene moieties, corresponding heterochain moieties and alkylene substituted with inert substituents. Inert substituents include, for example, alkoxy, alkenyl, alkynyl, halo, nitro, aryl, etc.

Representative mercaptoalkanesulfonic acids include, but are not limited to, 2-mercaptoethanesulfonic acid, 3-mercaptopropanesulfonic acid, 4-mercaptobutanesulfonic acid, 4-mercaptopentanesulfonic acid, 3-mercapto-2,2-dimethylpropanesulfonic acid, 2,3-dimercaptopropanesulfonic acid, mercaptopropane-2,3-disulfonic acid, 2-benzyl-4-mercaptobutanesulfonic acid, 5-mercaptopentanesulfonic acid or the like. Most preferred among this group of catalysts are 3-mercaptopropanesulfonic acid and 4-mercaptobutanesulfonic acids.

The types of mercaptoalkanesulfonic acids which are useable are exemplified by the following compounds of Formula I:

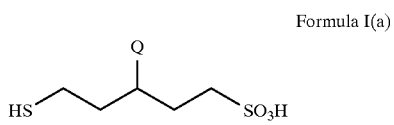

Formula I(a)

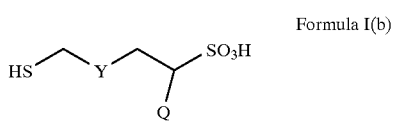

Formula I(b)

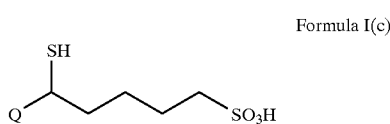

Formula I(c)

wherein Q is an inert substituent and Y is an optional hetero element, e.g. O, N—Q or S. Q is H, hydrocarbyl, halo, carboxy, sulfonyl, etc., as described above for inert substituents on the phenol, ketone or aldehyde starting materials. More than one Q may optionally be present. The Q substituent can be at any position on the chain and more than one Q can be present. As set forth in the general formula for the soluble catalysts, more than one SH or sulfonic acid function are optionally present in the catalyst.

Compounds of Formula I(a) are included within the generic formula

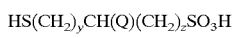

$HS(CH_2)_y CH(Q)(CH_2)_z SO_3H$ wherein y is an integer from 0 to about 20, z is an integer from 0 to about 20, Q is an optional inert substituent and y+z≧1, up to a maximum of about 40.

Compounds of Formula I(b) are included within the generic formula

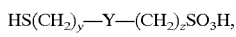

$HS(CH_2)_y$—Y—$(CH_2)_z SO_3H$, wherein one or more inert substituents, Q, can be attached at any point along the carbon chain; wherein Y is a heteroelement, e.g. —S—; each of y and z is at least 1 and y+z≧2, up to a maximum of about 40. Preferred linear mercaptoalkanesulfonic acids are those in which the distance between the mercapto and sulfonic acid functions are less than about 20 atoms, including both carbon and heteroatoms. Compounds of Formula I(b) can also have more than one SH and/or more than one sulfonic acid function.

Compounds of Formula I(c) are included within the formula

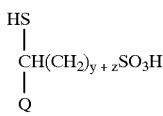

wherein y and z are as above.

Mercaptosulfonic acid precursors can also be used as catalysts, by conversion to active mercaptosulfonic acid catalysts in the reaction mixtures. For example, a precursor alkali metal sulfonate salt can be neutralized with a mineral acid to produce a free sulfonic acid. Sulfonate ester precursors can be hydrolyzed by treatment with a strong base, e.g. sodium or potassium hydroxide, and thus converted to a corresponding alkali metal salt. A further precursor of sulfonic acids for the practice of this invention, is a sulfonyl halide group, which can readily converted to a corresponding sulfonic acid.

Mercaptosulfonic acids can be prepared from corresponding haloalkanesulfonic acids by reaction with an alkali metal mercaptide, for example, $$X\text{-alk-}SO_3H + NaSH \rightarrow HS\text{-alk-}SO_3H + NaX$$

wherein X is Cl, Br or I and alk is alkylene, generally in accordance with Ellis et al., "The Preparation and Properties of a Double Series of Aliphatic Mercaptans," *J. Am. Chem. Soc.*, vol. 54 (1932), pages 1674–1687.

Alternatively, treatment of a haloalkanesulfonic acid with an alkali metal thioacetate, followed by hydrolysis, can be used to prepare mercaptoalkanesulfonic acids.

Another route to mercaptosulfonic acids is by converting halides to a corresponding thiouronium salt, which is hydrolyzed with a strong base, as follows:

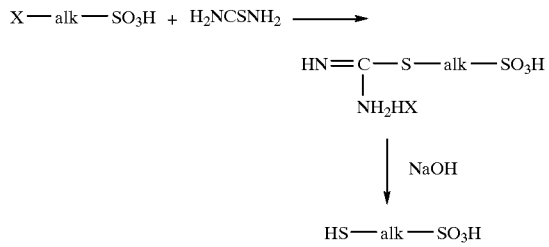

generally according to Schramm et al., "The Synthesis of mercaptoalkanesulfonic Acids," *J. Am. Chem. Soc.*, vol. 77 (1955), pages 6231–6233.

Hydroxyalkanesulfonic acids can also be converted to the corresponding mercaptoalkanesulfonic acid by reaction with thiourea and HBr/HCl to produce a thiouronium salt, which is hydrolyzed using a strong base. See, Frank et al., "The Preparation of Mercaptans from Alcohols," *J. Am. Chem. Soc.*, vol. 67 (1946), pages 2103–2104.

Higher mercaptoalkanesulfonic acids can be prepared from higher olefinsulfonic acids, e.g. oleylsulfonic acid, by adding hydrogen sulfide across the olefinic bond. Alternatively, the olefinic bond of an olefinic sulfonic acid can be halogenated, e.g. chlorinated, and the halogen moiety replaced by a mercapto function, as above.

Mercaptoalkanesulfonic acids can also be made from corresponding sultones, e.g., 1,4-butanesultone, in accordance with *Chem. Abs.*, 90:86742m (1979); R. Fischer, "Propanesultone," *Ind. Eng. Chem.*, vol. 56 (1964), pages 41–45; or A. Mustafa, "The Chemistry of Sultones and Sultams," *Chemical Reviews*, vol. 54 (1954), pages 195–223.

When —θ— is arylene, the sulfonic acid and mercapto moieties are attached directly to an aromatic ring. Representative aromatic mercaptosulfonic acids include 2-mercaptobenzenesulfonic acid, 3-mercaptobenzenesulfonic acid, 4-mercaptobenzenesulfonic acid, 2-mercaptonaphthalenesulfonic acid or the like. The aromatic residues can be substituted with substituents, e.g., H, alkyl, alkenyl, alkynyl, aryl, halo, alkoxy, aryloxy (Q, above), which are inert under the reaction conditions. The active catalysts can contain more than one SH and/or more than one sulfonic acid function in each molecule.

Cycloaliphatic residues include those of cyclohexane, cyclopentane and cycloheptane; the aliphatic ring of indane, tetralin or benzocycloheptane, and the like. Representative cycloaliphatic mercaptosulfonic acids include, but are not limited to, 2-mercaptocyclohexanesulfonic acid, 2-mercaptocyclopentanesulfonic acid, 3-mercaptocyclohexanesulfonic acid, 3-mercaptocyclopentanesulfonic acid and the like. The cycloaliphatic rings can also be substituted with inert substituents and can contain more than one SH group and/or more than one sulfonic acid group.

Representative alkylenecycloaliphatic mercaptosulfonic acid compounds can be represented by the following formulas:

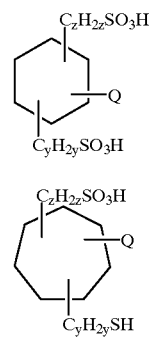

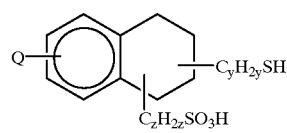

wherein y and z are integers of 0 to about 20; Q is an optional inert substituent selected from alkyl, aryl, halo, alkoxy or aryloxy and $y+z \geq 1$. Typical compounds include (mercaptomethyl)cyclohexanesulfonic acid and (mercaptomethyl)(sulfomethyl)cyclohexane.

Typical alkylenearyl mercaptosulfonic acids can be represented by the formulas:

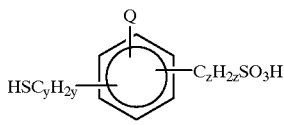

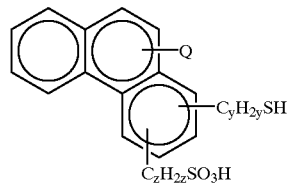

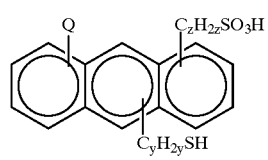

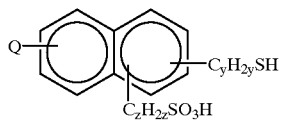

wherein x, y and Q are as above and $x+y \geq 1$.

A typical compound of this group, (mercaptomethyl)benzene-sulfonic acid, can be prepared from a corresponding chloromethyl- or bromo-methylbenzenesulfonic acid.

Oligomers from vinylsulfonic acid can provide soluble materials, containing large numbers of mercapto and sulfonic acid groups. This type of soluble catalyst can be prepared from oligomers containing vinylsulfonic acid units, half of which can be converted to chlorosulfonyl units and reduced to mercapto units in accordance with the following reaction scheme:

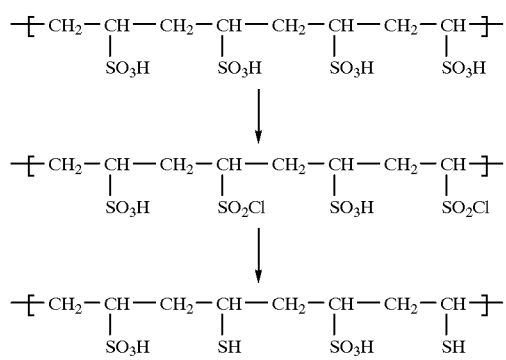

Another type of oligomeric catalysts, containing a multiplicity of mercapto and sulfonic acid units, can be prepared from propenesultone. Propenesultone is prepared as described by G. Manecke et al., *Chem. Abs.* 53:2083c (1959), Helberger et al., DE 1,146,870 and *Chem. Abs.* 59:11259 (1963). The sultone ring of the polymer can be opened, generally as above, to furnish mercaptosulfonic acid oligomers, containing a plurality of mercapto and sulfonic acid units.

In addition, oligomers containing a plurality of mercaptosulfonic acid functions can be prepared from oligomers of 4-allyl-1,4-butanesultone. The monomer is prepared as described for 4-benzyl-1,4-butanesultone, using allyl chloride instead of benzyl chloride. 4,4-Diallyl-1,4-butanesultone can be prepared by addition of a second allyl group.

Other catalytically active mercaptosulfonic acid oligomers can be prepared from allyl vinylsulfonate ($CH=CHSO_2OCH_2CH=CH_2$), which is polymerized to form a corresponding sultone-containing polymer in accordance with E. Goethals, "Synthesis and Polymerization of Allyl Vinyl Sulfonate," *Polymer Letters*, vol. 4 (1966), pages 691–693. The resulting polymer, containing sultone groups is treated with a reactive thiolate to open the sultone rings and produce mercaptoalkyl sulfonate polymers.

The conversions can be represented by the equation:

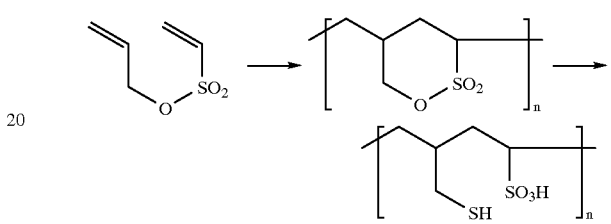

Similar catalytically-active solid oligomers can be prepared from oligomers of allyl allylsulfonate ($CH_2=CHCH_2SO_2OCH_2CH=CH_2$), which can be polymerized in accordance with E. Goethals et al., "Polymerization and Copolymerization of Allyl Allyl Sulfonate," *J. Macromol. Sci.-Chem.*, vol. A5 (1971), pages 63–72. The oligomers are converted to mercaptosulfonic acid functional materials by a corresponding ring opening reaction.

The conversion can be represented by the equation:

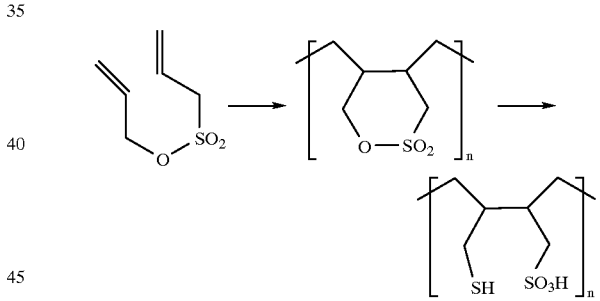

Heterocyclic residues advantageously include cyclic residues, containing N, O, or S. These will generally correspond to aromatic compounds, for example, residues from pyridine, thiophene, quinoline, phenanthridine, and the like, as well the corresponding partially or fully hydrogenated compounds. Alkyleneheterocyclic residues otherwise correspond to aromatic residues of the same configuration, as do alkyl heterocyclic residues, as well as corresponding fully or partially hydrogenated compounds.

Preferred soluble mercaptosulfonic acids are compounds in which the mercaptan and sulfonic acid functions are separated by a chain of about 2 to about 10 atoms, whether the chain or linker arm is in an alkylene group or incorporated in an aromatic, cycloaliphatic or heterocyclic ring, whether or not the chain includes heteroelements, and whether or not the mercapto and sulfonic acid functions are attached directly or indirectly to the ring structures. Preferred soluble catalysts for the practice of this invention are mercaptosulfonic acids in which a and b are independently 1 from to about 4. More preferably, a and b are independently 1 or 2. Most preferred are mercaptosulfonic acids, containing mercapto and sulfonic acid functions in a 1:1 molar ratio, that is a and b are each 1, more particularly 3-mercaptopropanesulfonic acid and 4-mercaptobutanesulfonic acid.

When the mercaptosulfonic acid is insoluble, the heterogeneous catalyst comprises a catalytically-active species represented by Formula II:

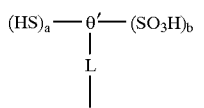

Formula II in which each of a and b is independently an integer from 1 to about 20, θ' is an alkylene, cycloaliphatic, arylene, alkylenearylene, alkylenecycloaliphatic, alkylenearyl, heterocyclic or alkyleneheterocyclic residue, L is an optional linking group and — is a bond, which catalytically-active species is attached by the bond — to an insoluble organic or inorganic support;

or a catalytically-active species represented by Formula III:

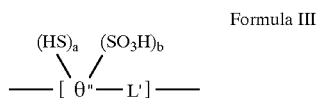

Formula III wherein θ" is an alkylene, arylene, cycloaliphatic, lkylenearylene, alkylenecycloaliphatic, alkylenearyl, eterocyclic or alkyleneheterocyclic residue; a and b are independently selected from integers from 1 to about 20; L' is an optional linking group and — is a bond.

Catalytically-active materials of Formula II are generally derived from polymers of ethylenic monomers, wherein the insoluble organic support is the main chain of a resulting polymer and —L— is a covalent bond or a linking group. This type of polymer will include unit structures represented by the general formula

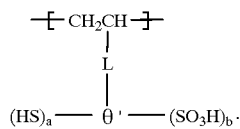

Preferably, the catalytically-active materials will include those having from 1 to about 4 of each of mercapto and sulfonic acid groups per θ'. More preferably, the catalytically-active materials will include those having 1 or 2 of each of mercapto and sulfonic acid groups per θ'. Most preferably, the catalytically-active materials contain 1:1 ratios of mercapto and sulfonic acid functions and will correspond to the general formula

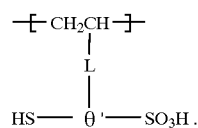

Exemplary polymers, made from ethylenically unsaturated monomers and which can be used as carriers for the catalytically-active species, include, but are not limited to:

| L | θ' | Monomer(s) |
|---|---|---|
| — | phenyl | styrene |
| —CH$_2$— | phenyl | allylbenzene |
| —O— | phenyl | phenyl vinyl ether |
| —COO— | alkyl, aryl | acrylic esters |
| —OCO— | alkyl, aryl | vinyl esters |
| —(CH$_2$)$_r$— r = 4–20 | alkenyl | α,ω-diolefins |
| —NH— | alkyl, aryl | vinylamines |
| —CONH— | alkyl, aryl | acrylamides |
| —NHCOO— | alkyl, aryl | vinylurethanes |
| — | alkylphenyl | vinyltoluene |
| — | phenyl | α-methylstyrene |
| —S— | phenyl | phenyl vinyl ether |
| —SO$_2$— | aryl | vinyl aryl sulfones |
| —SO— | aryl | vinyl aryl sulfoxides |
| —NSO$_2$— | aryl | aryl sulfonamide |

The linking groups, —L—, can accordingly include alkylene, a covalent bond, oxycarbonyl, carbonyloxy, oxy, ureido, amido, amino, thio (sulfur), sulfono or sulfoxo. Preferred linking groups include a covalent bond, methylene, sulfur or oxygen, more particularly a covalent bond joining a phenyl ring to a carbon backbone in polystyrene or polystyrene derivatives, containing each of SH and SO$_3$H functions in single monomeric units of polystyrene.

One type of novel catalytically-active polystyrene resins, includes unit structures represented by Formula IV

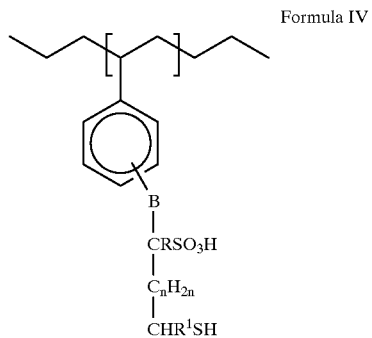

Formula IV wherein B is a bridging group, R and R$^1$ are independently selected from H, alkyl or aryl, —C$_n$H$_{2n}$— is straight or branched chain alkylene and n is an integer from 0 to about 20.

The bridging group B, can be selected from alkylene, generally as above. Alkyl and aryl are defined above.

Polystyrene resins of Formula IV can be made by the steps of (a) reacting a haloalkystyrene polymer with a lithiated sultone, (b) treating a resulting sultone-functionalized polymer with a reactive thiolate and (c) acidifying the resulting intermediate to produce a polymer containing (mercaptosulfoalkyl)styrene units.

Haloalkylstyrene polymers include, but are not limited to poly(chloromethylstyrene), poly(bromomethylstyrene), poly(bromopropylstyrene), poly(bromopentyl)styrene or the like. including homopolymers and copolymers, whether made by polymerization of haloalkylstyrene monomers or haloalkylation of polystyrene resins. Representative starting materials can be made by copolymerization of vinylbenzyl chloride or vinylbenzyl bromide with styrene. Either starting material can be crosslinked with divinylbenzene or similar crosslinking monomers. The polymers can contain other monomers, e.g., styrene, α-methylstyrene, acrylonitrile, butadiene, maleic anhydride, ethylene or propylene.

The haloalkylated polymers will advantageously contain from about 0.5 meq/g to about 10 meq/g of halomethyl groups. Halomethylated or haloalkylated polymers normally comprise mixtures of polymers, substituted in the ortho-, meta- and para-positions.

Poly(chloromethylstyrene), containing about 2–5 meq/g of chlorine, is a preferred starting material.

The reaction sequence described above can be performed utilizing a variety of chloromethylated or bromomethylated styrene polymers or copolymers. In particular, crosslinked halomethylated styrene/divinylbenzene co-polymers in various forms, e.g. microporous or macroporous beads, powders, etc., can be functionalized to provide the corresponding mercaptosulfonic acid polymers.

In the case of all the polymer based catalysts utilization of the functionalized styrene or other polymers in bead form may advantageously simplify workup procedures during preparation and provide for more facile implementation in catalyst applications. Beads are suitably of any size through which effective flow and contact is achieved. Physical forms including powders, beads, extruded shapes, macroporous and microporous configuration are, however, suitably used in the practice of the invention. In general smaller size provides more surface area for contact, but larger size permits greater flow through a bed. Optimizing these factors is within the skill in the art.

Reactive thiolates advantageously include, but are not limited to, sodium thioacetate, potassium thioacetate, ammonium thioacetate and lithium thioacetate and the corresponding hydrosulfides. Of these, lithium, sodium or potassium thioacetate is preferred.

When conversion to a mercapto function is done through a thiourea intermediate, the thioureas are advantageously selected from thiourea, N-methylthiourea, N-ethylthiourea, N-phenylthiourea or the like. In another alternative procedure, sodium thiosulfate can be used.

A preferred species of catalytically-active polystyrene resin is made by reacting poly(chloromethyl)styrene with lithiated 1,4-butanesultone to produce an intermediate sultone, represented by the structural unit formula:

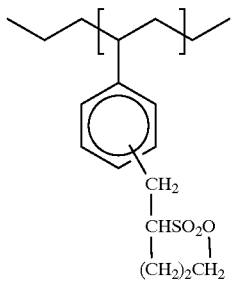

The resulting polymer contains ($\epsilon$-mercapto-$\beta$-sulfopentyl)styrene units, that is, n in Formula IV is 2 and B is —CH$_2$—.

Most preferably, this type of resin is made from a slightly crosslinked polystyrene; the resulting catalytically active material is designated as PMBSA-MER.

Another type of catalytically-active polystyrene resins can be prepared by the steps of:

(a) alkylating a polystyrene with an alkenyl halide of the formula $RC(R^1)=C(R^2)C_mH_{2m}CH(R^3)X$, wherein each of R, $R^1$, $R^2$ and $R^3$ is H, alkyl or aryl; m is 0 to about 20 and X is F, Cl, Br or I to produce a haloalkyl polystyrene;

(b) sulfonating the resulting haloalkylpolystyrene to produce an intermediate having sulfo functional groups;

(c) optionally converting the sulfo functional groups to a sodium or potassium sulfonate function;

(d) thiolating the thus-produced sulfostyrene intermediate by reacting the halo function with a reactive thiolate to produce a corresponding mercapto function or precursor thereof and (e) optionally hydrolyzing the thus-thiolated intermediate with an acid or base when the thiolated group so requires; and (f) optionally acidifying (if so required) to produce the sulfonic acid function.

This process can be represented broadly by the reaction sequence:

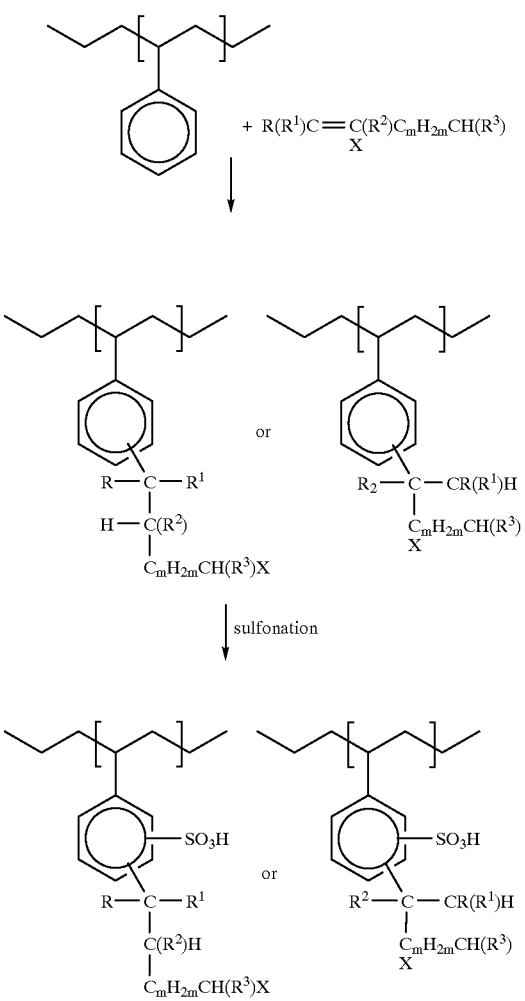

to produce intermediate haloalkyl sulfonated styrene polymers, of which halo functions are converted to mercapto functions to produce the following types of products of Formula V:

Formula V

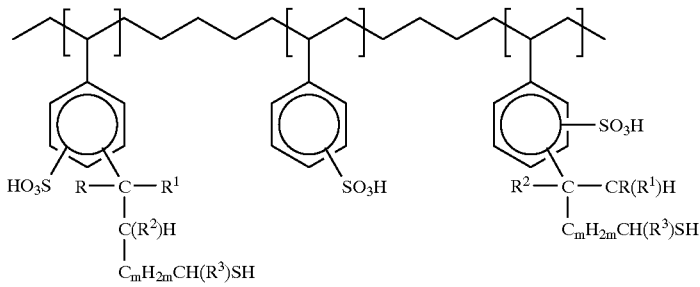

Alkenyl halides optionally contain aryl and alkyl substituents, as defined above. Representative alkenyl halides, useful for preparing the catalytically-active polymers, include, but are not limited to, allyl chloride, allyl bromide, allyl iodide, methallyl chloride, methallyl bromide, crotyl chloride, crotyl bromide, 4-bromo-1-butene, 5-bromo-1-butene, 6-bromo-1-hexene or higher chloro or bromoalkenes. Preferably, the alkenyl halides are allylic halides, represented by the formula $RC(R^1)=C(R^2)CH(R^3)X$. Most preferably, the alkenyl halide is 5-bromo-1-pentene, 11-bromo-1-undecene or allyl bromide.

A particularly preferred product thus made can be characterized by the formula, in the case of a product from 5-bromo-1-pentene:

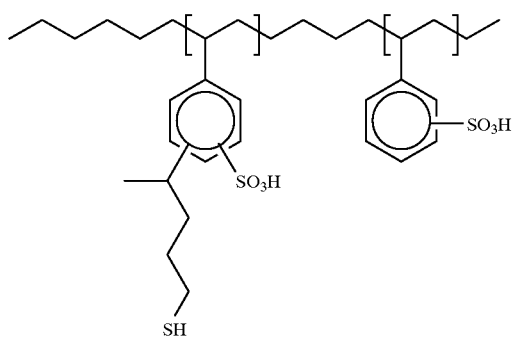

or, when the halide is allyl bromide or allyl chloride, by the formula:

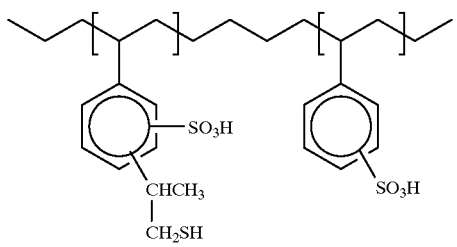

Reactive thiolates are as defined above. Most preferably, the reactive thiolate is an alkali metal thioacetate or hydrosulfide.

By varying the choice of starting bromoalkene (or other haloalkene) used in the alkylation step of the process, the basic procedure described above can also be used to prepare a variety of catalysts with varying chain lengths between the mercaptan and sulfonic acid moieties. A number of catalysts with different amounts of mercaptosulfonic acid sites, depending upon the degree of functionalization in the alkylation and sulfonation steps in the process, and structural relationships between the mercaptan and sulfonic acid sites, depending upon the choice of bromo- or chloroalkylating agent, can accordingly be made.

Preferred catalytically-active species of Formula V are those derived from polystyrenes, treated with 5-bromo-1-pentene, 11-bromo-1-undecene or an allylic halide of the formula $RCH=CH_2CH_2X$, wherein R is H or alkyl of 1–5 carbon atoms.

In another aspect, this invention relates to novel [(mercaptoalkyl)(sulfo)phenylalkyl] sulfonated polystyrene catalysts, made by a process comprising the steps of:

(a) alkylating a haloalkylated polystyrene with a haloalkylarylene compound to produce an intermediate haloalkylpolystyrene having [(haloalkyl)phenylalkyl] styrene units;

(b) sulfonating the thus-produced haloalkylpolystyrene intermediate to produce an intermediate having sulfo functional groups;

(c) optionally converting the sulfo functional groups to corresponding alkali metal salts;

(d) thiolating the thus-produced sulfostyrene intermediate by reacting the halo function with a reactive thiolate to produce a corresponding mercapto function or precursor thereof and (e) optionally hydrolyzing the thus-thiolated intermediate with an acid or base when the thiolated group so requires; and (f) optionally acidifying (if so required) to produce the sulfonic acid function.

This process produces polymers having repeating units of the formula:

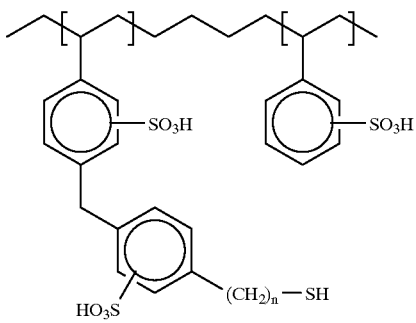

wherein n is preferably an integer from 0 to 10, more preferably 2 or 3.

A representative member of this series of polymers, designated as DPMSA-XE3C is made from chloromethylstyrene polymer and 3-bromopropylbenzene, in accordance with the following reaction sequence:

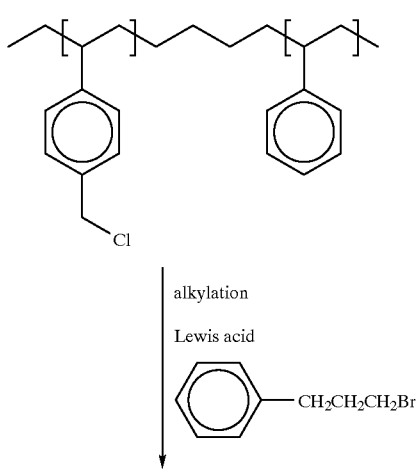

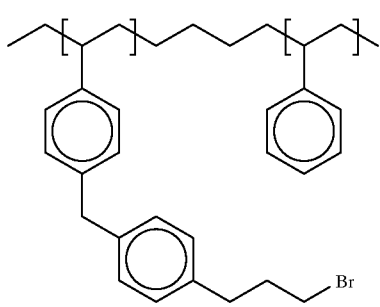

-continued

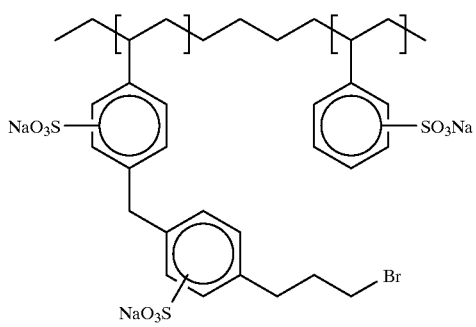

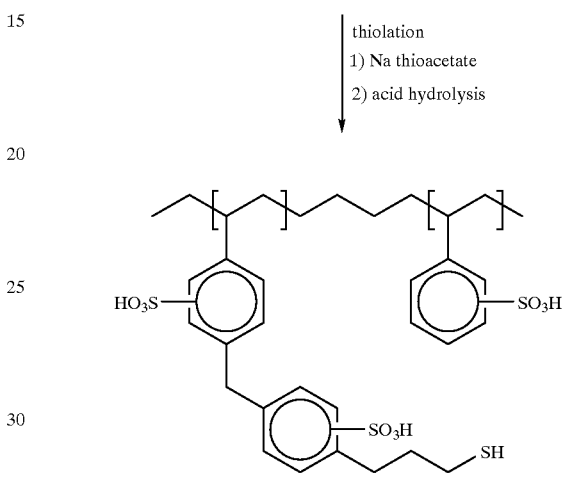

The haloalkyl polystyrene starting materials can advantageously be selected from chloromethylated polystyrenes, bromomethylated polystyrenes, chloroethylated polystyrenes, iodoethylated polystyrenes or the like, generally as above, preferably the halomethylated polystyrenes. Those skilled in the art recognize that selectivity decreases with haloalkyl groups on aryl rings which groups have similar selectivity.

The haloalkylaryene compound can conveniently be selected from chlorobenzene, (chloromethyl)benzene, (chloroethyl) benzene, (chloropropyl)benzene, (chlorobutyl) benzene, as well as the corresponding fluoro, bromo and iodo analogues. Representative examples include (2-chloroethyl)benzene, (2-bromoethyl)benzene, (2-iodoethyl)benzene, 1-chloro-3-phenylpropane, 1-bromo-3-phenylpropane, and 1-iodo-3-phenylpropane. The bromo compounds are preferred.

The alkylation is conveniently carried out in the presence of a Friedel-Crafts catalyst, of which aluminum trichloride, aluminum bromide, boron trifluoride, hydrogen fluoride, phosphoric acid, zinc chloride, titanium chloride, ethylaluminum dichloride and stannic chloride are representative. A preferred catalyst is aluminum chloride in nitromethane or nitrobenzene, as disclosed by A. Warshawsky et al., "Functionalization of Polystyrene. I. Alkylation with Substituted Benzyl Halide and Benzyl Alcohol Compounds," *J. Org. Chem.*, vol. 43 (1978), pages 3151–3157.

Conveniently, after alkylation, unreacted haloalkylbenzene, solvent and catalyst in admixture are removed from the alkylated polystyrene by means within the art such as filtration. Advantageously, the admixture is recycled for reaction with additional haloalkyl polystyrene. The alkylated polystyrene is optionally washed with a solvent such as dichloromethane and optionally dried.

The resulting alkylated polystyrene is sulfonated using chlorosulfonic acid, oleum or other known sulfonating agents. Prior to conversion of the halo moiety to the mercapto moiety, it is convenient to convert the sulfo moieties to corresponding alkali metal salts. Chlorosulfonic acid, sulfuric acid or sulfur trioxide is conveniently used in an amount sufficient to achieve a predetermiend or desirable degree of sulfonation, advantageoulsy to avoid unnecessary workup, in an amount not in large excess of the sufficient amount which varies with each resin but is determined without undue experimentation. The advantages of lower reaction temperatures are greater with chlorosulfonic acid.

The thiolating reagents are conveniently selected from those disclosed above. Sodium thioacetate is preferred. Excess sodium hydrosulfide is optionally used for thiolation. Hydrolysis is then unnecessary since a thio group rather than a thioacetate is formed. The intermediate thiolated compound is, if necessary, acidified with a strong acid to convert sulfonate salt moieties to corresponding sulfonic acid moieties. Advantageously, a mineral acid is used, as above.

In an alternate embodiment, the process comprises:

(a) alkylating a polystyrene resin with a halomethyl haloalkylarylene compound to produce an intermediate having [(haloalkyl)phenylalkyl] styrene units, (b) sulfonating the thus-produced intermediate to produce an intermediate having sulfo functional groups;

(c) optionally converting the sulfo functions to corresponding alkali metal salts;

(d) thiolating the thus-produced sulfostyrene intermediate by reacting the halo function with a reactive thiolate to produce a corresponding mercapto function or precursor thereof and (e) optionally hydrolyzing the thus-thiolated intermediate with an acid or base when the thiolated group so requires; and (f) optionally acidifying (if so required) to produce the sulfonic acid function.

Illustrative of this reaction is the following sequence:

It is within the skill in the art to select halomethyl haloalkylarylenes in which the haloalkyl and halomethyl groups have activities sufficiently different to achieve the desired result.

Representative halomethyl haloalkylarylene compounds include (2-bromoethyl)benzylchloride and (3-bromopropyl) benzylchloride. Chloromethyl haloalkylarlenes are conveniently prepared by means within the skill in the art such as described by Selva et al., Synthesis, 1991, 1003–1004 wherein haloalkylarylenes are reacted with formaldehyde in acid (e.g. sulfuric or hydrochloric) in the presence of a quaternary ammonium phase transfer catalyst. Chloromethylation can also be performed using zinc chloride and paraformaldehyde in accordance with the method described by Daren in U.S. Pat. No. 4,967,026. Alternatively, chloromethyl ethers are used to chloromethylate a haloalkyl arylene by methods similar to that taught by Raley in U.S. Pat. No. 3,311,602, by Shinka, et al. *J. Poly. Sci. Polym. Lett. Ed.* 14(1), 1–3 (1976), and by Shigeo, et al. *Chem. Abstr.* 72:32290 (1970), or by other means within the skill in the art.

In another aspect, hydrohalogenating agents such as HBr are added to alkenyl arylenes such as styrene under radical forming conditions such as taught by Martan in U.S. Pat. No. 4,228,106 or Plesmid in U.S. Pat. No. 3,321,536 which patents are incorporated herein by reference in their entireties. In an extension of these works, vinylbenzyl chloride is hydrobrominated by this method.

The sulfonation and thiolation steps are as described for the previous process.

In addition to the methods disclosed above, a variety of other methods are also available for preparing the haloalkyl-functionalized polystyrene resins which are precursors to the mercaptosulfonic acid polymer catalysts. Representative approaches for preparing the haloalkylated polystyrene resins include (but are not limited to) those described or discussed by: a) P. C. Reeves and M. S. Chiles, "Phase Transfer Catalysts Anchored to Polystyrene," *Tetrahedron Letters* (1979), pages 3367–3370 b) M. Tomoi, et. al., "Novel Synthesis of Spacer-Modified Polymer Supports and

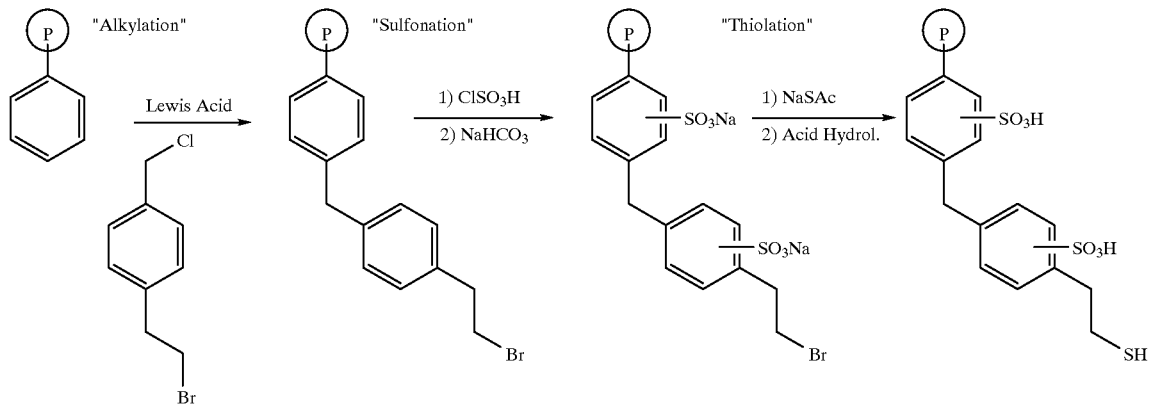

The alkylating step is performed as in the preceding process optionally in a solvent such as chloroform, 1,2-dichloroethane, dichloromethane, 1,2-dichloropropane, preferably a solvent which swells polystyrene (e.g. styrene/divinylbenzene copolymer beads). The alkylating agent is any halomethyl haloalkylarylene preferably wherein the alkyl group has from 0 to about 10 carbon atoms. The arylene group preferably has from 6 to about 14 carbon atoms.

Activity of Phase-Transfer Catalysts Derived from the Polymer Supports," *J. Polymer. Sci. Polymer Chem. Ed.*, vol. 20 (1982), pages 3015–3019 c) M. J. Farrall and J. M. J. Fréchet, "Bromination and Lithiation: Two Important Steps in the Functionalization of Polystyrene Resins," *J. Org. Chem.*, vol. 41 (1976), pages 3877–3882 d) S. P. McManus and R. D. Olinger, "Reactions of Cyclic Halonium Ions and Alkylene Dihalides with Polystyryllithium. Preparation of Haloalkylated Polystyrene," *J. Org. Chem.*, vol. 45 (1980), pages 2717–2719 e) M. Haratake, et. al. "Sorption of Phenols on Anion-Exchange Resins Having .omega.-Oxoalkyl or .omega.-Hydroxyalkyl Spacer," *Analytical Sciences*, vol. 4 (1988), pages 591–594 f) M. Gauthier and A. Eisenberg, "Alkylated Styrene Ionomers with Variable Length Spacers. I. Synthesis," *J. Polymer Sci.: Part A: Polymer Chem.*, vol. 28 (1990), pages 1549–1568 g) P. Tundo, "Easy and Economical Synthesis of Widely Porous Resins; Very Efficient Supports for Immobilized Phase-Transfer Catalysts," *Synthesis* (1978), pages 315–316 h) Tachikawa, et. al. "Process for the Production of Silanes" (U.S. Pat. No. 4,725,420) i) G. Zheng, et. al. "Synthesis of Bromoalkylated Crosslinked Polystyrene," *Xinan Shifan Daxue Xuebao, Ziran Kexueban*, vol. 2 (1986) pages 68–70 j) M. L. Hallensleben, "Preparation of Poly(p-(.omega.-lithiumalkyl)styrenes) and Their Use as Polymer Metalating Agents," *Angew. Makromol. Chem.*, vol. 31 (1973), pages 147–159 k) F. Döscher, et. al., "Synthesis of Sulfoalkylated Styrene-Divinylbenzene Copolymers," *Makromol. Chem., Rapid Commun.*, vol. 1 (1980), pages 297–302. It is to be understood that a haloalkylated polystyrene resin prepared in a manner such as that described in the above references could be further functionalized by the sulfonation and thiolation procedures previously described to provide a mercaptosulfonic acid polymer catalyst.

Other representative references on methods for polymer modification or for uses of functional polymers include Akelah et al., "Application of Functionalized Polymers in Organic Synthesis," *Chem. Rev.*, vol. 81 (1981), pages 557–587; Fréchet et al., "Functionalization of Crosslinked Polystyrene Resins by Chemical Modification: A Review," in "Chemistry and Properties of Crosslinked Polymers," S. Labana, ed., Academic Press, New York (1977), pages 59–83; and Maréchal, "Chemical Modification of Synthetic Polymers," in "Comprehensive Polymer Science," vol. 6, Allen, ed., Pergamon Press, New York, pages 1–47.

Catalysts derived from polystyrenes will advantageously contain from about 0.2 to about 5 meq of mercapto/sulfonic acid functionality per g, most preferably from about 2 to about 4 meq/g.

It will be understood that polymers, containing large amounts of mercapto/sulfonic acid functionality on a given carrier, pendant from a hydrocarbon chain, can be prepared by grafting vinylsulfonic acid, propenesultone, or the like, to the pendant carrier function, and converting the grafted polymer to materials having mercapto/sulfonic acid functionality.

Catalytically-active polymers in which — is an ionic bond can advantageously be prepared from ion-exchange resins and reactive compounds, containing both mercapto and sulfonic acid functions.

For example a strongly basic ion-exchange resin such as poly(vinylbenzyl amine) can be reacted with a compound such as 4-mercapto-1,2-butanesulfonic acid to produce catalytically-active material as represented by the equation:

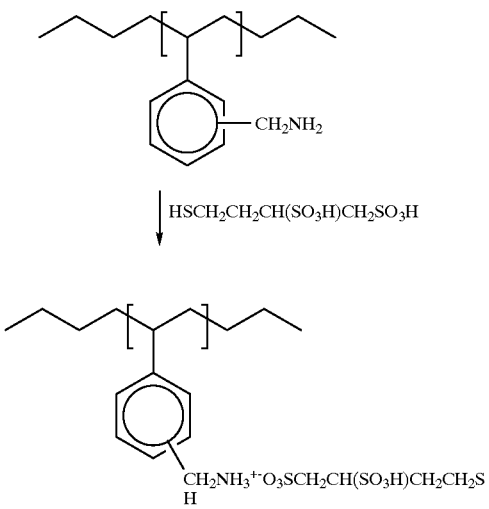

Representative strongly basic ion-exchange resins include Dowex™ 1×2–400, Amberlyst™ A-21, Dowex™ WGR-1, Dowex™ WGR-2 and Dowex™ MSA-1. The WGR resins are polypropyleneimines, conveniently obtained by condensation of epichlorohydrin with ammonia.

Catalytically-active materials can also advantageously be prepared from an acidic ion-exchange resin, e.g. sulfonated polystyrene by reaction with an aminomercaptosulfonic acid, e.g. 2-mercapto-4-aminobenzene sulfonic acid, as represented by the equation:

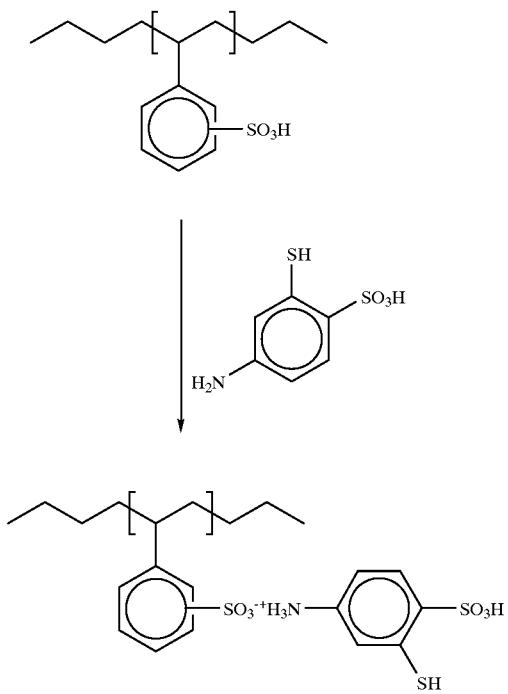

Representative strongly acidic cation-exchange resins include Dowex™ 50×2–400, Amberlyst™ A-21 and Dowex™ MSC-1.

In addition to the use of polymers from ethylenically unsaturated monomers, including copolymers, as insoluble supports for the catalytically-active species, the catalytically-active species can be attached to an inorganic support, e.g. a mineral, such as silica, alumina, aluminosilicates or glass, through the linking group —L—. A representative case is that wherein the linking group is —OSiO— or

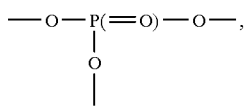

most preferably, —OSiO—.

Catalytically-active species of Formula III will conveniently be incorporated in the backbone of condensation polymers, e.g. polyesters, polyamides, polycarbonates, polyurethanes, polysiloxanes, polyamines, polyethers, polyketones, polysulfones, polysulfoxides and the like. The divalent linking group, —L'—, can be selected from such structures as polyoxy(alk-di-yl), polyoxy(ar-di-yl), dioxy (alkar-di-yl), polyoxy(aralk-di-yl), polythio(alk-di-yl), polythio(aralk-di-yl), polythio-(ar-di-yl), polythio(alkar-di-yl), polythio(aralk-di-yl), polyamido(alk-di-yl), polyamido (ar-di-yl), polyamido-(aralk-di-yl), polycarbonyloxy(alk-di-yl), polycarbonyloxy(ar-di-yl), polycarbonyloxy(alkar-di-yl), polycarbonyloxy(aralk-di-yl), polycarbonyldioxy(alk-di-yl), polycarbonyldioxy(ar-di-yl), polycarbonyldioxy (alkar-di-yl), polycarbonyldioxy(aralk-di-yl), polyamino (alk-di-yl), polyamino(ar-di-yl), polyamino(alkar-di-yl), polyamino(aralk-di-yl), polycyclimido(ar-di-yl), polycyclimido(alkar-di-yl), polycyclimido(aralk-di-yl), polycarbonyl(alk-di-yl), polycarbonyl(ar-di-yl), polycarbonyl-(alkar-di-yl), polycarbonyl(aralk-di-yl), polyimido(alk-di-yl), polyimido(ar-di-yl), polyimido(alkar-di-yl), polyimido(aralk-di-yl), polyureylene(alk-di-yl), polyureylene(ar-di-yl), polyureylene(aralk-di-yl), polyureylene alkar-di-yl), polycarboxamideoxy(alk-di-yl), polycarboxamideoxy(ar-di-yl), polycarboxamideoxy(alkar-di-yl), polycarboxamideoxy(alkar-di-yl), polycarboxamideoxy(aralk-di-yl), ar-di-yl, alkaryl-di-yl, aralkyl-di-yl and alkenoic-di-yl. Preferred divalent linking groups, —L'—, include di(carbonyloxy)hydrocarbylene, siloxy, dicarboxamidohydrocarbylene, di(oxycarbonyl) hydrocarbylene, dithiohydrocarbylene, and hydrocarbylene groups containing aromatic rings.

During batch processing, the mercaptosulfonic acid catalyst is suitably present in an amount sufficient to enable condensation of the phenol with the ketone/aldehyde in a reasonable time. Preferably, the amount of mercaptosulfonic acid ranges from about 0.01 equivalents to about 2.0 equivalents of catalyst per 1.00 equivalents of the ketone/aldehyde. More preferably, the amount of mercaptosulfonic acid catalyst is from about 0.02 to about 1.0 equivalent of mercaptosulfonic acid per equivalents of aldehyde/ketone. Most preferably, the reaction mixture will contain from about 0.03 to about 1.0 equivalent of mercaptosulfonic acid per equivalents of aldehyde or ketone under batch processing.

When ketone/aldehyde is added over the course of a reaction (e.g. a continuous reaction) the previously stated preferred amounts refer to total catalyst and reactants added rather than catalyst present in a reaction mixture at a given moment. Those skilled in the art recognize that when a reactant is added incrementally or continuously, there is often a large excess of catalyst. The ratio of catalyst to ketone/aldehyde in the reaction mixture is advantageously greater than one, conveniently on the order of 20 equivalents to 1 equivalent.

Due to the high activity of the mercaptosulfonic acid catalysts, good reaction rates and high selectivity can be obtained at temperatures below the melting point of phenol. The phenol reactant can advantageously be kept in the liquid state by addition of solvents, e.g., water, methylene chloride, diphenylmethane, etc. Low temperature reactions are often particularly advantageous, because the product diphenolic compounds crystallize in the reaction mixture and because lower reaction temperatures favor higher selectivity toward 4,4-bisphenolic products.

The reaction temperature will accordingly advantageously be selected in the range from about 0° C. to about 100° C., preferably from about 15° C. to about 60° C. Temperature ranges can be chosen by routine experimentation, depending upon the ketone/aldehyde and phenol feeds.

When excess phenolic compound is used as solvent, the temperature for the condensation is advantageously selected so that the phenol is in the liquid state. In the case of high-melting phenols, e.g. those melting above about 180° C., the use of an inert solvent is preferred. Diphenylmethane has been found to be particularly useful for this purpose. Other useable inert solvents include, but are not limited to, the xylenes, mesitylene, the durenes, fluorobenzene, toluene, cyclohexane, chlorobenzene, halogenated aliphatic hydrocarbons and alkylnaphthalenes having low melting points.

If a solvent/diluent is used, the amount used conveniently ranges from about 5 mL to about 1 L per mole of ketone or aldehyde. Preferably, from about 200 mL to about 400 mL are used per mole of ketone or aldehyde.

The addition of water, generally in an amount up to a maximum of about 5% by weight of total feed, is considered highly desirable in processes for the preparation of bisphenol A, because water lowers the freezing point of phenol and addition of water permits the condensations to be run at lower temperatures than otherwise. Most preferably, the amount of added water is from about 1% by weight to about 5% by weight of total feed.

The reaction can advantageously be carried out by stirring the ketone or aldehyde and mercaptosulfonic acid into molten phenol in such a way that the temperature in the reaction vessel will not rise above about 150° C.

The molar ratio of phenolic reactant to ketone or aldehyde is advantageously selected so that at least two moles of phenol will condense with the ketone to produce a corresponding bisphenol or higher condensate. Therefore, molar ratios of 2:1 or higher will advantageously be selected. It is preferred to carry out the reactions using larger excesses of phenolic reactant, up to as much as 50 moles of phenol per mole of ketone or aldehyde. It will be understood that the excess phenol acts as a solvent or diluent, as well as a reactant.

Lower ratios of phenol to ketone/aldehyde are generally accompanied by an increase in the amount of by-products formed. In the preparation of polyphenols, it has been found that molar ratios from about 2:1 to about 30:1 of phenol to aldehyde/ketone are preferred. More preferably, the reaction mixtures will contain from about 4:1 to about 25:1 molar ratios of phenol to aldehyde/ketone. Most preferably, the molar ratio is from about 6:1 to about 25:1.

Since the condensation reaction is exothermic, the reactants, instead of being mixed together all at once, are optionally progressively mixed together at a speed depending upon the intensity of the cooling employed to maintain the temperature of the reaction medium within the optimum limits. After the mixing of the reactants, they are preferably left in contact for some time in order to complete the condensation. The duration of the introduction of the reactants during a batch process conveniently varies from 15 min to 1 h.

In batch processes, the reactants and the catalyst are preferably thoroughly stirred mechanically to assure better mixing, and hence an improved space-time yield.

When the process of this invention is conducted batchwise, the reaction time is advantageously in the range of about 0.1 to about 20 hours depending on the reaction conditions including the amount of the catalyst used, the reaction temperature, and specific reactants, solvents and products.

The process of this invention can also be run in continuous mode, more preferably by use of a series of continuous stirred tank reactors, the use of which approximates plug flow reaction conditions. It is preferred to carry out the process of this invention under continuous reaction conditions.

The pressure in the reaction zone is not critical, but preferably ranges from about 0.001 to about 10 bar (0.1 to 1000 kPa), and more particularly from about 0.5 to about 3 bar (50 to 300 kPa). In many cases, it will be preferred to carry out the reactions under ambient pressure, that is, about 1 bar (100 kPa).

During the reaction, one mole of water is evolved for each mole of ketone/aldehyde undergoing the condensation with phenol. It has been found that adding water to the reaction mixtures can be advantageous for decreasing the melting point of phenol. The water evolved during the reactions need not be removed by distillation/entrainment with an inert solvent in order to attain high reaction rates. In some cases, however, it will be preferred to entrain and remove water from the reaction mixture, in order to increase reaction rates.

It has been found that the soluble mercaptosulfonic acid catalysts can advantageously be removed from the crude product by extraction with water. The aqueous extracts can be concentrated and recovered mercaptosulfonic acid catalyst can be optionally recycled to subsequent runs. When the phenolic starting material is phenol, a solution of the mercaptosulfonic acid in phenol is conveniently recovered and is optionally recycled without further purification.

The acid concentration can be reduced below about the limits of detection, and probably below about 1 ppm by weight of acid, by repeated extractions with water. The facile removal of catalyst from the reaction mixtures is a significant advantage over the prior art, using mixtures of condensing agents. It is within the practice of this invention to remove the mercaptosulfonic acid by continuous counter-current extraction.

The time for phase separation during extraction of the acid catalyst is of the order of 10–15 min under batch conditions, without a drag layer. Stirring speed during the extraction in a mixer/settler is adjusted so as to avoid emulsion formation.

The soluble mercaptosulfonic acid catalysts can also be removed from reaction mixtures by extraction with a solution of an alkali metal hydroxide, carbonate or bicarbonate.

In addition, the soluble mercaptosulfonic acid catalysts can be removed from reaction mixtures by passing the reaction mixture through a column of anion-exchange resin or amine resin, such as Dowex™ WGR.

A water purge from the process will contain phenol plus catalyst. This purge is advantageously treated to remove phenol by extraction with methyl isobutyl ketone before being sent to a bio-pond for disposal.

For isolation of BHPF from reaction mixtures, made using a soluble catalyst, a phenol/water mixture is preferably distilled from the water-washed mixture until the weight ratio of phenol:BHPF is below about 1.5:1. Most preferably, phenol is removed until the phenol:BHPF weight ratio is from about 1.5:1 to about 0.5:1. It has been found particularly advantageous to dissolve the resulting material in hot methylene chloride and cool the resulting solution to obtain crystalline BHPF.

Very highly purified BHPF accordingly can be obtained by a process wherein a resulting crude product is washed with water to remove $(HS)_a$—0—$(SO_3H)_b$; the resulting acid-free mixture is distilled to remove phenol and water until the phenol:9,9-bis-(4-hydroxyphenyl)fluorene weight ratio is less than about 1.5; the resulting mixture is taken up in hot methylene chloride and the resulting solution is cooled to produce crystalline 9,9-bis-(4-hydroxyphenyl) fluorene. BHPF purified in this way can be used to make ultrahigh quality polycarbonate resins.

Excess phenol can also be removed by boiling the reaction mixture repeatedly with water, optionally with the use of a water-miscible organic solvent such as methanol. The aqueous solution is separated each time and the product, then practically pure, is dried. Another effective method of removing excess phenol is by steam distillation.

The reaction product solution is optionally then concentrated by evaporation and repeatedly extracted with boiling water for the removal of excess phenol. The product so obtained is optionally then recrystallized for further purification.

BHPF can be isolated from the reaction mixtures in several additional ways. The method selected will depend on the degree of purification desired as well as the composition of the reaction mixture, the desired production rate, etc.

When extensive purification is undesirable or inappropriate, the mixture, after being treated to remove catalyst, can be treated with a volume of hot water sufficient to dilute the mixture and bring about precipitation of BHPF. Alternatively, the reaction mixture can be added to hot water and the phenol removed in the form of a water/phenol azeotrope until the phenol content is lowered sufficiently to permit precipitation of BHPF from the mixture. The BHPF solids can be collected and dried before use or can be used in the form of a slurry.

When more extensive purification of BHPF is desired, the solids can be purified by precipitation from a solvent, e.g. diphenylmethane or methylene chloride.

Another method for isolating BHPF comprises adding to the reaction mixture, at the end of the reaction, a solvent, boiling at a higher temperature than phenol, and removing phenol from the phenol/BHPF/solvent mixture until BHPF crystallizes or precipitates from the mixture. This method can be carried out by adding diphenylmethane or triisopropylbenzene to a reaction mixture, from which catalyst has been extracted or removed, prior to distilling the mixture. Alternatively, the solvents can be added to the initial reaction mixture so that the reactions are run in the presence of the solvent. The reaction mixture is worked up by extracting to remove catalyst and by then distilling to remove solvent and phenol, until BHPF crystallization occurs.

BHPF can also be isolated by adding to a reaction mixture a solvent, which boils at a higher temperature than phenol and dissolves sufficient BHPF, in the absence of phenol, that removing phenol from the phenol/BHPF/solvent mixture provides a homogeneous solution, cooling of which causes crystallization of BHPF. Solvents meeting these requirements include diphenylmethane, diphenyl ether, dodecane, naphthalene, Isopar™ (hydrocarbon mixture commercially available from Exxon Corporation) and triisopropylbenzene.

Further purification can also be accomplished, after removing catalyst from the reaction mixture, by distilling to remove phenol to a level at which BHPF crystallizes from the phenol/BHPF mixture. The BHPF solids obtained can be isolated by conventional means and then further treated, e.g., by washing with water to remove phenol.

An alternative method for obtaining high purity BHPF comprises removing catalyst from the reaction mixture, distilling phenol from the reaction mixture to a phenol/BHPF level such that dilution of the distillation residue with a solvent induces crystallization of the BHPF from the phenol/BHPF/solvent mixture. For example, phenol can be removed by distillation until the distillation residue contains about 50% by weight of phenol and about 50% by weight of BHPF. Methylene chloride, triisopropylbenzene or toluene can be added to the residue and the resulting solution can be cooled to bring about crystallization of highly purified BHPF.

Another procedure for isolating pure BHPF solid from the reaction comprises removing the mercaptosulfonic acid catalyst, distilling phenol from the resulting mixture, to produce a still residue, to which addition of a solvent induces crystallization of BHPF. For example, a still residue containing 80% by weight of phenol and 20% by weight of BHPF can be diluted with a solvent, e.g. dichloromethane or toluene, to induce crystallization of BHPF.

In addition, BHPF can be isolated from a reaction mixture, by removing the mercaptosulfonic acid catalyst, adding to the resulting reaction mixture a solvent, which forms an azeotrope with phenol and in which BHPF is soluble in the absence of phenol, and removing phenol from the mixture by azeotropic distillation. Cyclohexanol is exemplary of a solvent, which will form an azeotrope with phenol and from which BHPF will precipitate upon cooling the still residue from the azeotropic distillation.

Similarly, phenol can be removed from the reaction mixtures by addition of a solvent, which forms an azeotrope with phenol. After removing phenol by azeotropic distillation, the still residue is cooled and BHPF crystallizes out from the cooled mixture.

In any of the purification processes which result in a crystalline product, the catalyst is optionally not removed before crystallization of product but rather either tolerated in the product or removed from the crystals, for instance by washing or other means within the skill in the art, after crystallization.

In some cases, the condensation of phenol with ketones or aldehydes can be run in a solvent, e.g., methylene chloride, from which the product will precipitate during the course of the reaction, as is described in more detail for the preparation of bisphenol A.

A representative solvent used for crystallization of BHPF, methylene chloride, can be recovered from the mother liquors by batch distillation and recycled back to the process. The still bottoms contain BHPF and methylene chloride and can be cooled to recover additional BHPF. BHPF crystals thus formed are conveniently recovered using a basket centrifuge or pressure filter and can be recycled back to a main crystallizer. Crude mother liquor can also be recycled back to the phenol evaporation section.

When methylene chloride is used as solvent for crystallizing BHPF, a common vent header for collecting all vents from storage tanks and safety relief systems is recommended. The vent header system advantageously includes a flow measurement device in the inlet to a carbon adsorption unit and a VOC analyzer for the exit gas. The exit gas should contain less than 100 ppm of methylene chloride. A complete effluent treating system will advantageously include means for removing organics from process waters and means for removal of particulates from vent gas, e.g a water venturi to scrub particulates from the vent header.

A further advantage of the catalysts used in the practice of this invention is that the catalysts can be used to isomerize the crude product mixture, which typically contains (4-hydroxyphenyl)(2-hydroxyphenyl) compounds, the major bis-(4-hydroxyphenyl) compounds, and condensates, to produce more of the bis-(4-hydroxyphenyl) compounds.

The mercaptosulfonic acid catalysts of this invention are considerably less corrosive to stainless steel than the mixed catalysts used heretofore. Corrosion rates for stainless steel, below about 0.00254 cm/year, have been measured. The reaction mixtures are believed to be substantially free of halide ions, wherein "substantially free" means less than about 5000 ppm of chloride ions.

The process of this invention is advantageously carried out under conditions such that the concentration of chloride is below about 5000 ppm, preferably below about 1000 ppm, most preferably below about 100 ppm.

It is believed that the low corrosion rate is related to the absence of mineral acids, such as hydrochloric acid or sulfuric acid, from the reaction mixtures. The occurrence of corrosion in reactions using mineral acids has been noted by Knebel et al. '594 and Faler '995, supra.

The insoluble catalysts of this invention can be filtered from the reaction mixtures, washed with a mixture of ketone/aldehyde and phenol, and recycled to subsequent runs. Alternatively, the insoluble catalysts are used in fixed beds and the condensations of phenols with aldehyde/ketone is done in continuous upflow, crossflow or downflow fashion. When fixed bed catalytic reactors are used, the catalytically-active resins remain in the resin beds and need not be removed.

Further embodiments of this invention will be determined by the reactants used, the catalyst selected, the diluent, if any, and the reactor employed.

For example, when using a soluble catalyst for the condensation of phenol with 9-fluorenone, without a diluent, other than excess phenol or in the presence of a diluent which does not cause precipitation of product, it will generally be preferred to use a high ratio of phenol to fluorenone to maximize selectivity to the desired bisphenol product.

A particularly preferred process is one wherein the molar ratio of phenol:fluorenone is from about 4:1 to about 25:1; the reaction temperature is from about 25° C. to about 50° C.; the catalyst is mercaptopropanesulfonic acid or mercaptobutanesulfonic acid, used in an amount from about 5 to about 10 molar % with respect to fluorenone; the process is carried out under ambient pressure or under vacuum to remove water of reaction and increase the reaction rate; no cosolvent is used; the catalyst is removed from the product by extraction with water using a wash column or by batch extraction; the water extracts thus obtained are concentrated and recycled to the process; the product is isolated by removing excess phenol to a weight ratio from about 1.5:1 to about 0.5:1 of phenol:BHPF and the product is precipitated with dichloromethane.

When an insoluble catalyst is used, a particularly preferred process is one wherein the molar ratio of phenol:fluorenone is from about 4:1 to about 25:1; the condensation is carried out at a temperature from about 40° C. to about 60° C.; no cosolvent is used; the catalyst is PMBSA; the condensation is carried out in a continuous plug flow reactor; the reaction is carried out at ambient pressure or under reduced pressure to remove water of reaction and increase the reaction rate; the product is isolated by removing excess phenol to a weight ration from about 1.5:1 to about 0.5:1 of phenol:BHPF and the product is precipitated with dichloromethane.

The process for making BHPF can also be carried out at molar ratios of phenol:fluorenone from about 7:1 to about 5:1 in the presence of about 0.05 to about 0.15 equivalent of MPSA or MBSA per mole of fluorenone, wherein methylene chloride is added to the reaction mixture after conversion of at least 20% of fluorenone has occurred; heating the resulting mixture under reduced pressure to remove an azeotrope of methylene chloride and water; and cooling the mixture at the end of the condensation reaction to cause precipitation of BHPF.

The condensation of phenol with fluorenone can further be carried out using a feed containing from about 5:1 to about 3:1 molar ratio of phenol:fluorenone and about from about 0.05 to about 0.15 equivalent of MPSA or MBSA per mole of fluorenone, diluted with from about 10% by weight to about 30% by weight of methylene chloride. Crystalline BHPF can be collected from the cooled reaction mixture.

In addition, BHPF can be prepared from a reaction mixture, containing from about 18:1 to about 12:1 molar ratios of phenol:fluorenone and about 0.025–0.075 equivalent of MPSA or MBSA per mole of fluorenone at a temperature from about 50° C. to about 80° C., wherein the mixture at the end of the reaction is diluted with 10–20 volumes of water to extract mercaptosulfonic acid catalyst, the thus-washed mixture is distilled to a phenol:BHPF weight ratio from about 1.5:1 to about 1:1 and cooled to bring about crystallization of BHPF. The crystalline BHPF is removed by filtration and washed with methylene chloride and then with water.

A process in which the product is precipitated in the reaction mixture is preferred for the preparation of bisphenol A, more particularly a process wherein the phenol:acetone feed contains from about 6:1 to about 15:1 molar ratios of phenol:acetone; the condensation is carried out at a temperature from about 25° C. to about 35° C.; the reaction mixture contains up to about 5% by weight of water to lower the freezing point of phenol; the catalyst is 3-mercaptopropanesulfonic or 4-mercaptobutanesulfonic acid in an amount from about 0.05 to about 0.50 equivalent per mole of acetone in the acetone:phenol feed; the reaction is carried out under ambient pressure; and the crystalline bisphenol A produced by the process is removed by filtration or centrifugation.

Further processing can include washing the bisphenol A with water to partially remove soluble catalyst, and removing additional soluble catalyst by treatment with an anion exchange resin. It is believed that a preferred reactor configuration for this process is a series of continuous stirred tank reactors, so as to approximate plug flow reaction conditions.

Other process variations, include, but are not limited to:
(a) preparation of bisphenol A in neat phenol, using a soluble catalyst, with precipitation of bisphenol A in the reaction mixture and
(b) preparation of bisphenol A in phenol with a complex-forming cosolvent and soluble catalyst, with precipitation of bisphenol A in the reaction mixture.

More particularly, it is preferred to select a catalyst wherein at least 99% of the bisphenol A that crystallizes during the reaction is 4,4-bisphenol A. Such catalysts include soluble mercaptosulfonic acids in which a and b are each independently integers from 1 to 4 Preferred conditions include reaction temperatures from about 0° C. to about 50° C., more preferably from about 20° C. to about 40° C.

Representative complex-forming solvents for bisphenol A include diethyl ether, acetone, ethanol, propanol, dioxane, acetic acid, acetonitrile, methylene chloride or carbon tetrachloride. The complex-forming solvents complex preferentially with the 4,4-diphenolic isomer so that the resulting complex has solubility properties, differing from that of the uncomplexed 2,4-diphenolic compound and can be readily separated therefrom.

These processes can be run under varying pressure and temperature conditions, as well as reactant, cosolvent and catalyst concentrations, as can be determined by routine experimentation.

In one aspect, a most preferred process of this invention is that wherein the ketone is 9-fluorenone, the phenol is unsubstituted and the product is 9,9-bis-(4-hydroxyphenyl)fluorene; the molar ratio of phenol to fluorenone is from about 8:1 to about 25:1; the reaction mixture contains from about 0.05 to about 0.20 equivalent of mercaptosulfonic acid per mole of fluorene; the mercaptosulfonic acid compound is 3-mercaptopropanesulfonic acid or 4-mercaptobutanesulfonic acid and the process is carried out at a temperature from about 45° C. to about 60° C.

An equally preferred process is that wherein the ketone is acetone, the phenol is unsubstituted and the product is 2,2-bis-(4-hydroxyphenyl)propane; the molar ratio of phenol to acetone is from about 6:1 to about 15:1; the reaction mixture contains from about 0.10 to about 0.50 equivalent of mercaptosulfonic acid per mole of acetone; the mercaptosulfonic acid compound is 3-mercaptopropanesulfonic acid or 4-mercaptobutanesulfonic acid and the process is carried out at a temperature from about 15° C. to about 60° C.

Without further elaboration, it is believed that one skilled in the art can, using the preceding description, utilize the present invention to the fullest extent. The following preferred specific embodiments are, therefore, to be construed as merely illustrative and not limitative of the remainder of the disclosure in any way whatsoever.

In the following examples, the temperatures are set forth uncorrected in degrees Celsius. Unless otherwise indicated, all parts and percentages are by weight.

REACTORS

Reactor design 1: A 500-mL reactor prepared from PFA Teflon® is fitted with a thermocouple port, water condenser topped with nitrogen inlet, mechanical stirrer, drain port, and sampling port. Heating is provided with an infrared heat lamp and the temperature is controlled with an electronic thermometer/temperature controller.

Reactor design 2: A capped 4 dram glass vial with a magnetic stirrer. Heating is regulated by placing the vial in a temperature-controlled aluminum block heater.

Reactor design 3: A 100-mL jacketed glass reactor is fitted with a thermometer port, magnetic stirrer, nitrogen inlet, and sampling port. Heating is provided and the temperature is controlled by circulating glycol solution of the appropriate temperature through the jacketed flask using a Neslab Model RTE-220 circulating bath.

Reactor design 4: A 1.5 L, 2 L, or 3 L jacketed glass reactor fitted with a thermometer/sampling port, nitrogen inlet, and mechanical stirrer. Heating is provided and the temperature is controlled by circulating glycol solution of the appropriate temperature through the jacketed flask using a Neslab Model RTE-220 circulating bath.

ANALYTICAL

Analytical method 1: A Varian HPLC system (Model 9010 solvent delivery system, Model 9095 Autosampler, Model 9065 Polychrom diode array detector) interfaced with a Varian Star workstation is used for analysis. Area percent analysis is reported at 282 nm. Percent conversion is determined by an external standard method using calibrated concentration curves for each major component. Analytical HPLC samples are prepared by careful quantitative dilution of reaction samples (range: 400–500 times dilution). Column: Waters Nova-Pak C-18 (60 Angstrom, 4 micron, 3.9×150 mm). Chromatography conditions: flow rate 1.0 mL/min, solvent gradient (solvent A=water, solvent B=acetonitrile) 0 min: 65% A/35% B, 9 min: 60% A/40% B, 18 min: 55% A/45% B, 24 min: 45% A/55% B, 48 min: 5% A/95% B, 52 min: method end (10 min equilibration before and after runs).

Analytical method 2: A Hewlett-Packard HPLC system (Model 1084B solvent delivery system, Model 79850B LC terminal) is used for analysis. Area percent analysis is reported at 254 nm. Percent conversion is determined by an external standard method using calibrated concentration curves for each major component. Analytical HPLC samples are prepared by careful quantitative dilution of reaction samples (range: 400–500 times dilution). Column: Waters Nova-Pak C-18 (60 Angstrom, 4 micron, 3.9×150 mm). Chromatography conditions: flow rate 1.0 mL/min, solvent gradient (solvent A=water, solvent B=acetonitrile) 0 min: 65% A/35% B, 9 min: 60% A/40% B, 18 min: 55% A/45% B, 24 min: 45% A/55% B, 36 min: 25% A/75% B, 38 min: 65% A/35% B, 38 min: method end. NOTE: This method gives a smaller response (approximately one-half the area) for the 2,4-BHPF and the two:three adduct BHPF peaks relative to the 4,4-BHPF peak than either methods 1 or 3 using the diode array detector.

Analytical method 3: A Varian HPLC system (Model 9010 solvent delivery system, Model 9095 Autosampler, Model 9065 Polychrom diode array detector) interfaced with a Varian Star workstation is used for analysis. Area percent analysis is reported at 282 nm. Percent conversion is determined by an internal standard method using a solution of 0.0508 wt % acetophenone in 60/40 (wt./wt. %) methanol/water for preparing the samples. Analytical HPLC samples are prepared by careful quantitative dilution of reaction samples. Column: Waters Nova-Pak C-18 (60 Angstrom, 4 micron, 3.9×150 mm). Chromatography conditions: flow rate 1.0 mL/min, solvent gradient (solvent A=water, solvent B=methanol) 0 min: 55% A/45% B, 20 min: 15% A/85% B, 25 min: 10% A/90% B, 30 min: 55% A/45% B, 35 min: method end (10 min equilibration before and after runs).

Analytical method 4: The experimental setup of Method 1 is used. The chromatography conditions are: flow rate 1 mL/min, solvent gradient (solvent A=water, solvent B=methanol) 0 min: 55% A/45% B, 20 min: 15% A/85% B, 25 min 10% A/90% B. Analysis—Internal Standard method using 0.0508% acetophenone in 60% methanol/water. Average rel. std. deviations ranges from 1 to 2%, depending upon peak analyzed.

Analytical method 5: The reaction mixture is diluted with acetonitrile to a concentration of 0.01–0.1% by weight of components and the diluted sample is analyzed by HPLC on a Waters NovaPak C18 column (10.16 cm×0.635 cm inner diameter) connected to a Varian 9100 UV detector, set at 280 nm. The column temperature is 30° C., the pressure is 140 atm at 0 min, the absorption full scale for the detector is 2.0, the integrator attenuation is 3 and the chart speed is 0.5 cm/min. The autosampler injects 20 microliters of sample onto the column every 36 min. Reservoir A contains megapure water and reservoir B HPLC grade acetonitrile. The following protocol is used:

| Time (min) | Flow Rate (mL/min) | % B |
|---|---|---|
| 0 | 1.0 | 40 |
| 8 | 1.0 | 40 |
| 20 | 1.0 | 60 |
| 26 | 1.0 | 99 |
| 30 | 1.0 | 40 |

The peak area generated by each component in the sample is used with its known response factor, and the dilution ratio, to calculate the concentrations of each component in the sample solution.

REAGENTS

Fluorenone (Aldrich 98%), ~0.5% fluorene and methyl-fluorenes

Acetone (Baker reagent, dried over molecular sieves)

Diphenylmethane (Penta International, 99+% distilled grade)

Phenol (Dow Chemical 99+%), ~100 ppm $H_2O$+100 ppm impurities

Sodium 3-mercaptopropanesulfonate: Source A: 90% purity (Aldrich)

Source B: 90% purity (Raschig Corp.)

3-Mercaptopropanesulfonic acid (MPSA):

Source A: Prepared from 90% Aldrich sodium 3-mercaptopropanesulfonate by reaction with HCl or treatment in an ion-exchange column Source B: Prepared from 90% Raschig Corp. sodium 3-mercaptopropanesulfonate Sodium 2-mercaptoethanesulfonate: 98% (Aldrich)

4-Mercaptobutanesulfonic acid (MBSA): prepared from 1,4-butanesultone (Aldrich) by reaction with NaSH, Ba(SH)$_2$ or an alkali metal thioacetate in accordance with R. Fischer, supra, A. Mustafa, supra, or *Chem. Abs.*, 90:86742m (1979).

2-Benzyl-4-mercaptobutanesulfonic acid: prepared from 1,4-butanesultone (Aldrich) and benzyl bromide in accordance with M. B. Smith et al., "Lithium Aluminum Hydride-Aluminum Hydride Reduction of Sultones," *J. Org. Chem.*, vol. 46 (1981), pages 101–106 or T. Durst et al., "Metallation of 5- and 6-membered ring sultones," *Can. J. Chem.*, vol. 47 (1969), pages 1230–1233.

2,3-Dimercaptopropanesulfonic acid: prepared from sodium 2,3-dimercaptopropanesulfonate (Aldrich, 95%) by neutralization with HCl or treatment with an acid ion-exchange resin, e.g. DOWEX™ MSC-1.

2,2-Bis(mercaptomethyl)-1,3-propanedisulfonic acid: prepared from 2,2-bis(bromomethyl)-1,3-propanediol (Aldrich, 98%) as follows:

A mixture of 2,2-bis-(bromomethyl)-1,3-propanedisulfonic acid (200.0 g, 0.764 mol, 1.00 equivalent) and sodium sulfite (211.7 g, 1.68 mol, 2.20 equivalents) in 500 mL of deionized water is allowed to react under reflux (about 108° C.) for 28 h. At this time, additional sodium sulfite (105.9 g, 0.840 mol, 1.10 equivalent) is added and the mixture is allowed to react for 3 additional days under reflux. At this point, the mixture consists of a clear solution and a considerable amount of solids.

The mixture is cooled to room temperature and saturated with gaseous hydrogen chloride. An exotherm to 43° C. is observed. The mixture becomes homogenous and yellow in color during the early stages of HCl addition. As the mixture becomes saturated with HCl, a voluminous white precipitate is formed. The solution is cooled to room temperature and filtered to remove solid salts, which are primarily sodium chloride and sodium bromide. Water is removed from the filtrate to provide 2,2-bis-(hydroxymethyl)-1,3-propanedisulfonic acid (190.7 g) as a highly viscous amber oil (glass).

Alternatively, the reaction mixture can be worked up by dilution with about 200 mL of ethanol or methanol, after which the solid is removed by filtration. Solvent is removed from the filtrate on a rotary evaporator, to produce a white solid containing mainly disodium 2,2-bis-(hydroxymethyl)-1,3-propanedisulfonate. Concentrated hydrochloric acid can be added to the solid product to give the soluble disulfonic acid, plus insoluble sodium chloride and sodium bromide.

p-Xylene (400 mL) is added to the 2,2-bis-(hydroxymethyl)-1,3-propanedisulfonic acid and the resulting two-phase mixture is heated under reflux (about 135–150° C. pot temperature) to remove water, produced by the dehydration, in the form of an azeotrope in a Dean-Stark trap. After 8 hours' heating under reflux, the mixture is allowed to cool to room temperature and the upper xylene phase is decanted from the lower viscous product phase. Water (about 300 mL) is added to the cooled, lower phase containing 2,2-bis-(hydroxymethyl)-1,3-propanedisulfonic acid bis-sultone to produce a large mass of white solid. The white solid (bis-sultone) is removed by filtration, slurry washed extensively with water and with methanol and dried in a vacuum oven To a solution of sodium bicarbonate (9.6 g, 114 mmol, 2.6 equivalents) in 30 mL of water is slowly added thiolacetic acid (7.5 g, 96 mmol, 2.2 equivalents). The resulting solution of sodium thiolacetate is added to a solution of 2,2-bis-(hydroxymethyl)-1,3-propanedisulfonic acid bis-sultone (10 g, 43.8 mmol, 1.00 equivalent) in 280 g of acetonitrile. After all the thiolacetate is added, the resulting mixture is allowed to stand overnight at ambient temperature. Solvent is removed using a rotary evaporator to give 19.6 g of ring-opened bis-(thioacetate) adduct as a tan, flaky solid.

The thioacetate adduct (18.2 g) is hydrolyzed by stirring overnight at ambient temperature in a nitrogen-saturated mixture of 10% sodium hydroxide (20 g) and 100 g of water. The mixture is acidified to pH 3 with 10% aqueous hydrochloric acid solution. Solvent is removed from the resulting mixture in a fume hood, using a rotary evaporator. The residue is dissolved in 50 mL of water and saturated with hydrogen chloride gas. The resulting solid salt is removed by filtration and the filtrate is concentrated using a rotary evaporator to give 2,2-bis-(mercaptomethyl)-1,3-propanedisulfonic acid as a viscous dark-colored oil.

Alternatively, the thioacetate adduct can be hydrolyzed by stirring with concentrated hydrochloric acid, removing the solid salt product by filtration and removing water from the filtrate using a rotary evaporator.

ABBREVIATIONS nm=nanometers uv=ultraviolet rpm=revolutions per minute mmol=millimoles HPLC=high pressure liquid chromatography BHPF=9,9-bis-(4-hydroxyphenyl)fluorene=4,4-isomer=BF MPSA=3-mercaptopropanesulfonic acid MBSA=4-mercaptobutanesulfonic acid FN=Fn=9-fluorenone 2,4-isomer=9-(2-hydroxyphenyl)-9-(4-hydroxyphenyl) fluorene DPM=diphenylmethane BPA=2,2-bis-(4-hydroxyphenyl)propane=bisphenol A n/d=not determined

EXAMPLE 1

CONDENSATION OF 9-FLUORENONE WITH PHENOL: (3-MERCAPTO-PROPANESULFONIC ACID)

9-Fluorenone (20.0 g, 0.111 mol, 1.0 equiv.) and molten phenol (156.7 g, 1.66 mol, 15.0 equivalents) are added to a 500 mL PFA Teflon reactor (reactor design 1).

The reaction mixture is heated to 65° C. with stirring at 300–350 rpm under a pad of nitrogen. 3-Mercaptopropanesulfonic acid (0.864 g, 5.53 mmol, 0.0498 equivalents) is added slowly over approximately 1 minute to the reaction mixture at 65° C. The mixture turns dark yellow-orange upon adding the catalyst and gradually fades to a lighter yellow color as the reaction progresses. A slight exotherm to 66° C. is observed. The exotherm persists for 10 minutes before the mixture cools to the reaction temperature of 65° C. The reaction is monitored throughout the reaction period by collecting samples and analyzing by HPLC (Analytical method 1).

The 9-fluorenone is found to be completely consumed within 120 minutes with a product composition, determined by quantitative HPLC, of 98% of 9,9-bis-(4-hydroxyphenyl)-fluorene. The product is further analyzed by a combination of HPLC and UV (282 nm) and contains:

| % by area | product |
| --- | --- |
| 96.9 | 9,9-bis-(4-hydroxyphenyl)fluorene (BHPF) |
| 2.4 | 9-(2-hydroxyphenyl)-9-(4-hydroxyphenyl)-fluorene (2,4-isomer) |
| 0.7 | adduct containing two fluorene units and three phenolic units (two:three adduct) |

EXAMPLE 2

GENERATION OF 3-MERCAPTOALKANESULFONIC ACIDS FROM THEIR SODIUM SALTS IN THE REACTION MIXTURE

A. The procedure of Example 1 is repeated except that the catalyst is prepared in situ from 90 percent sodium 3-mercaptopropanesulfonate (0.854 g, 4.79 mmol, 0.0431 equivalents) and 95–98 percent sulfuric acid (0.48 g, 4.9 mmol, 0.044 equivalents) and the reaction is conducted at 85° C.

The 9-fluorenone is completely consumed between 60 and 120 minutes, giving a final isomer distribution, determined as in Example 1, of:

| % by area | product |
| --- | --- |
| 95.3 | 4,4-isomer (BHPF) |
| 3.6 | 2,4-isomer |
| 1.1 | two-three adduct |

B. The procedure of Example 2A is repeated except that 98 percent sodium 2-mercaptoethanesulfonate (0.779 g, 4.75 mmol, 0.0427 equivalents) and 95–98 percent sulfuric acid (0.48 g, 4.9 mmol, 0.044 equivalents) are used as catalysts. The reaction is conducted at 85° C.

The 9-fluorenone is completely consumed within 60 minutes, giving a product isomer distribution, as described in Example 2A, of:

| % by area | product |
|---|---|
| 91.7 | 4,4-isomer |
| 6.6 | 2,4-isomer |
| 1.7 | two:three adduct |

These experiments demonstrate that 2-mercaptoethanesulfonic acid, generated in the reaction mixture, is an effective condensing agent for the process.

EXAMPLE 3

CONDENSATION USING SULFURIC ACID AND 3-MERCAPTOPROPIONIC ACID (COMPARATIVE EXAMPLE)

9-Fluorenone (20.0 g, 0.111 mol, 1.0 equiv.) and molten phenol (156.7 g, 1.66 mol, 15.0 equiv.) are added to the reactor (reactor design 1). The reaction mixture is heated to 65° C. with stirring a pad of nitrogen. 3-Mercaptopropionic acid (0.588 g, 5.54 mmol, 0.0499 equiv.) is added to the reaction mixture at 65° C., followed by the slow addition (over 1 minute) of concentrated (95–98%) sulfuric acid (0.551 g, 5.62 mmol, 0.0506 equiv.) to the reaction mixture at 65° C. The mixture turns purplish-orange upon adding the sulfuric acid and gradually fades to a yellow-orange color within 5–10 minutes. A slight exotherm to 66–67° C., is observed.

The exotherm persists for 15 minutes before the reaction mixture cools to the reaction temperature of 65° C. The reaction is monitored throughout the reaction period by collecting samples and analyzing by HPLC. The 9-fluorenone is found to be completely consumed between 240 and 420 minutes. HPLC analysis (analytical method 3) gives product distribution:

| % by area | product |
|---|---|
| 93.0 | 9,9-bis-(4-hydroxyphenyl)fluorene |
| 5.5 | 2,4-isomer |
| 1.5 | two:three adduct |

This example shows that the prior art process is slower than the process of Examples 1 or 2 and that the resulting product contains less of the 4,4-isomer, than produced by the process of Examples 1 or 2.

EXAMPLE 4

EFFECT OF ADDED WATER IN FLUORENONE PHENOLATIONS USING MPSA (PHENOL AS SOLVENT)

A. 9-Fluorenone (138.1 g, 0.770 mol, 1.00 equiv.) and molten phenol (1500 g, 15.9 mol, 20.8 equiv.) is added to the reactor (reactor design 4, 2 L). The reaction mixture is heated to 45° C. with stirring under a pad of nitrogen. 3-Mercaptopropanesulfonic acid (8.28 g, 53.0 mmol, 0.0692 equiv.) is added slowly over approximately 1 minute to the reaction mixture at 45° C. The reaction is monitored throughout the reaction period by collecting samples and analyzing by HPLC. The 9-fluorenone is found to be 22% consumed within 9 minutes, 52% consumed within 30 minutes, 76% consumed within 1 hour, 92% consumed within 1.75 hours, and 100% consumed within 3.5 hours. HPLC analysis (analytical method 3) gives the following relative area % analysis for the reaction products at 100% conversion:

| % by area | product |
|---|---|
| 96.9 | 9,9-bis(4-hydroxyphenyl)fluorene |
| 2.4 | 2,4-isomer |
| 0.6 | two:three adduct |

B. 9-Fluorenone (6.44 g, 0.0358 mol, 1.00 equiv.), molten phenol (70.0 g, 0.744 mol, 20.8 equiv.), and deionized water (1.93 g, 0.107 mol, 3.00 equiv.) is added to the reactor (reactor design 3). The reaction mixture is heated to 45° C. with stirring under a pad of nitrogen. 3-Mercaptopropanesulfonic acid (0.385 g, 2.47 mmol, 0.0690 equiv.) is added slowly over approximately 1 minute to the reaction mixture at 45° C. The reaction is monitored throughout the reaction period by collecting samples and analyzing by HPLC. The 9-fluorenone is found to be 4% consumed within 9 minutes, 13% consumed within 1 hour, 29% consumed within 3.5 hours, and 94% consumed within 20.5 hours. HPLC analysis (analytical method 3) gives the following relative area % analysis for the reaction products (fluorenone area not included) at 94% conversion:

| % by area | product |
|---|---|
| 96.5 | BHPF (4,4-isomer) |
| 2.9 | 2,4-isomer |
| 0.6 | two:three adduct |

These experiments show that higher reaction rates and lower amounts of undesirable by-products are obtained, in the absence of additional water.

EXAMPLE 5

CONDENSATION OF FLUORENONE WITH PHENOL USING OTHER CONDENSING AGENTS

A. 4-MERCAPTOBUTANESULFONIC ACID

9-Fluorenone (82.9 g, 0.460 mol, 1.00 equiv.) and molten phenol (900 g, 9.56 mol, 20.8 equiv.) is added to the reactor (reactor design 4, 2 L). The reaction mixture is heated to 45° C. with stirring under a pad of nitrogen. 4-Mercaptobutanesulfonic acid (5.41 g, 31.8 mmol, 0.0692 equiv.) is added slowly over approximately 1 minute to the reaction mixture at 45° C. The reaction is monitored throughout the reaction period by collecting samples and analyzing by HPLC. The 9-fluorenone is found to be 17% consumed within 5.5 minutes, 58% consumed within 30 minutes, 83% consumed within 1 hour, 95% consumed within 1.75 hours, and 100% consumed within 3.5 hours. HPLC analysis (analytical method 3) gives the following relative area % analysis for the reaction products at 100% conversion:

| % by area | product |
|---|---|
| 97.0 | BHPF |
| 2.5 | 2,4-isomer |
| 0.5 | two:three adduct |

B. 2,2-BIS-(MERCAPTOMETHYL)-1,3-PROPANEDISULFONIC ACID

To a 4 dram vial (reactor design 2) is added a mixture of fluorenone (0.40 g, 2.22 mmol, 1.00 equiv.) and phenol (2.10 g, 22.3 mmol, 10.0 equiv.) The capped vial is placed into the heating control block regulated at 63° C. and stirring is begun.

2,2-Bis(mercaptomethyl)-1,3-propanedisulfonic acid (0.029 g, 0.098 mmol, 0.044 equiv.) is added in one portion to the vial which is then tightly capped. The reaction is monitored throughout the reaction period by collecting samples and analyzing by HPLC. The 9-fluorenone is found to be 25% consumed in 1.5 hours. HPLC analysis (analytical method 2) gives the following relative area % analysis for the reaction products (fluorenone area not included) at 25% conversion:

| % by area | product |
|---|---|
| 95.7 | BHPF |
| 3.4 | 2,4-isomer |
| 0.9 | two:three adduct |

C. 2,3-DIMERCAPTOPROPANESULFONIC ACID

To a 4 dram vial (reactor design 2) is added a mixture of fluorenone (0.40 g, 2.22 mmol, 1.00 equiv.) and phenol (2.10 g, 22.3 mmol, 10.0 equiv.) The capped vial is placed into the heating control block regulated at 63° C. and stirring is begun. 2,3-Dimercaptopropanesulfonic acid (0.021 g, 0.011 mmol, 0.050 equiv.) is added in one portion to the vial which is then tightly capped. The reaction is monitored throughout the reaction period by collecting samples and analyzing by HPLC (analytical method 2). The 9-fluorenone is found to be 5% consumed in 1.5 hours.

D. 3-MERCAPTOPROPIONIC ACID AND METHANE-SULFONIC ACID (COMPARATIVE EXAMPLE)

To a 4 dram vial (reactor design 2) is added a mixture of fluorenone (0.460 g, 2.55 mmol, 1.00 equiv.) and phenol (5.00 g, 53.1 mmol, 20.8 equiv.) The capped vial is placed into the heating control block regulated at 55° C. and stirring is begun. 3-Mercaptopropionic acid (0.0217 g, 0.204 mmol, 0.080 equiv.) and methanesulfonic acid (0.0197 g, 0.205 mmol, 0.080 equiv.) are added in one portion to the vial which is then tightly capped. The reaction is monitored throughout the reaction period by collecting samples and analyzing by HPLC. The 9-fluorenone is found to be 32% consumed within 30 minutes, 51% consumed within 1 hour, and 71% consumed within 2 hours. HPLC analysis (analytical method 3) gives the following relative area % analysis for the reaction products (fluorenone area not included) at 71% conversion:

| % by area | product |
|---|---|
| 93.7 | BHPF |
| 5.5 | 2,4-isomer |
| 0.8 | two:three adduct |

E. 3-MERCAPTOPROPIONIC ACID AND METHYL-SULFAMIC ACID (COMPARATIVE EXAMPLE)

To a 4 dram vial (reactor design 2) is added a mixture of fluorenone (0.460 g, 2.55 mmol, 1.00 equiv.) and phenol (5.00 g, 53.1 mmol, 20.8 equiv.) The capped vial is placed into the heating control block regulated at 55° C. and stirring is begun. 3-Mercaptopropionic acid (0.0217 g, 0.204 mmol, 0.080 equiv.) and methylsulfamic acid (Aldrich 98%) (0.0227 g, 0.204 mmol, 0.080 equiv.) are added in one portion to the vial which is then tightly capped. The reaction is monitored throughout the reaction period by collecting samples and analyzing by HPLC. The 9-fluorenone is found to be 13% consumed within 1 hour, and 21% consumed within 2 hours. HPLC analysis (analytical method 3) gives the following relative area % analysis for the reaction products (fluorenone area not included) at 21% conversion:

| % by area | product |
|---|---|
| 95.4 | BHPF |
| 4.6 | 2,4-isomer |
| n/d | two:three adduct |

F. SUBSTITUTION OF PHOSPHONIC ACIDS FOR METHANESULFONIC ACID (COMPARATIVE EXAMPLES)

The reaction conditions described in Example 5D are repeated substituting each of the following acids (each at 8 mol %) for methanesulfonic acid in the reaction: sulfamic acid (Aldrich 98%), methylphosphonic acid (Aldrich 98%), and phenylphosphonic acid (Aldrich 98%). In each case, very little conversion of the fluorenone is observed in comparison with the use of methanesulfonic acid.

These examples demonstrate that mixtures of a mercapto-compound and an acid are inferior to 3-mercaptopropane-sulfonic or 4-mercaptobutanesulfonic acid for catalyzing the condensation of phenol with fluorenone.

EXAMPLE 6

EFFECT OF WATER CONCENTRATION IN FLUORENONE PHENOLATIONS USING MPSA WITH DIPHENYLMETHANE AS A CO-SOLVENT

A. 9-Fluorenone (3.65 g, 0.0200 mol, 1.00 equiv.), molten phenol (39.6 g, 0.420 mol, 20.8 equiv.), deionized water (0.055 g, 3.06 mmol, 0.151 equiv.) and diphenylmethane (32.83 g) is added to the reactor (reactor design 2). The reaction mixture is heated to 53° C. with stirring under a pad of nitrogen. 3-Mercaptopropanesulfonic acid (0.170 g, 1.10 mmol, 0.0537 equiv.) is added slowly over approximately 1 minute to the reaction mixture at 53° C. The reaction is monitored throughout the reaction period by collecting samples and analyzing by HPLC. The 9-fluorenone is found to be 49% consumed within 2 hours and 77% consumed within 4.5 hours. HPLC analysis (analytical method 3) gives the following relative area % analysis for the reaction products (fluorenone area not included) at 77% conversion:

| % by area | product |
|---|---|
| 96.1 | BHPF |
| 3.4 | 2,4-isomer |
| 0.5 | two:three adduct |

B. 9-Fluorenone (3.65 g, 0.020 mol, 1.0 equiv.), molten phenol (39.6 g, 0.420 mol, 20.8 equiv.), deionized water (0.362 g, 20.1 mmol, 0.994 equiv.) and diphenylmethane (32.83 g) is added to the reactor (reactor design 2). The reaction mixture is heated to 53° C. with stirring under a pad of nitrogen.

3-Mercaptopropanesulfonic acid (0.158 g, 1.00 mmol, 0.0500 equiv.) is added slowly over approximately 1 minute to the reaction mixture at 53° C. The reaction is monitored throughout the reaction period by collecting samples and analyzing by HPLC. The 9-fluorenone is found to be 25% consumed within 2 hours, 45% consumed within 4.5 hours, and 57% consumed within 6 hours. HPLC analysis (analytical method 3) gives the following relative area % analysis for the reaction products (fluorenone area not included) at 57% conversion:

| % by area | product |
|---|---|
| 96.3 | BHPF |
| 3.7 | 2,4-isomer |
| n/d | two:three adduct |

C. 9-Fluorenone (3.65 g, 0.0200 mol, 1.00 equiv.), molten phenol (39.6 g, 0.420 mol, 20.8 equiv.), deionized water (1.09 g, 60.7 mmol, 3.00 equiv.) and diphenylmethane (32.83 g) is added to the reactor (reactor design 2). The reaction mixture is heated to 53° C. with stirring under a pad of nitrogen. 3-Mercaptopropanesulfonic acid (0.158 g, 1.00 mmol, 0.0500 equiv.) is added slowly over approximately 1 minute to the reaction mixture at 53° C. The reaction is monitored throughout the reaction period by collecting samples and analyzing by HPLC. The 9-fluorenone is found to be 11% consumed within 2 hours, 20% consumed within 4.5 hours, and 23% consumed within 6 hours. HPLC analysis (analytical method 3) gives the following relative area % analysis for the reaction products (fluorenone area not included) at 23% conversion:

| % by area | product |
|---|---|
| 95.9 | BHPF |
| 4.1 | 2,4-isomer |
| n/d | two:three adduct |

These examples show that addition of large amounts of water to the reaction mixtures retards the condensation reaction.

EXAMPLE 7

REMOVAL OF WATER UNDER VACUUM WITH AND WITHOUT DIPHENYLMETHANE AS A CO-SOLVENT

A. 9-Fluorenone (127.7 g, 0.709 mol, 1.00 equiv.) and molten phenol (996.1 g, 10.58 mol, 14.9 equiv.) is added to the reactor (reactor design 4, 3 L). The reaction mixture is heated to 45° C. with stirring under a pad of nitrogen. 3-Mercapto-propanesulfonic acid (5.53 g, 35.4 mmol, 0.0500 equiv.) is added slowly over approximately 1 minute to the reaction mixture at 45° C. The reaction is monitored throughout the reaction period by collecting samples and analyzing by HPLC. The 9-fluorenone is found to be 60% consumed within 1 hour, 88% consumed within 2 hours, and 95% consumed within 2.5 hours. HPLC analysis (analytical method 2) gives the following relative area % analysis for the reaction products at 100% conversion:

| % by area | product |
|---|---|
| 98.0 | BHPF |
| 1.4 | 2,4-isomer |
| 0.7 | two:three adduct |

B. 9-Fluorenone (127.7 g, 0.709 mol, 1.00 equiv.) and molten phenol (996.4 g, 10.59 mol, 14.9 equiv.) is added to the reactor (reactor design 4, 3 L with a Dean-Stark water separation trap and vacuum inlet attached in lieu of the nitrogen inlet). The reaction mixture is heated to 45° C. with stirring. 3-Mercaptopropanesulfonic acid (5.53 g, 35.4 mmol, 0.0500 equiv.) is added slowly over approximately 1 minute to the reaction mixture at 45° C. The reaction mixture is allowed to stir for 15 minutes at atmospheric pressure, then vacuum is applied to the reactor. From this point on, the reaction is conducted under reduced pressure conditions (<5 mm Hg) with water/phenol distillate collected in the Dean-Stark trap. The reaction is monitored throughout the reaction period by collecting samples and analyzing by HPLC. The 9-fluorenone is found to be 68% consumed within 1 hour, 98% consumed within 2 hours, and 100% consumed within 2.5 hours. HPLC analysis (analytical method 2) gives the following relative area % analysis for the reaction products at 100% conversion:

| % by area | product |
|---|---|
| 98.1 | BHPF |
| 1.3 | 2,4-isomer |
| 0.6 | two:three adduct |

C. 9-Fluorenone (191.5 g, 1.063 mol, 1.00 equiv.), molten phenol (1500 g, 15.9 mol, 15.0 equiv.) and diphenylmethane (156.7 g) are added to the reactor (reactor design 4, 3 L with a Dean-Stark water separation trap and vacuum inlet attached in lieu of the nitrogen inlet). The reaction mixture is heated to 45° C. with stirring. 3-Mercaptopropanesulfonic acid (8.27 g, 53.0 mmol, 0.0499 equiv.) is added slowly over approximately 1 minute to the reaction mixture at 45° C. The reaction mixture is allowed to stir for 15 minutes at atmospheric pressure, then vacuum is applied to the reactor. From this point on, the reaction is conducted under reduced pressure conditions (<5 mm Hg) with water/phenol distillate collected in the Dean-Stark trap. The reaction is monitored throughout the reaction period by collecting samples and analyzing by HPLC. The 9-fluorenone is found to be 20% consumed within 15 minutes, 80% consumed within 2 hours, 98% consumed within 3.5 hours, and 100% consumed within 6 hours. HPLC analysis (analytical method 2) gives the following relative area % analysis for the reaction products at 100% conversion:

| % by area | product |
|---|---|
| 98.3 | BHPF |
| 1.2 | 2,4-isomer |
| 0.5 | two:three adduct |

These results show that removal of water from the reaction mixtures, containing diphenylmethane solvent, is unnecessary. These results show that removing water from the reaction mixtures accelerates the rate of the phenolation reaction, but is not necessary for good reaction rates and conversions.

EXAMPLE 8

REACTION OF PHENOL WITH ACETONE TO PRODUCE BISPHENOL A USING MPSA CATALYST

A. To a 4 dram vial (reactor design 2) is added a mixture of acetone (0.11 g, 1.8 mmol, 1.0 equiv.) and phenol (2.40 g, 25.5 mmol, 14.0 equiv.). The capped vial is placed into the heating control block regulated at 62° C. and stirring is begun. 3-Mercaptopropanesulfonic acid (0.021 g, 0.13 mmol, 0.070 equiv.) is added in one portion to the vial which is then tightly capped. The reaction is monitored throughout the reaction period by collecting samples and analyzing by HPLC. The acetone is found to be approximately 70% consumed within 2 hours. HPLC analysis (analytical method 2) gives a relative area % ratio of 97.0:3.0 for the desired reaction product 2,2-bis-(4-hydroxyphenyl)propane (4,4-bisphenol A) relative to the isomeric impurity 2-(2-hydroxyphenyl)-2-(4-hydroxyphenyl)-propane (2,4-bisphenol A) at 70% conversion.

B. To a 4 dram vial (reactor design 2) is added a mixture of acetone (0.11 g, 1.8 mmol, 1.0 equiv.) and phenol (2.40 g, 25.5 mmol, 14.0 equiv.). The capped vial is placed into the heating control block regulated at 25° C. and stirring is begun. 3-Mercaptopropanesulfonic acid (0.074 g, 0.47 mmol, 0.25 equiv.) is added in one portion to the vial which is then tightly capped. The reaction is monitored throughout the reaction period by collecting samples and analyzing by HPLC. The acetone is found to be approximately 70% consumed within 2 hours. During the later stages of reaction, the reaction product begins to crystallize from the reaction mixture. HPLC analysis (analytical method 2) gives a relative area % ratio of 98.9:1.1 for the desired reaction product 2,2-bis-(4-hydroxy-phenyl)propane (4,4-bisphenol A) relative to the isomeric impurity 2-(2-hydroxyphenyl)-2-(4-hydroxyphenyl)propane (2,4-bisphenol A) for the bulk reaction solution.

Separation of the crystalline product from the reaction mixture followed by rinsing of the crystals with water to remove surface impurities provides 4,4-bisphenol A product containing less than 500 parts per million of the 2,4-bisphenol A impurity.

C. (Comparative Example) To a 4 dram vial (reactor design 2) is added a mixture of acetone (0.11 g, 1.8 mmol, 1.0 equiv.) and phenol (2.40 g, 25.5 mmol, 14.0 equiv.). The capped vial is placed into the heating control block regulated at 62° C. and stirring is begun. 3-Mercaptopropionic acid (0.014 g, 0.13 mmol, 0.070 equiv.) and methanesulfonic acid (0.013 g, 0.13 mmol, 0.070 equiv.) are added in one portion to the vial which is then tightly capped. The reaction is monitored throughout the reaction period by collecting samples and analyzing by HPLC. The acetone is found to be approximately 70% consumed within 2 hours. HPLC analysis (analytical method 2) gives a relative area % ratio of 96.2:3.8 for the desired reaction product 2,2-bis-(4-hydroxyphenyl)propane (4,4-bisphenol A) relative to the isomeric impurity 2-(2-hydroxyphenyl)-2-(4-hydroxyphenyl)propane (2,4-bisphenol A) at 70% conversion.

These experiments show that MPSA gives a product, with a higher 4,4-isomer ratio than prior art catalysts.

EXAMPLE 9

PREPARATION OF THE POLYMER-SUPPORTED MERCAPTOSULFONIC ACID CATALYST (PMBSA)

A. PREPARATION OF SULTONE INTERMEDIATE 1,4-Butanesultone (3.00 g, 22.0 mmol, 1.00 equivalent) is added to dry THF (150 mL) under a nitrogen atmosphere. The solution is cooled to −78° C. using a dry ice/acetone bath. n-Butyllithium (1.6 molar in hexanes, 13.8 mL, 1.00 equivalent) is added slowly dropwise to the −78° C. solution via an addition funnel over approximately 40 minutes with vigorous stirring. The homogeneous reaction mixture is allowed to stir for an additional 10–15 minutes at −78° C. Poly(vinylbenzylchloride) (3.3 g, approximately 1.0 equivalent of chloromethyl groups, 60/40 mixture of 3- and 4-isomers, Aldrich Chemical Co.) in dry THF (10 mL) is added over approximately 2 minutes to the reaction mixture at −78° C. The reaction mixture is allowed to slowly warm to room temperature in the cooling bath over approximately 3 hours. A white precipitate forms in the reaction mixture during the reaction period and remains as a solid as the mixture reaches room temperature. Water (100 mL) is added to the reaction mixture and the white (insoluble) solid is removed by filtration under vacuum. The solid is slurry-washed with water, then with small volumes of methanol and methylene chloride and dried in a vacuum oven, providing 4.77 g of a white solid sultone-functional polymer.

B. CONVERSION OF THE SULTONE-FUNCTIONAL POLYMER TO POLYMER-SUPPORTED MERCAPTOSULFONIC ACID (PMBSA)

The sultone-functional polymer from above (4.00 g, approximately 15.9 mmol sultone) is added to THF (125 mL). Potassium thioacetate (2.20 g, 19.0 mmol, 1.20 equivalent) is added as a solid to the slurry of the polysultone in THF. One drop of 50% tetrabutylammonium chloride is added to the rapidly stirred slurry. The temperature rises to 26° C. over several minutes, then slowly drops to 20° C. Two additional drops of 50% tetrabutylammonium chloride are added and the solution is warmed to 40° C. for 15 minutes. Water (100 mL) is slowly added over 1 hour to the reaction mixture at 40° C. Substantial solid remains in the mixture at all stages of the reaction. The water/THF reaction mixture is allowed to react 15 hours at 40° C. The solvent is removed by rotary evaporation and the resultant solid is ground to a fine powder. THF (125 mL) is again added to the solid, forming a slurry. Additional potassium thioacetate (2.20 g, 19.0 mmol, 1.20 equivalent) is added, resulting in an exotherm to 26° C. Several drops of 50% tetrabutylammonium chloride are added and the reaction mixture is heated to 40° C. for 15 hours. The solvent is removed by rotary evaporation. The tan solid is slurried in a 2:1 (by volume) mixture of toluene/ethanol. Concentrated hydrochloric acid (50 mL) is added and the mixture is stirred at room temperature overnight. Most of the HCl is removed by sparging the mixture with nitrogen, then the solvents are removed by rotoevaporation. The light tan solid is slurry-washed extensively with 10% hydrochloric acid and with water. Drying overnight in a vacuum oven (60° C./full vacuum) provides 4.18 g of the polymer-supported mercapto-sulfonic acid as a light tan solid.

C. PREPARATION OF A GEL PMBSA CATALYST (PMBSA-MER)

A catalyst is prepared as above, starting with Merrifield resin (200–400, 2% crosslinked, gel), treated with butane-sultone. The product is identified as PMBSA-MER.

D. PREPARATION OF CATALYST FROM BROMOMETHYLATED MACROPOROUS POLYSTYRENE (PMBSA-XEBR)

A catalyst is prepared as above, starting with bromomethylated Amberlite™ XE-305 macroporous resin (4% crosslinked, 20–50 mesh, about 3.7 meq Br/g).

E. PREPARATION OF CATALYST FROM CHLOROMETHYLATED MACROPOROUS POLYSTYRENE (PMBSA-XECL)

A catalyst is prepared as above, starting with chloromethylated Amberlite™ macroporous resin (4% crosslinked, 20–50 mesh, about 4.3 meq Cl/g).

F. PREPARATION OF CATALYST FROM MERRIFIELD RESIN AND 1,3-PROPANESULTONE (PMPSA-MER)

Catalyst is prepared above, by treating Merrifield resin (2% crosslinked, 200–400 mesh, 4.3 meq Cl/g) with lithiated 1,3-propanesultone, which can be prepared in accordance with T. Durst et a.,. "A new route to 5- and 6-membered ring sultones," *Can. J. Chem.*, vol. 48 (1970), pages 845–851.

EXAMPLE 10

EVALUATION OF A MERCAPTOSULFONIC ACID POLYMER (PMBSA) IN THE REACTION OF PHENOL WITH FLUORENONE

A. To a 4 dram vial equipped with a stirring bar (reactor design 2) is added 4.33 grams of a 20.8:1 mole ratio mixture of phenol to fluorenone and 0.26 g (6% by weight of the reactant solution) of the mercaptosulfonic acid polymer (PMBSA) prepared as in Example 9B. The reaction mixture consists of a homogeneous liquid phase plus a separate heterogeneous polymer catalyst phase. The mixture is heated to 36° C. for 3 hours. To increase the rate of reaction the temperature is increased to 50° C. for 18 hours. Monitoring of the reaction by HPLC shows some reaction at 36° C. and 100% conversion after 18 hours at 50° C. HPLC analysis (analytical method 2) gives the following relative area % analysis for the products after 18 hours of reaction (100% conversion):

| % by area | product |
|---|---|
| 98.86 | BHPF |
| 0.98 | 2,4-isomer |
| 0.16 | two:three adduct |

B. (Comparative Example) Dowex™ 50WX4 (a crosslinked sulfonated polystyrene resin, The Dow Chemical Company) promoted with 2,2-dimethylthiazolidine (25% of the resin sulfonic acid equivalents) is washed on a glass filter frit with phenol at 55° C. to remove water. The resin is then washed with a mixture consisting of a 20.8:1 mole ratio mixture of phenol to fluorenone at 55° C. to displace the original phenol wash. To a 4 dram vial equipped with a stirring bar (reactor design 2) is added 2.13 grams of a 20.8:1 mole ratio mixture of phenol to fluorenone and 0.74 g (35% by weight of the reactant solution) of the promoted Dowex™ 50WX4 catalyst activated as described above. The weight of catalyst used is determined after the reaction by recovery of the resin from the reaction mixture by filtration, washing the resin with toluene and hexane, and drying to a constant weight in a vacuum oven at 50° C. for 6 hours.

The reaction mixture consists of a homogeneous liquid phase plus a separate heterogeneous polymer catalyst phase. The mixture is heated to 50° C. for 18 hours. Monitoring of the reaction by HPLC shows approximately 17% conversion after 4 hours and 73% conversion after 18 hours at 50° C. HPLC analysis (analytical method 2) gives the following relative area % analysis for the products after 18 hours of reaction (73% conversion):

| % by area | product |
|---|---|
| 91.32 | BHPF |
| 6.78 | 2,4-isomer |
| 1.90 | two:three adduct |

C. (Comparative Example) To a 4 dram vial equipped with a stirring bar (reactor design 2) is added 2.16 grams of a 20.8:1 mole ratio mixture of phenol to fluorenone and 0.34 g (16% by weight of the reactant solution) of dry Amberlyst™ 15 (a crosslinked sulfonated polystyrene resin available from Rohm and Haas Company). The reaction mixture consists of a homogeneous liquid phase plus a separate heterogeneous polymer catalyst phase. The mixture is heated to 50° C. for 18 hours. Monitoring of the reaction by HPLC shows approximately 24% conversion after 4 hours and 64% conversion after 18 hours at 50° C. HPLC analysis (analytical method 2) gives the following relative area % analysis for the products after 18 hours of reaction (64% conversion):

| % by area | product |
|---|---|
| 95.82 | BHPF |
| 3.93 | 2,4-isomer |
| 0.25 | two:three adduct |

These experiments show that use of the catalysts disclosed herein gives higher conversions of fluorenone and higher 4,4/2,4-isomer ratios than the prior art catalysts.

EXAMPLE 11

RECOVERY AND RECYCLING OF SOLID CATALYST (PMBSA)

A. CATALYST RECOVERY

The reaction mixture from Example 10A is cooled to 40° C. and the mixture is centrifuged. The upper liquid layer is decanted and additional warm (40–45° C.) 20.8:1 mole ratio phenol/fluorenone solution (approximately 3–4 times the catalyst volume) is added. The mixture is stirred, centrifuged, and the warm liquid layer is decanted. This wash procedure is repeated for a total of three washes, then the required amount of phenol/fluorenone reactant mixture is added and the reaction is begun.

B. FIRST RECYCLE

To the 4 dram vial containing the mercaptosulfonic acid polymer recovered (as described above) from Example 11A is added 4.33 grams of a 20.8:1 mole ratio mixture of phenol to fluorenone. The mixture is heated to 50° C. for 4 hours. Monitoring of the reaction by HPLC shows approximately 90% conversion after 4 hours at 50° C. HPLC analysis (analytical method 2) gives the following relative area % analysis for the products after 4 hours of reaction (90% conversion):

| % by area | product |
|---|---|
| 98.77 | BHPF |
| 1.09 | 2,4-isomer |
| 0.14 | two:three adduct |

C. SECOND RECYCLE

To the 4 dram vial containing the mercaptosulfonic acid polymer recovered (as described above) from the first recycle is added 4.00 grams of a 20.8:1 mole ratio mixture of phenol to fluorenone. The mixture is heated to 50° C. for 18 hours. Monitoring of the reaction by HPLC shows approximately 83% conversion after 4 hours and 100% conversion after 18 hours at 50° C. HPLC analysis (analytical method 2) gives the following relative area % analysis for the products after 18 hours of reaction (100% conversion):

| % by area | product |
|---|---|
| 98.79 | BHPF |
| 1.10 | 2,4-isomer |
| 0.11 | two:three adduct |

D. THIRD RECYCLE

To the 4 dram vial containing the mercaptosulfonic acid polymer recovered (as described above) from the second recycle is added 2.00 grams of a 20.8:1 mole ratio mixture of phenol to fluorenone. The mixture is heated to 40° C. for 18 hours. Monitoring of the reaction by HPLC shows approximately 90% conversion after 4.5 hours and 100% conversion after 18 hours at 40° C. HPLC analysis (analytical method 2) gives the following relative area % analysis for the products after 18 hours of reaction (100% conversion):

| % of area | product |
|---|---|
| 99.08 | BHPF |
| 0.92 | 2,4-isomer |
| * | two:three adduct |

*not detectable

These experiments show that the catalyst can be recycled repeatedly without loss of activity.

EXAMPLE 12

COMPOSITE EXPERIMENTAL DETERMINATION OF PARAMETERS FOR THE CONDENSATION OF PHENOL WITH FLUORENONE (3-MPSA, DIPHENYL-METHANE)

Experiments are run in stirred isothermal batch reactors (reactor designs 2 or 3) to determine the effect of temperature, molar ratios of reactants and amount of MPSA on reaction rates and product distribution. Results are shown in Table I.

Graphical analysis of the results in Table I shows that formation of 2,4-BHPF is related to the reaction temperature. As the temperature increases, the 2,4/4,4 ratio increases. In contrast, the phenol/Fn mole ratio has little effect on the 2,4/4,4 ratio. The yield of 2:3 adduct increases markedly as the ratio of phenol/Fn decreases from 15:1 to 2.5:1 and the reaction temperatures is increased from 25° C. to 85° C.

Graphical analysis of results for runs at 18 mole % of MPSA, in terms of initial reaction rates (BHPF moles/L*hr) shows a marked rate increase in going from 25° C. to 85° C.

Increasing the concentration of MPSA catalyst also gives the expected increase in the reaction rate. The phenol:fluorenone ratio also affects the reaction rate.

It is believed that higher ratios of phenol to fluorenone are beneficial for condensations, run in a solvent, such as diphenylmethane.

TABLE I

PHENOL + Fn ----> BHPF
Catalyst MPSA, 10% Fn in DPM
Analytical Method 2 - UV Detector

| Run # | Temp. (°C.) | Mole Ratio | Mole % MPSA | 2,4/4,4 Area | 2:3/4,4 Area | Conv. (%) | Initial Rates* |
|---|---|---|---|---|---|---|---|
| 1 | 55 | 8.62 | 12.8 | 0.0261 | 0.0198 | 99 | 0.16 |
| 2 | 25 | 2.46 | 7.9 | | | 14 | 0.0002 |
| 3 | 85 | 2.46 | 7.9 | 0.0389 | 0.114 | 62 | 0.047 |
| 4 | 25 | 14.75 | 7.9 | | | 12 | 0.028 |
| 5 | 85 | 14.75 | 7.9 | 0.0299 | 0.0098 | 99 | 0.53 |
| 6 | 25 | 2.46 | 17.7 | | | 5 | 0.001 |
| 7 | 85 | 2.46 | 17.7 | 0.0334 | 0.102 | 67 | 0.59 |
| 8 | 25 | 14.75 | 17.7 | 0.0202 | 0.0074 | 99 | 0.041 |
| 9 | 85 | 14.75 | 17.7 | 0.0317 | 0.0106 | 99 | 0.88 |
| 10 | 25 | 8.62 | 12.8 | 0.0239 | 0.0179 | 99 | 0.0042 |
| 11 | 85 | 8.62 | 12.8 | 0.0354 | 0.0244 | 99 | 0.73 |
| 12 | 55 | 2.46 | 12.8 | 0.0252 | 0.0673 | 57 | 0.035 |
| 13 | 55 | 14.75 | 12.8 | 0.0237 | 0.0076 | 99 | 0.17 |
| 14 | 55 | 8.62 | 7.9 | 0.0264 | 0.0177 | 99 | 0.12 |
| 15 | 55 | 8.62 | 17.7 | 0.0291 | 0.0248 | 99 | 0.42 |
| 16 | 55 | 8.62 | 12.8 | 0.0285 | 0.0185 | 99 | 0.15 |
| 17 | 63 | 14.75 | 12.8 | 0.026 | 0.00911 | 99 | |
| 18 | 63 | 14.75 | 12.8 | 0.0259 | 0.0088 | 99 | |
| 19 | 63 | 14.75 | 12.8 | 0.026 | 0.0088 | 99 | |
| 20 | 63 | 14.75 | 12.8 | 0.0266 | 0.0084 | 99 | 0.29 |
| 21** | 63 | 14.75 | 12.8 | 0.0272 | 0.0096 | 99 | |
| 22 | 63 | 14.75 | 12.8 | 0.0265 | 0.0098 | 98 | |
| 23 | 63 | 14.75 | 12.8 | 0.0269 | 0.0092 | 98 | |
| 24 | 55 | 14.75 | 17.7 | 0.0255 | 0.0084 | 98 | 0.36 |
| 25 | 55 | 2.46 | 17.7 | — | — | 24 | 0.14 |
| 26 | 63 | 9.9 | 5 | 0.0258 | 0.015 | 98 | 0.078 |
| 27 | 25 | 14.75 | 12.8 | 0.0178 | 0.0067 | 98 | 0.013 |

Footnotes to Table I:
BF = BHPF (4,4-isomer)
2:3 = two:three adduct
*BHPF moles/L hr.
**recycle

TABLE II

PHENOL + Fn ----> BHPF
Catalyst MPSA, Various % Fn in Solvents
Analytical Method 2 - UV Detector

| Run | Temp °C. | Solvent | % Fn* | Mole Ratio | Mole % MPSA | 2,4/4,4 Area | 2:3/4,4 Area | Time hr | % Conv |
|---|---|---|---|---|---|---|---|---|---|
| 1 | 65 | DPM | 21 | 10 | 18 | 0.029 | 0.017 | 2 | 98 |
| 2 | 55 | DPM | 55 | 15 | 6.5 | 0.012 | 0.008 | 4 | 100 |
| 3 | 33 | DPM | 38.4 | 30 | 11.5 | 0.013 | 0.005 | 2.5 | 95 |
| 4 | 45 | DPM | 55 | 20.8 | 14.6 | 0.016 | 0.006 | 2 | 100 |
| 5 | 45 | DPM | 55 | 15 | 5.0 | 0.013 | 0.005 | 6 | 100 |
| 1A | 27 | DPM/MC | 29 | 21 | 4.6 | 0.010 | 0.005 | 19.5 | 100 |
| 2A | 35 | MBenzoate | ~55 | 21 | 8 | 0.015 | 0.004 | 6.5 | 86 |
| 3A | 35 | ClBenzene | 13 | 21 | 25.6 | 0.018 | 0.005 | 3.25 | 99 |
| 4A | 35 | 2,4,6TMPh | 14 | 21 | 14.6 | 0.014 | 0.002 | 3 | 38 |

*In solvent
DPM = diphenylmethane
DPM/MC = diphenylmethane + methylene chloride
MBenzoate = methyl benzoate
ClDenzene = chlorobenzene
2,4,6TMPh = 2,4,6-TrimethylPhenol The results in Table I show that the 2,4/4,4 ratio stays constant as conversion increases, whereas the 2:3/4,4 ratio increases.

The amount of MPSA catalyst is related to the amount of 2,4-isomeric product formed. High 2,4/4,4 ratios at high concentrations of MPSA are probably related to a shift toward an acid-catalyzed reaction to produce relatively higher amounts of 2,4-isomer.

EXAMPLE 13

EFFECTS OF SOLVENTS ON PRODUCT DISTRIBUTION AND CONVERSIONS

Experiments are run in stirred tank batch reactors to determine whether use of a solvent is advantageous. Results of these experiments are shown in Table II. The use of a solvent does not appear to be advantageous. Comparison of a run using 10% DPM with neat run, at the same MPSA concentration, shows that reaction rates are higher for the neat run, although the DPM run uses 2.5 times more catalyst/Fn.

Higher 2,4/4,4 and 2:3-adduct ratios for the reactions in DPM is another disadvantage. It is therefore preferred to run the condensations in excess phenol as solvent.

EXAMPLE 14

EFFECTS OF TEMPERATURE, MPSA CONCENTRATION AND PHENOL/FLUORENONE RATIOS ON PRODUCT DISTRIBUTIONS (EXCESS PHENOL AS SOLVENT)

Reactions are done in isothermal stirred tank reactors as described above. Results are presented in Table III. These results demonstrate that increasing the amount of catalyst increases the 2,4/4,4 isomer ratio. Increasing the reaction temperature or decreasing the phenol/Fn mole ratio leads to higher amounts of 2:3 adduct in the product mixture.

EXAMPLE 15

RECOVERY AND RECYCLING OF MPSA FROM THE REACTION MIXTURES

Runs of 100 mL to 1.5 L (reactor designs 3 and 4) are done to determine whether MPSA can be extracted from the neat BHPF reaction solution with water and recycled to subsequent runs. The effect of stirrer rpm on the time required for breaking a resulting emulsion are also investigated.

Phenol is weighed and charged into the reaction vessel. Fluorenone is weighed and charged to the reaction vessel, followed by a weighed quantity of MPSA catalyst.

TABLE III

PHENOL + Fn ----> BHPF
Catalyst MPSA, Neat Reactions - no solvent
Analytical Method 2 - UV Detector

| Run # | Temp. (°C.) | Mole Ratio | Mole % MPSA | Time (hr.) | 2,4/4,4 Area | 2:3/4,4% Area | % Conv. | MPSA ** |
|---|---|---|---|---|---|---|---|---|
| 1 | 65 | 10 | 5 | 2.2 | 0.017 | 0.011 | 99 | 0.0470 |
| 2 | 35 | 2 | 8 | 3 | 0.013 | 0.003 | 98 | 0.0382 |
| 3 | 55 | 21 | 8 | 1.5 | 0.016 | 0.004 | 100 | 0.0382 |
| 4 | 63 | 10 | 2 | 7.5 | 0.014 | 0.008 | 97 | 0.0187 |
| 5 | 63 | 15 | 13 | 1 | 0.017 | 0.005 | — | 0.0846 |
| 6 | 28 | 10 | 5 | 20 | 0.011 | 0.008 | 92 | 0.0470 |
| 7 | 45 | 10 | 5 | 5 | 0.012 | 0.007 | 91 | 0.0470 |
| 8[1] | 36 | 21 | 8 | 5 | 0.013 | 0.005 | 62 | |
| 9 | 36 | 21 | 3.9 | 7.25 | 0.012 | 0.005 | 95 | 0.0191 |
| 10[2] | 36 | 21 | 4 | 6.5 | 0.012 | 0.007 | 96 | 0.0202 |
| 11 | 35 | 21 | 159 | 1.83 | 0.028 | 0.011 | 100 | 0.6932 |
| 12* | 45 | 15 | 5 | 2.5 | 0.013 | 0.006 | 99 | 0.0330 |
| 13 | 45 | 15 | 5 | 3.5 | 0.014 | 0.007 | 100 | 0.0330 |
| 14* | 55 | 21 | 3 | 2 | 0.014 | 0.006 | 99 | 0.0146 |
| 15[3] | 35 | 21 | 18 mpa 5.2 msa | 20 | 0.034 | 0.011 | 100 | 0.0580 |

*vacuum used to remove water during reaction.
**moles/L
[1]Molecular sieves used to remove water while reaction is taking place + more catalyst is added.
[2]Fn added continuously over 43 min.
[3]MSA (methanesulfonic acid) and MPA (mercaptopropionic acid) used instead of MPSA The concentrations of materials in the resulting mixtures are followed by HPLC (Analytical Method 4).

The following mixtures are used:

| Neat Runs | | DPM Runs | |
|---|---|---|---|
| Chem. | wt % theory | Chem. | wt % theory |
| Phenol | 82.35 | Phenol | 47 |
| Fn | 0.00 | Fn | 0.00 |
| MPSA | 0.50 | MPSA | 0.21 |
| H$_2$O | 0.84 | H$_2$O | 0.48 |
| BHPF | 16.31 | BHPF | 9.3 |
| | | DPM | 43 |

To the reactor is added 200 mL of the mixture and 200 mL of water. The resulting mixture is stirred for 10 minutes. The phases are allowed to separate and the separation time noted. A sample (10 mL) of the organic phase is removed for analysis by HPLC and I.C. (ion chromatography). The aqueous phase is retained for analysis.

The extraction of the remaining organic layer is repeated, using an equal volume of water (190 mL). At the end of the extraction and separation, 10 mL of the organic layer is retained.

The remaining 180 mL of organic layer is extracted with 180 mL of water. A 10-mL sample of the organic layer is retained, as before.

The aqueous extract is distilled under vacuum to give a solution of phenol, MPSA and small amounts of BHPF. Acid titration and I.C. analysis indicates that all of the MPSA is recovered from the mixtures. Results of representative extractions are given in Table IV.

TABLE IV

Extraction Data for Neat 21:1 (phenol/Fn) Run (500 rpm Stirring Rate)

| Extraction | 1 | | 2 | | 3 | |
|---|---|---|---|---|---|---|
| Phase | Org. | Aq. | Org. | Aq. | Org. | Aq. |
| g. used | 217 | 200 | 251.4 | 190 | 216.2 | 180 |
| g. end | 262.2 | 154.9 | 226.9 | 214.5 | 196.4 | 199.8 |
| % Component in Phase | | | | | | |
| Phenol | 62.8 | 6.71 | 57.6 | 6.63 | 59.2 | 6.39 |
| Fn | 0.00 | 0.0 | 0.00 | 0.0 | 0.00 | |
| MPSA | 0.08 | 0.55 | 0.030 | 0.12 | 0.0100 | 0.039 |
| H₂O | 23.7 | 92.7 | 28.0 | 93.3 | 25.1 | 93.6 |
| BHPF | 13.4 | 0.0098 | 14.4 | | 15.8 | 0.0073 |

(150 rpm Stirring Rate)

| Extraction | 1 | | 2 | | 3 | |
|---|---|---|---|---|---|---|
| Phase | Org. | Aq. | Org. | Aq. | Org. | Aq. |
| g. used | 217 | 200 | 258 | 190 | 226.4 | 180 |
| g. end | 268.6 | 148.4 | 237.2 | 200.5 | 195.36 | 200.6 |
| % Component in Phase | | | | | | |
| Phenol | 60.1 | 6.37 | 61.6 | 7.17 | 61.1 | 6.82 |
| Fn | 0.00 | 0.0 | 0.00 | 0.0 | 0.00 | |
| MPSA | 0.10 | 0.53 | 0.0270 | 0.10 | ~0.005 | 0.03 |
| P-1 H₂O | 27.1 | 93.1 | 24.2 | 92.7 | 23.5 | 93.2 |
| P-2 BHPF | 12.7 | 0.0088 | 14.3 | — | 15.4 | — |

**4th and 5th extractions: equal volumes of organic and water layers: MPSA in organic 0.0030 (4th), 0.0005 (5th), in water 0.0143 (4th), 0.0025 (5th)

EXAMPLE 16

ISOMERIZATION STUDY IN THE PRESENCE OF MPSA

Reactions are done in stirred batch isothermal reactors (reactor design 2). To the reactor is charged a mixture of 83.2% by weight of phenol, 0.09% by weight of fluorenone, 13.2% by weight of BHPF, containing 0.92% by weight of 2,4-isomer and 0.68% by weight of 2:3 adduct. Various amounts of MPSA are charged to the reactor. The resulting mixtures are stirred and heated. The compositions in the reactor at various times are determined by analytical method 4.

Compositions of other reaction mixtures are given in Table V. Results are given in Table VI.

These results show that heating mixtures, in the presence of MPSA, brings about isomerization of the reaction mixtures toward higher concentrations of 9,9-bis-(4-hydroxyphenyl)-fluorene. The concentration of higher adducts also increases as a result of prolonged heating.

TABLE V

COMPOSITIONS FOR ISOMERIZATION STUDY

| Run | Temp °C. | mole/L MPSA | mole/L Phenol | g Rx Mix | g MPSA |
|---|---|---|---|---|---|
| 1 | 70 | 0.642 | 9.250 | 5.42 | 0.5710 |
| 2 | 55 | 0.340 | 9.705 | 5.42 | 0.2878 |
| 4 | 55 | 0.920 | 8.835 | 5.42 | 0.8540 |
| 6 | 55 | 0.642 | 9.250 | 5.42 | 0.5710 |
| 8 | 70 | 0.340 | 9.705 | 5.42 | 0.2878 |
| 9 | 70 | 0.920 | 8.835 | 5.42 | 0.8540 |
| 15 | 55 | 0.180 | 9.940 | 5.42 | 0.1520 |

TABLE VI

ISOMERIZATION STUDIES
% in Reaction Mixture

| | Time | Phenol | Fn | BHPF | 2:4* | 2:3* | 2nd add.* | % Total+ | Total* |
|---|---|---|---|---|---|---|---|---|---|
| Run 1 | 0 | 75.27 | 0.08 | 11.94 | 1.74 | 0.62 | 0.00 | 89.6 | 99.2 |
| S#1 | 4 | 76.86 | 0.00 | 13.09 | 1.61 | 0.26 | 0.018 | 91.8 | 101.4 |
| S#2 | 22.5 | 74.64 | 0.00 | 14.05 | 1.01 | 0.17 | 0.15 | 90.0 | 99.5 |
| S#3 | 52 | 76.18 | 0.00 | 14.30 | 0.88 | 0.14 | 0.23 | 91.71 | 01.3 |
| Run 2 | 0 | 79.00 | 0.09 | 12.66 | 1.84 | 0.65 | 0.00 | 94.2 | 99.3 |
| S#1 | 4 | 81.9 | 0.0 | 13.1 | 1.9 | 0.5 | 0.00 | 97.4 | 102.5 |
| S#2 | 21 | 76.71 | 0.00 | 13.21 | 1.56 | 0.29 | 0.0242 | 91.76 | 96.8 |
| S#3 | 29 | 80.41 | 0.00 | 14.07 | 1.53 | 0.23 | 0.0169 | 96.25 | 101.3 |
| S#4 | 94 | 80.96 | 0.00 | 14.18 | 0.89 | 0.14 | 0.07 | 92.17 | 101.2 |
| S#5 | 101 | 77.22 | 0.00 | 14.62 | 0.94 | 0.21 | 0.10 | 92.99 | 98.0 |
| Run 4 | 0 | 71.88 | 0.08 | 11.52 | 1.66 | 0.59 | 0.00 | 85.7 | 99.3 |
| S#1 | 2 | 67.53 | 0.06 | 12.25 | 1.68 | 0.40 | 0.00 | 81.92 | 95.5 |
| S#2 | 4.5 | 69.3 | 0.0 | 12.2 | 1.5 | 0.3 | 0.013 | 83.3 | 96.9 |
| S#3 | 24.5 | 74.49 | 0.07 | 13.18 | 0.95 | 0.15 | 0.04 | 88.88 | 102.5 |
| S#4 | 88 | 67.54 | 0.00 | 13.95 | 0.70 | 0.11 | 0.22 | 82.29 | 95.9 |
| Run 6 | 0 | 76.02 | 0.08 | 12.06 | 1.75 | 0.62 | 0.00 | 90.5 | 100.1 |
| S#1 | 2 | 73.72 | 0.00 | 13.01 | 1.83 | 0.51 | 0.00 | 89.0 | 98.6 |
| S#2 | 4.5 | 75.4 | 0.0 | 13.2 | 1.8 | 0.4 | 0.0 | 90.8 | 100.3 |
| S#3 | 24.5 | 78.39 | 0.00 | 13.36 | 1.17 | 0.18 | 0.02 | 93.13 | 102.7 |

TABLE VI-continued

ISOMERIZATION STUDIES
% in Reaction Mixture

|        | Time | Phenol | Fn   | BHPF  | 2:4* | 2:3* | 2nd add.* | % Total+ | Total* |
|--------|------|--------|------|-------|------|------|-----------|----------|--------|
| S#4    | 88   | 74.06  | 0.00 | 14.99 | 0.76 | 0.10 | 0.12      | 89.90    | 99.4   |
| Run 8  | 0    | 84.03  | 0.09 | 13.33 | 1.94 | 0.69 | 0.00      | 100.1    | 105.1  |
| S#1    | 7    | 78.92  | 0.00 | 14.00 | 1.69 | 0.29 | 0.00      | 94.90    | 99.0   |
| S#2    | 23   | 76.1   | 0.00 | 14.6  | 1.2  | 0.2  | 0.1       | 92.2     | 97.2   |
| S#3    | 52   | 79.09  | 0.00 | 14.92 | 1.02 | 0.15 | 0.12      | 95.30    | 100.3  |
| Run 9  | 0    | 72.59  | 0.08 | 11.52 | 1.68 | 0.59 | 0.00      | 86.5     | 100.1  |
| S#1    | 3    | 68.42  | 0.00 | 12.90 | 1.31 | 0.20 | 0.03      | 82.87    | 96.5   |
| S#2    | 7    | 70.5   | 0.0  | 13.2  | 1.0  | 0.2  | 0.1       | 84.8     | 98.4   |
| S#3    | 22.5 | 70.86  | 0.00 | 12.99 | 0.76 | 0.16 | 0.19      | 84.95    | 98.6   |
| Run 15 | 0    | 80.93  | 0.09 | 12.97 | 1.87 | 0.66 | 0.00      | 96.5     | 99.1   |
| S#1    | 2    | 83.36  | 0.00 | 13.83 | 2.01 | 0.66 | 0.00      | 99.8     | 102.6  |

*estimated
+including catalyst

EXAMPLE 17

PURIFICATION OF 9,9-BIS-(4-HYDROXYPHENYL)FLUORENONE

A. PRECIPITATION FROM METHYLENE CHLORIDE

A synthetic reaction mixture (105.5 g: 63% by weight, 66.5 g of phenol; 20% by weight, 21.1 g of 4,4-BHPF and 17% by weight, 18 g of water) is placed in a 500-mL round-bottom three-neck flask equipped with a heating mantle/Variac, thermometer, stirring bar and distillation arm. A "Therm-O-Watch" is used to control temperature of the liquid in the flask. A separate thermometer is placed in the distillation tower to monitor temperature in the vapor phase.

The mixture is stirred and heated at ambient pressure up to a temperature of 160° C., during which time distillation of phenol and water occurs. Analysis of the reaction mixture indicates the phenol:BHPF mass ratio is 1:1. The reaction mixture, while still hot, is slowly added to 176 g of BHPF-saturated methylene chloride and the resulting mixture is slowly swirled to produce a homogeneous solution, clear and yellow in color. The mixture is allowed to cool to room temperature which causes crystallization to occur.

The rod-like crystals present in the magma are analyzed by microscope prior to filtration. Approximately 80% of the crystals viewed are longer than 100 microns and have a diameter between 20 and 50 microns.

The crystal magma is filtered on a medium porosity glass frit, using a vacuum produced by water jet. The filter cake is displacement-washed with 79 g of BHPF-saturated methylene chloride and then 72 g of hot (90° C.) water. After drying at 65° C. in air overnight, 12.9 g of white product is recovered. Isolated yield is 61% and HPLC purity is 99.8%.

B. WASHING WITH SODIUM BICARBONATE SOLUTION

Synthetic reaction mixture (105.5 g as in Example 17A) is combined with 100 mL of a 2% by weight aqueous solution of sodium bicarbonate. The mixture is agitated and then the organic and aqueous layers are allowed to separate in a separatory funnel. The organic layer is drawn off. This process is performed a total of 4 times. Washed reaction mixture (85.2 g: 58%, 58 g of phenol; 17.4%, 17 g of 4,4-BHPF and 25%, 21 g of water) is placed in the apparatus, described in Example 17A.

The mixture is stirred and heated at a pressure of 80–100 mm Hg, up to a temperature of 160° C., during which time distillation of phenol and water occurs. BHPF-saturated phenol (100 g) is then added to the reaction mixture and the temperature of the mixture is controlled at 65° C. Crystallization begins within 1 h. The slurry is stirred overnight, after which the rod-like crystals present in the magma are analyzed by microscope before filtration. Approximately 30% of the crystals viewed have a length greater than 100 microns and a diameter between 10 and 30 microns.

The crystal magma is filtered on a medium porosity glass frit using a vacuum produced by water jet. The brown filter cake is displacement-washed with 200 mL of room-temperature water and then stir washed with the same amount of water. The brown/beige crystals are then washed with BHPF-saturated methylene chloride and then with ethylene dichloride. After drying at 65° C. in air overnight, 7 g of brown product Are recovered. The isolated yield is 47% and HPLC purity is 99.7%.

C. DISTILLATION OF PHENOL, CRYSTALLIZATION FROM TOLUENE

Synthetic reaction mixture (149 g: 17.5% by weight, 24 g of 4,4-BHPF; 95 g of phenol and 30 g of water) are charged to the reactor, described in Example 17A. The mixture is stirred and heated at a pressure of 80–100 mm Hg up to a temperature of 160° C., during which time distillation of phenol and water occurs until the phenol:BHPF mass ratio is reduced to approximately 1:1. There is no increase in adduct concentration.

The resulting mixture is added while still hot to 121 g of BHPF-saturated toluene. The resulting homogeneous solution is allowed to cool to room temperature, during which crystallization occurs. The resulting rod-like crystals present in the magma are analyzed by microscope prior to filtration. Approximately 20% of the crystals viewed have a length greater than 100 microns and a diameter between 10 and 50 microns.

The crystal magma is filtered on a medium porosity glass frit using a vacuum produced by water jet. The pink filter cake is treated similarly to other examples. After drying at 65° C. in air overnight, 18.5 g of pink product are recovered. Isolated yield is 77% and HPLC purity is 98.1%.

D. DISTILLATION OF PHENOL; CRYSTALLIZATION FROM METHYLENE CHLORIDE

Phenol and fluorenone are combined in the presence of 3-mercaptopropanesulfonic acid (MPSA) to produce a reaction mixture which, after washing to remove the acid catalyst, contains 20 wt % of 4,4-BHPF, 64 wt % of phenol and 16 wt % water. The reaction mixture is distilled under water jet vacuum (approx. 80 mm Hg) up to a temperature of 160° C. to yield a residue, containing approximately 50 wt % of phenol and 50 wt % of 4,4-BHPF, i.e., a 1:1 phenol:4,4-BHPF mass ratio.

The 1:1 mixture is cooled to 120° C. and then poured into 176 g of room temperature methylene chloride, that had been previously saturated with 4,4-BHPF. This results in a clear homogeneous solution at reflux, which is allowed to cool to room temperature. The crystallized mixture is filtered under vacuum at room temperature. The filter cake is displacement washed with 79 g of BHPF-saturated methylene chloride (no stirring of the filter cake during the wash) and then stir-washed with 72 g of hot water (90° C.) The resulting white filter cake is dried in air at 60° C. to provide a yield of 61 wt % of the 4,4-BHPF originally detected in the reaction mixture.

E. REMOVAL OF PHENOL-WATER AZEOTROPE

Approximately 380 g of a reaction mixture similar to that of Example 17D are slowly dripped into 4 L of water at a temperature of 84° C. at a pressure of 300 mm Hg. This dilution in water is accompanied by the removal of phenol in the form of a water/phenol azeotrope. The water-insoluble materials then precipitate from the liquid phase as a white powder. Approximately 64 g of "crude" BHPF is obtained in this manner. The "crude" BHPF contains all the impurities originally contained in the reaction mixture. The product is filtered, washed with boiling water and dried in air at 60° C. to provide a recovery of 96 wt % of the 4,4-BHPF originally detected in the reaction mixture.

F. CRYSTALLIZATION FROM TRIISOPROPYLBENZENE

A reaction mixture (55.8 g: 63.1% by weight, 35 g of phenol; 14% by weight of 4,4-BHPF and 23% by weight, 12.8 g of water) is charged to a 250-mL round bottom flask, otherwise fitted out as in Example 17A. Triisopropylbenzene (TIPB, 106.6 g) is added to the mixture in the flask, as a result of which the mixture separates into two phases, of which the yellow reaction mixture is the lower.

The mixture is stirred and heated under vacuum, produced by a water jet (ca. 80 mm). After removal of water at 50–88° C., the mixture appears homogeneous. The mixture is stirred and allowed to cool. Solids appear when the temperature reaches about 70° C. The mixture is allowed to cool to room temperature and filtered on a glass frit under vacuum. The white solids on the frit are washed with TIPB. The filter cake is left overnight under vacuum (water jet) while air is pulled through the filter cake.

Analysis of the resulting mother liquor shows that little of the phenol in the feed is removed as a result of distillation. The filter cake contains 4.2 g of white, nearly free-flowing product (54% recovery, 98.8% purity by HPLC).

G. DISTILLATION TO REMOVE PHENOL; CRYSTALLIZATION FROM METHYLENE CHLORIDE

A reaction mixture (98.8 g: 61% by weight, 60.3 g of phenol; 19.4% by weight, 19.2 g of 4,4-BHPF and 19.6% by weight, 19.4 g of water) is charged to an apparatus, described in Example 17F. A collection flask is attached to the distillation arm and connected to a vacuum source (water jet). The temperature set point is adjusted to 100° C. and heating is begun.

| Temp. (°C.) | Observations/Actions |
|---|---|
| 50–55 | boiling and distillation occur |
| 100 | slight bubbling |
|  | set point raised to 120° C. |
| 105 | distillation restarts |
| 115 | insignificant distillation |
|  | set point raised to 140° C. |
| 120 | vigorous boiling, little distillation, vapor temperature rising |
| 121 | vigorous boiling, distillation starting, vapor temperature 115° C. |
| 122 | vapor temperature 118° C. break vacuum and remove sample: 34 g of distillate collected, mixture in pot has phenol:BHPF mass ratio of ca. 2:1 reconnect vacuum source and recommence heating |
| 124 | vapor temperature is 119° C., distillation starts |
| 125 | vapor temperature is 119° C. break vacuum and sample mixture 13.9 g of distillate collected set point 120° C. at atmospheric pressure reconnect vacuum and recommence heating phenol:BHPF 1.6:1 mass ratio in pot |
| 129 | vapor temperature 121° C. distillation starts |
| 131 | vapor temperature 123° C. stop operation, remove sample 42.4 g remain in pot; mixture in pot has phenol:BHPF ratio ca. 1.12:1; 6.7 g of distillate collected |

The pot residue at 110° C. is added to 172 g of fresh drum-grade methylene chloride in a bottle. The addition is done slowly in order to avoid excessive flashing or boiling of the methylene chloride. The resulting mixture more or less separates into two layers, of which the upper layer is richer in the phenol:BHPF component. The mixture is swirled and becomes homogeneous. The bottle is sealed and placed in a pan of cold water (ca. 10° C.).

| Time (hr:min.) | Observations/Actions |
|---|---|
| 0.08 | homogeneous yellow solution |
| 0.18 | homogeneous yellow solution |
| 0.56 | yellow solution, possibly small crystals |
| 1.18 | same |
| 2:00 | same |
| 2:24 | crystallization ongoing, quite a few crystals |
| 17:48 | solid yellow crystalline mass breaks up easily filter under vacuum through glass frit to obtain slightly yellow crystals; recover 158.8 g of yellow mother liquors |

The crystallizer bottle is rinsed with 29.7 g of fresh methylene chloride (not all solids dissolve), the resulting mixture being used to displacement wash the filter cake, which improves slightly in color.

The filter cake is slurry washed with 49.4 g of fresh methylene chloride and the resulting slurry is filtered under vacuum. The color of the filter cake is unchanged.

The filter cake is displacement washed with 33 g of cold water, without a change in the color of the cake. The filter cake is slurry washed with 40 g of boiling water, without a change in the color of the cake.

The cake is dried in air under vacuum for ca. 2 h, transferred to a watch glass and dried in an oven overnight at 65° C. The cake is slightly yellow.

The mass balance for the process is:

| g of BHPF |  |
|---|---|
| 19.2 | in initial mixture |
| 8.1 | in mother liquors at end of operation |
| 9.1 | isolated product |

-continued

| g of BHPF | |
|---|---|
| 1.7 | in wash |
| 0.3 | unaccounted for |

H. CRYSTALLIZATION FROM DIPHENYLMETHANE

1. A mixture of 28 g of DPM, 17.5 g of phenol, 5.4 g of BHPF (98:2 4,4- to 2,4- isomers, by HPLC) and 12 mg of MPSA is washed with water. The resulting layers are separated and the water layer is removed. Phenol is distilled from the organic layer to give a mixture containing 21.8 g of DPM, 3.8 g of phenol and 5.4 g of BHPF. The mixture to cooled to room temperature to give an off-white precipitate, which is filtered and washed with DPM. The washed cake is dried in an oven at 60° C. to give 6.1 g of material, containing 70% by weight of BHPF and 30% by weight of phenol. The mixture is stripped at 140° C. under nitrogen at <80 mm Hg to give 4.2 g of white solid. The solid, by HPLC analysis (analytical method 5), contains 99.6% by area of the 4,4-isomer and 0.04% by area of 2,4-isomer.

2. A reaction mixture from 15:1 phenol:fluorenone, containing 34.5% by weight of phenol and 10.5% by weight of BHPF, is diluted with 55% by weight of DPM. Phenol (80% of that initially present, maximum temperature 105° C., 4.5 mm Hg) is removed by distillation to give, after crystallization from DPM, white BHPF melting at 221–222° C. The recovery of BHPF is 78%. The material contains area 99.6% of the 4,4-isomer by HPLC.

I. CRYSTALLIZATION FROM NEAT PHENOL

Phenol is distilled from the reaction mixtures to produce mixtures, containing less than 50:50 phenol:BHPF by weight. The resulting materials can be washed with methylene chloride. The products are inconsistent in color and contain small crystals, usually of the order of 10–70 microns.

J. PRECIPITATION OF BHPF BY ADDITION TO WATER

Addition of reaction mixtures to boiling water or steam removes some phenol as a phenol-water azeotrope. The resulting product retains most of the extraneous isomers and adducts and comprises very small crystals, of the order of 10–20 microns. The maximum purity is of the order of 97–98%.

Analytical data (HPLC) are given in Table VII for samples, prepared in accordance with the practice of the invention and for commercially-available materials.

K. REMOVAL AND RECOVERY OF PHENOL FROM BHPF REACTION MIXTURE

Excess phenol is removed from a reaction mixture to a 1:1 ratio of phenol:BHPF using a falling film evaporator. This is accomplished at 120° C./120 mm Hg. At this temperature, BHPF solubility in phenol is about 45%.

After removing phenol, the BHPF-phenol mixture is kept at about 90° C. and stirred prior to addition of methylene chloride or other crystallizing solvent.

BHPF is crystallized at room temperature under a nitrogen pad. A batch crystallizer is cooled to 5–10° C. for several hours during which BHPF crystallizes. Solid BHPF is separated from the resulting slurry using a batch pressure filter or basket filter. Optionally, a pressure filter can be used. Methylene chloride or other solvent can be recycled to the process.

BHPF crystals are dried under vacuum.

COMPARATIVE MATERIALS

BHPF from Sloss (Birmingham, Alabama): The sample evaluated is a dry solid, from lot number 9307-03.

BHPF from Isonova (Austria): The sample evaluated is designated "Isonova 10/93".

BHPF from Rutgers Nease (State College, Pennsylvania): The dry solid is from lot number 9306099.

BHPF from Isovolta (Neudorf, Austria): The sample, used as standard for the comparative studies, was received in 1988 and is designated "Isovolta 1988."

Analysis of the results in Table VII shows that 4,4-BHPF, purified by distillative removal of phenol:water azeotrope and extraction with methylene chloride, produces high purity BHPF.

TABLE VII

| Sample Source | Lot No. | 4,4-BHPF | 2.4-BHPF | 2:3 BHPF Add. | Other | Total Impur. |
|---|---|---|---|---|---|---|
| Sloss | 9307-03 | 100 | ~0 | 0 | 0 | 0 |
| Isonova | 10/93 | 100 | 0 | 0 | | 0.00 |
| MeCl₂ | Ex. 170 | 99.94 | | 0.06 | | 0.06 |
| Water ppt'd | Ex. 17E | 97.59 | 1.87 | 0.40 | 0.14 | 2.41 |
| Isovolta | 1988 | 100 | 0 | 0 | | 0 |
| Rutgers Nease | 93060099 | 99.28 | 0.58 | 0.14 | | 0.72 |
| DPM | Ex. 17H | 99.6 | | | | |

EXAMPLE 18

CORROSION STUDIES

A. REACTION MIXTURES FOR BHPF PROCESS

Corrosion tests are performed using a representative reaction mixture for the condensation of phenol with fluorenone using various catalysts. The tests are done using metal specimens 3.81 cm in length, 1.59 cm in width, 0.32 cm thick, and having a 0.64 cm hole centered in one end. The specimens are isolated from each other and the mounting rack using polytetrafluoroethylene shoulder washers. The specimens are exposed to both the liquid and vapor phases of each test cell. The contents of the cells are stirred continuously and are maintained at the selected temperature using YSI temperature controllers and GLASCOL™ heating mantles. The tests are run under a nitrogen pad. The chloride content of the test mixtures is <500 ppm. The tests are run at 65° C. for 13 days (312 h). Compositions tested and results are presented in Table VIII.

Results in Table VIII demonstrate that the reaction mixtures used are considerably less corrosive than conventionally used reaction mixtures.

TABLE VIII

CORROSION TESTING FOR BHPF REACTION MIXTURES

| | Corrosion Rate (mpy)* | | |
|---|---|---|---|
| Metal | Liquid | Vapor | Remarks |
| A. Reactor Mixture: 90.2% of Phenol, 8.3% of Fluorenone, 1.5% of MPSA (by weight) | | | |
| 316L ss** | nil*** | <0.1 | uniform corrosion |
| 904L ss | nil | 0.1 | uniform corrosion |
| 2205 ss | nil | <0.1 | uniform corrosion |
| 254 SMO ss | nil | nil | uniform corrosion |
| B. Water Extraction Mixture: 8.0% of Phenol, 91% of Water and 1.0% of MPSA (by weight) | | | |
| 316L ss | 0.1 | 0.1 | uniform corrosion |
| 904L ss | <0.1 | <0.1 | uniform corrosion |
| 2205 ss | <0.1 | <0.1 | uniform corrosion |
| 254 SMO ss | <0.1 | <0.1 | uniform corrosion |

TABLE VIII-continued

CORROSION TESTING FOR BHPF REACTION MIXTURES

| | Corrosion Rate (mpy)* | | |
|---|---|---|---|
| Metal | Liquid | Vapor | Remarks |
| C. Recycle Concentrate: 29.87% of Phenol, 69.23% of Water and 0.9% of MPSA (by weight) | | | |
| 316L ss | 0.1 | 0.1 | uniform corrosion |
| 904L ss | <0.1 | <0.1 | uniform corrosion |
| Inconel 625 | <0.1 | <0.1 | uniform corrosion |
| Hastelloy C-27 | 0.1 | <0.1 | uniform corrosion |
| Hastelloy G-30 | <0.1 | <0.1 | uniform corrosion |

*mpy = mils per year; 1 mpy = 0.00254 cm/yr
**ss = stainless steel
***nil = <0.01 mpy

B. REACTION MIXTURES FOR BISPHENOL A PROCESS

A mixture containing 94.35% by weight of phenol, 4.15% by weight of acetone and 1.50% of MPSA is evaluated as in Example 18A.

The following results are obtained:

| | Corrosion Rate | |
|---|---|---|
| Metal | Liquid | Vapor |
| 304L ss | pass | pass |
| 316L ss | pass | pass |
| 904L ss | pass | pass |
| 2205 ss | pass | pass |
| 825 Ni | pass | pass | pass = <0.00254 cm/year

The corrosion rates in both the liquid and vapor phases is <0.00254 cm/year. The corrosion is uniform. The rate of corrosion is below that for conventional reaction mixtures for making bisphenol A.

EXAMPLE 19

A. PREPARATION OF BISPHENOL A USING PMBSA

Bisphenol A is prepared from 14:1 phenol:acetone (mole ratio) at 50° C., containing the indicated amounts of solid catalyst. The product distribution is determined by analytical method 2.

The PMBSA catalyst of Example 9B, at a level of 6% by weight, gives about 75% conversion after 5 h. The product contains 99.0:1.0 of 4,4:2,4-isomers (area %).

The PMBSA is recovered and reused in a second cycle. The conversion after 4 h is about 60%. The product contains 99.1:0.9 of 4,4:2,4-isomers (area %).

DOWEX™ 50WX4 (35% by weight as dry mass), promoted with 25% by weight of 2,2-dimethylthiazolidine, is used in a similar experiment. The conversion after 4 h is 43% and the product contains 98.0:2.0 (as area %) of 4,4:2,4-isomers.

These experiments show that a polymer-supported catalyst of this invention gives higher conversions and a higher yield of 4,4-isomer than a representative prior art catalyst.

B. REACTION USING PMBSA IN A DOWNFLOW CONTINUOUS REACTOR

The reactor comprises a vertical tube. The bottom part of the tube is filled with glass beads, on top of which is provided a bed of PMBSA catalyst resin. The remainder of the tube is filled with glass beads. The tube is fitted with a pressure gauge, a pressure regulator, heating means external to the catalyst bed and feed means at the bottom of the tubular reactor for introducing the phenol and fluorenone reactants. The feed is prepared in a container, provided with a nitrogen stream and heated externally by a fluid. A valve is intermediate the feed preparation container and a pump for introducing the feed into the bottom of the reactor. A relief valve is placed between the pump and the reactor.

The feed is introduced into the reactor at a predetermined rate and passes upwardly through the lower bed of glass beads, which functions as a preheater, through the catalyst bed and the upper bed of glass beads, whereupon the product is removed from the top part of the reactor for analysis or further processing.

Experiments using 21:1 phenol:fluorenone and PMBSA catalyst gave the following results as a function of flow rate and reaction temperature:

| | 49° C. | 69° C. |
|---|---|---|
| Conversion (%) | 80 | 100 |
| BHPF in phenol (%) | 14 | 16 |
| Productivity (g BHPF/g cat/h) | 0.57 | 0.44 |
| Selectivity (% 4,4-BHPF) | 98+ | 97+ |
| Flow rate (g feed/g cat · h) | 4.39 | 2.71 |

These experiments show that lower reaction temperatures favor productivity and selectivity toward 4,4-BHPF, accompanied by decreased conversion.

C. CONVERSION OF ACETONE AS A FUNCTION OF REACTION TEMPERATURE

Phenol-acetone mixtures (6% by weight acetone) are converted to bisphenol A, using MPSA as catalyst in batch reactors. The following results are obtained (Table IX):

TABLE IX

| | Acetone Conversion | | | | |
|---|---|---|---|---|---|
| Time (min) | 25° C.* | 35° C.* | 55° C.+ | 65° C. | 75° C.+ |
| 0 | 0 | | 0.10 | 0.22 | 0.25 | 0.26 |
| 20 | | | | 0.40 | 0.48 | 0.49 |
| 25 | 0.04 | 0.42 | | | |
| 40 | | | 0.59 | 0.62 | 0.67 |
| 48 | | | 0.65 | 0.69 | 0.77 |
| 60 | 0.06 | 0.56 | 0.69 | 0.75 | |
| 72 | | | | | 0.82 |
| 90 | 0.09 | | 0.79 | 0.85 | 0.89 |
| 120 | 0.13 | 0.72 | 0.83 | 0.89 | 0.94 |
| 180 | 0.20 | 0.80 | | 0.95 | 0.96 |
| 240 | 0.26 | | | 0.97 | |
| 300 | | | | 0.98 | |
| 360 | 0.32 | | | | 0.99 |

*mixture contains 2.2% by weight of MPSA and 2–3% by weight of water
+mixture contains 1.3% by weight of MPSA and no added water

D. REMOVAL OF MPSA CATALYST USING ION-EXCHANGE RESIN; PURIFICATION OF CRYSTALLINE BISPHENOL A

Condensation of phenol with acetone (4% by weight), containing about 2 by weight of water, using 2.5% by weight of MPSA, is done at 35° C. in plug flow mode, with a 3 h residence time. Crystallization of bisphenol A occurs in the reactor. The crystals are isolated by filtration and residual acetone in the mother liquors is recycled to the process at 50° C. THE mother liquors are dried at 50° C. (20 mm Hg) and the cycle is repeated after addition of make-up feed. About 90% of the acetone is converted to bisphenol A per pass.

Catalyst is removed from the product by first melting the crystals and washing the resulting oil with water, and then extracting the organic layer with water, which reduces the acid concentration below about 100 ppm after three equilibrium stages. The remaining catalyst is removed using an anion exchange bed (<50 ppm, the limit of detection).

Bisphenol A, isolated by a single crystallization step, is of higher purity than products, generally obtained using two crystallizations. Bisphenol A isolated by a single crystallization, contains a maximum of about 1200 ppm of 2,4-bisphenol. The process of this invention therefore simplifies the isolation of high purity of bisphenol A, uncontaminated by oily higher condensates.

EXAMPLE 20

SOLID CATALYST PREPARED FROM POLYSTYRENE BY ALKYLATION WITH ALLYL BROMIDE, SULFONATION AND THIOLATION

A. Polystyrene (Amberlite® XE 305) is alkylated with allyl bromide in the presence of trifluoromethanesulfonic acid in 1,2-dichloropropane at 50° C., generally in accordance with Tomoi et al., "A Novel One-pot Synthesis of Spacer-modified Polymer Supports and Phase-transfer Catalytic Activity of Phosphonium Salts Bound to the Polymer Supports," *Reactive Polymers*, vol. 3 (1985), pages 341–349, to produce a material having 2-bromo-1-methylethyl chains. This material is sulfonated, generally at the ortho-position with respect to the side chain, by treatment with chlorosulfonic acid. The resulting sulfonyl chloride is converted to a sodium salt by reaction with sodium bicarbonate. The material is converted to a corresponding thiol by reaction with sodium thioacetate and converted to a corresponding acid by acidic hydrolysis. Materials prepared correspond to 28 and 48% of alkylmercaptan functionality (XEMSA).

B. The thus-prepared polymers (XEMSA) are used at a level of 6% by weight for reaction between phenol and fluorenone (20.8:1 mole ratio) at 50° C. Product composition is determined by analytical method 3.

The polymer containing 28% of alkylmercaptan functionality gives 75% conversion after 5 h. The product distribution is 96.8:3.2 of 4,4:2,4-isomers (area %).

The product containing 48% of alkylmercaptan functionality gives 15% conversion after 2 h. The product distribution is 96.8:3.2 of 4,4:2,4-isomers (area %).

EXAMPLE 21

IN SITU METHOD FOR PREPARING THE POLYMER-SUPPORTED MERCAPTOSULFONIC ACID CATALYST (PMBSA CLASS):

A. SULTONE ALKYLATION

To a mixture of 1,4-butanesultone (30.0 g, 220.0 mmol, 1.00 equivalent) and poly(vinylbenzylchloride) (PVBC, 33.6 g, approximately 220 mmol, 1.00 equivalent) of chloromethyl groups) is added via a cannula dry tetrahydrofuran (600 mL) under a nitrogen atmosphere. The mixture is stirred at room temperature until a homogeneous solution is obtained. The solution is then cooled to −78° C. using a dry ice/acetone bath. n-Butyllithium (2.5 molar in hexanes, 88.1 mL, 1.00 equivalent) is added slowly dropwise to the −78° C. solution of 1,4-butanesultone and poly (vinylbenzylchloride) via an addition funnel over approximately 2.5 h with vigorous stirring. A white solid begins to precipitate from the reaction mixture as the n-butyllithium addition is begun, with precipitation continuing throughout the n-butyllithium addition period. By the end of the addition, a large amount of white solid has formed within the reaction medium.

The reaction mixture (slurry) is allowed to slowly warm to room temperature in the cooling bath (over approximately 3–4 h) and is allowed to stir at room temperature overnight. The white precipitate which has formed in the reaction mixture during the n-butyllithium addition period remains insoluble as the mixture reaches room temperature. The white (insoluble) solid is removed by vacuum filtration. The polymer can be washed with water or water can be added to the THF/polymer slurry prior to filtration. Addition of water sometimes results in increasing the time required for filtration. The solid is slurry-washed with THF, then with methanol and finally with methylene chloride (causing some swelling). The solid is dried overnight in a vacuum oven to provide 53.4 g of a white solid sultone-functional polymer.

B. THIOLATION

To the sultone-functional polymer from above (110.0 g from two combined batches, approximately 0.440 mol of sultone) is added nitrogen-saturated THF (500 mL). In a separate reactor, a solution of lithium thioacetate is prepared by the dropwise addition of thioacetic acid (49.8 g, 0.650 mol) to a slurry of lithium carbonate (24.2 g, 0.330 mol) in water (100 mL, nitrogen saturated). The lithium thioacetate solution is added slowly via cannula to the polymer/THF slurry at such a rate that the temperature does not rise above about 35° C. The polymer swells substantially during the lithium thioacetate addition. After the lithium thioacetate addition is complete, an additional 350 mL of water (nitrogen saturated) is added. The polymer swells to a volume of approximately 1 L. The mixture is heated to 50° C., and is allowed to react overnight. The gel-like polymer is then filtered using a coarse glass-fritted funnel. The polymer is washed with water, then with methanol, then with methylene chloride, and finally with additional water. The polymer slurry sometimes filters very slowly during the filtration process. In this case, the washing steps required approximately two days.

After the washing steps, concentrated hydrochloric acid (300 mL, approximately 37% by weight in water) is added to the polymer. The polymer shrinks in volume and the HCl solution is easily removed by filtration. More concentrated HCl (300 mL) is added to the filtered solid, and the mixture is allowed to stand at room temperature over 2 days. The polymer is then washed extensively with dilute HCl solution, followed by extensive water washes. The polymer is then washed with methanol and finally with dichloromethane. Drying overnight in a vacuum oven (60° C./full vacuum) provides the polymer-supported mercaptosulfonic acid. The product is identified as PMBSA-SU.

C. CONVERSION OF CROSSLINKED POLYSTYRENE RESIN TO MERCAPTOSULFONIC ACID POLYMER

A commercially-available (Fluka Chimika) crosslinked chloromethylated Merrifield resin (2% divinylbenzene, 200–400 mesh, approximately 4.3 mmol Cl/g, 51.2 g, 1.0 equivalent) is reacted with 1,4-butanesultone (1.05 equivalents) and n-butyllithium (1.0 equivalent) according to the procedure described above to provide a sultone-functional polymer (70.0 g). Subsequent thiolation of the sultone polymer in a manner similar to that described above provides the corresponding mercaptosulfonic acid polymer (79.0 g dry mass). This material is identified as PMBSA-MER.

In this reaction sequence, the lithium thioacetate reagent is formed in situ by slowly adding solid lithium carbonate to a mixture of the sultone polymer and thioacetic acid in a 3:2 volume ratio of nitrogen-saturated THF/water.

EXAMPLE 22

PREPARATION OF POLYMER-SUPPORTED MERCAPTOSULFONIC ACID CATALYST (XEMSA CLASS)

A. ALKYLATION OF POLYSTYRENE

To Amberlite™ XE-305 (75.0 g, approximately 0.720 mol of styrene repeat units, 1.00 equivalent) is added 600 mL of 1,2-dichloropropane (PDC). The polymer is allowed to swell in the solvent overnight. 5-Bromo-1-pentene (75.3 g, 0.702 equivalent) and PDC (125 mL) are added to an addition funnel. The reactor contents (polymer slurry and 5-bromo-1-pentene solution) are evacuated and back-filled with nitrogen several times. Trifluoromethanesulfonic acid (20.0 g, 0.133 mol, 0.19 equivalent) is added to the polymer/PDC slurry. The slurry solution turns a dark amber color. The polymer slurry is heated to 45–50° C., and slow, dropwise addition of the 5-bromo-1-pentene solution is begun. The 5-bromo-1-pentene solution is added slowly over approximately 3 days to the stirred polymer slurry at 50° C. After the 5-bromo-1-pentene addition is complete, the reaction is allowed to stir an additional 1 day at 50° C. The polymer slurry is very dark-colored throughout the addition period.

The polymer slurry (very dark red-brown) is cooled to room temperature and filtered. The beads are washed extensively with dichloromethane (still dark colored beads) and then are washed extensively with water to remove most of the color. The beads are then washed with the following series of solvents: methanol, acetone, dichloromethane, acetone, and, finally, methanol. After drying in a vacuum oven at 60° C. overnight, 96.46 g of nearly white bromoalkylated polymer beads are obtained. The mass uptake corresponds to a degree of functionalization (DF) of approximately 0.20.

B. SULFONATION

To the dried bromoalkylated polymer beads prepared above (approximately 0.720 mol of styrene repeat units) is added 650 mL of dichloromethane under a nitrogen atmosphere. The polymer slurry is cooled to 0° C. using an ice/water bath. Chlorosulfonic acid (258.2 g, 2.22 mol, 3.08 equivalents) is added slowly dropwise to the polymer slurry at 0° C. over 2 h 40 min. The polymer beads turn copper-colored during the chlorosulfonic acid addition. After the addition is complete, the reaction mixture is allowed to slowly warm to room temperature within the water bath. The volume of the swollen polymer is approximately 500–600 mL within the reactor. After warming to room temperature, the polymer slurry is allowed to stand overnight without stirring. The liquid layer is then removed from the polymer using a small-bore cannula. The beads are then washed several times with dichloromethane. (The liquid layer and dichloromethane washes are slowly and carefully quenched in a separate vessel using ice.) The polymer beads are then carefully transferred to a fritted-glass funnel, and the polymer beads are quenched by slow, careful addition of ice water.

After washing the beads extensively with water, excess solid sodium bicarbonate is slowly added to a suspension of the polymer beads in water. The mixture is allowed to stand overnight at room temperature. The polymer/sodium bicarbonate mixture is then heated to 50° C. for 2 h. The polymer slurry is allowed to stand at room temperature for 6 days. The polymer is light-colored and more highly swollen at this point. The slurry is heated to 50° C. and allowed to react overnight, giving a pH 4 solution of even more swollen polymer (approximately 600–700 mL volume). Addition of a small amount of sodium bicarbonate gives a pH 7 solution.

C. THIOLATION

To the aqueous polymer bead slurry from above is added sodium bicarbonate (60.5 g, 0.720 mol). The mixture is evacuated and back-filled with nitrogen three times. Thiolacetic acid (41.1 g, 0.540 mol) is added slowly dropwise over 1 h 10 min to the polymer slurry at room temperature. The mixture is slowly warmed to 80° C. over several h and allowed to react at 80° C. for 3 days. After cooling to 40° C., the supernatant solution is removed using a small-bore cannula. The polymer is washed several times with water, giving slightly off-white colored polymer beads. Concentrated hydrochloric acid (250 mL) is added to the polymer and the slurry is heated to 50° C. for 3 h. After cooling to room temperature, the hydrochloric acid solution is removed using a small-bore cannula. The polymer beads are then washed several times with dilute hydrochloric acid and the beads are transferred to a fritted-glass funnel. The beads are again washed repeatedly with dilute hydrochloric acid followed by extensive washings with water, giving slightly off-white water-swollen beads. (The water-swollen volume of the polymer beads is approximately 900 mL.) The beads are washed with methanol (methanol-swollen volume approximately 600 mL) and finally with dichloromethane. After drying in a vacuum oven at 60° C. overnight, the dark-colored beads have a dry volume of approximately 200 mL. This product is identified as XEMSA-5C.

D. PREPARATION OF CATALYST FROM POLYSTYRENE AND 11-BROMO-1-UNDECENE (XEMSA-11C)

Catalyst is prepared as above, starting with macroporous polystyrene (Amberlite™ XE-305) and 11-bromo-1-undecene.

EXAMPLE 23

EVALUATION OF POLYMERIC MERCAPTOSULFONIC ACID CATALYSTS

A. EVALUATION OF THE MERCAPTOSULFONIC ACID POLYMER (XEMSA-5C) IN THE REACTION OF PHENOL WITH FLUORENONE

To a 4 dram vial equipped with a stirring bar is added 4.32 g of a 20.8:1 molar ratio mixture of phenol to fluorenone and 0.26 g (6% by weight of the reactant solution) of the mercaptosulfonic acid polymer (XEMSA-5C) prepared as described in Example 22A–C. The reaction mixture consists of a homogeneous liquid phase plus a separate heterogeneous polymer catalyst phase. The mixture is heated to 50° C. for 5 h. The reaction is monitored throughout the reaction period by collecting samples and analyzing by HPLC. The 9-fluorenone is found to be 36% consumed within 2 h and 76% consumed within 5 h. HPLC analysis (analytical method 3) gives the following relative area % analysis for the products after 5 h of reaction (76% conversion): 9,9-bis-(4-hydroxyphenyl)fluorene (97.45 area %): 9-(2-hydroxyphenyl)-9-(4-hydroxyphenyl)fluorene (2.17 area %): adduct containing two fluorene units and three phenolic units (0.39 area %).

B. EVALUATION OF THE MERCAPTOSULFONIC ACID POLYMER (XEMSA) IN THE REACTION OF PHENOL WITH FLUORENONE

To a 4 dram vial equipped with a stirring bar is added 4.32 g of a 20.8:1 molar ratio mixture of phenol to fluorenone and 0.26 g (6% by weight of the reactant solution) of the mercaptosulfonic acid polymer (XEMSA, degree of functionalization approximately 0.28 from bromoalkylation step) prepared as described in Example 20. The reaction mixture consists of a homogeneous liquid phase plus a separate heterogeneous polymer catalyst phase. The mixture is heated to 50° C. for 5 h. The reaction is monitored throughout the reaction period by collecting samples and analyzing by HPLC. The 9-fluorenone is found to be 44% consumed within 2 h and 75% consumed within 5 h. HPLC analysis (analytical method 3) gives the following relative area % analysis for the products after 5 h of reaction (75% conversion): 9,9-bis-(4-hydroxyphenyl)fluorene (96.10 area %): 9-(2-hydroxyphenyl)-9-(4-hydroxyphenyl)fluorene (3.52 area %): adduct containing two fluorene units and three phenolic units (0.38 area %).

C. EVALUATION OF MERCAPTOSULFONIC ACID POLYMER (PMBSA-MER) IN THE REACTION OF PHENOL WITH FLUORENONE

To a 4-dram vial equipped with a stirring bar is added 4.32 g of a 20.8:1 molar ratio of phenol:fluorenone and 0.26 g (6% by weight of the reaction solution) of PMBSA-MER of Example 21C. The reaction mixture consists of a homogeneous liquid phase plus a separate heterogeneous polymeric catalyst phase. The mixture is heated at 50° C. for 2 h. The reaction is monitored by collecting samples, which are analyzed by HPLC. The 9-fluorenone is 99.5% consumed within 2 h. The product after 2 h contains 96.83 area % of 9,9-bis-(4-hydroxyphenyl)fluorene, 2.44 area % of 9-(2-hydroxyphenyl)-9-(4-hydroxyphenyl)fluorene and 0.72 area % of an adduct containing two fluorene units and three phenolic units by HPLC (analytical method 3).

D. EVALUATION OF MERCAPTOSULFONIC ACID POLYMER (PMBSA-SU) FOR THE REACTION OF PHENOL WITH FLUORENONE

To a 4-dram vial equipped with a stirring bar is added 4.32 g of a 20.8:1 molar ratio mixture of phenol:fluorenone and 0.26 g (6% by weight of the reactant solution) of the polymer of Example 21B (PMBSA-SU). The reaction mixture consists of a homogeneous liquid phase plus a separate heterogeneous polymer catalyst phase. The mixture is heated to 50° C. for 5 h. The progress of the reaction is followed by HPLC. At the end of 2 h, 67% of the fluorenone is consumed, and 85% at the end of 5 h. At the end of 5 h, the reaction mixture contains 97.09 area % of 9,9-bis-(4-hydroxyphenyl)fluorene, 2.25 area % of 9-(2-hydroxyphenyl)-9-(4-hydroxyphenyl)fluorene and 0.66 area % of an adduct containing two fluorene units and three phenolic units by HPLC analysis.

Results for the evaluation of various polymer mercaptosulfonic acids for condensing phenol with fluorenone are given in Table X.

TABLE X

CONVERSION OF FLUORENONE (%) USING 6% BY WEIGHT OF POLYMERIC CATALYSTS AT 50° C.

| Resin | Reaction time (h) | | | | |
|---|---|---|---|---|---|
| | 0 | 2 | 4 | 5 | 7 | 18 |
| PMBSA-MER | 0 | 99.5 | | | | |
| PMBSA-SU (PVBC) | 0 | 67 | | 85 | | |
| PMBSA (PVBC) | 0 | 66 | | | | |
| XEMSA-5C (Amberlite ™ XE-305) | 0 | 36 | | 76 | | |
| XEMSA (Amberlite ™ XE-305) | 0 | 49 | | 75 | 82 | |
| Dowex* 50 (DMT promoted) | 0 | | | 17 | | 73 |

*Trademark of The Dow Chemical Company.

EXAMPLE 24

EVALUATION OF THE MERCAPTOSULFONIC ACID POLYMERS IN THE REACTION OF PHENOL WITH ACETONE

To a 4 dram vial equipped with a stirring bar is added 4.33 g of a 14:1 molar ratio mixture of phenol to acetone and 0.26 g (6% by weight of the reactant solution) of the appropriate mercaptosulfonic acid polymer. The reaction mixture typically consists of a homogeneous liquid phase plus a separate heterogeneous polymer catalyst phase. The mixture is heated to and allowed to react at 50° C. The reaction is monitored throughout the reaction period by collecting samples and analyzing by HPLC. HPLC analysis (analytical method 3) shows the following acetone % conversion data (based upon the quantity of bisphenol A produced) for the different catalysts are given in Table XI:

TABLE XI

% ACETONE CONVERSION (BASED UPON BISPHENOL A PRODUCED)

| Resin | Reaction time (h) | | | | | |
|---|---|---|---|---|---|---|
| | 0.0 | 1.0 | 2.25 | 2.5 | 4.0 | 5.0 |
| Dowex* 50WX4, 25% DMT promoted | 0 | | 18 | | 44 | |
| PMBSA (from uncrosslinked PVBC) | 0 | | 35 | | 60 | 75 |
| XEMSA-5C (DF ≈ 0.20) | 0 | | 38 | | | 82 |
| XEMSA (DF ≈ 0.28) | 0 | | 23 | | | 32 |
| PMBSA-SU | 0 | 2 | | 9 | | |
| PMBSA-MER (2% crosslinked, 200–400 mesh) | 0 | 66 | | 88 | | |

*Trademark of The Dow Chemical Company
DMT is 2,2-dimethylthiazolidine

EXAMPLE 25

A. PREPARATION OF BHPF; METHYLENE CHLORIDE AZEOTROPE TO REMOVE WATER; PRECIPITATION FROM METHYLENE CHLORIDE; 5.75:1 MOLAR RATIO OF PHENOL TO 9-FLUORENONE; COPRECIPITATION WITH TETRACHLOROETHYLENE

To a reactor (isothermal stirred batch reactor; reactor design 4) is charged 75.0 g (0.80 mole) of phenol and 24.98 g (0.1386 mole) of 9-fluorenone. The mixture is heated to 40° C. and catalyst (0.973 g, 0.0062 mole, 3-mercaptopropanesulfonic acid) is charged to the reactor. Heating is continued. The course of the reaction is followed by HPLC (analytical method 3) At 30% conversion, methylene chloride (15 g) is added to the reaction mixture so as to keep the mixture stirrable and to use a water/methylene chloride azeotrope (about 180 mm Hg, T=37° C.) to remove water of reaction. The reaction mixture is cooled at the end of the reaction (nearly complete fluorenone consumption, >99% of theoretical water) to increase the amount of crystalline precipitate.

The progress of the run is given in Table XII.

The reaction mixture (~97% selectivity to 4,4-BHPF, little unreacted fluorenone) is split into two parts. The first fraction (53.3 g) is filtered. The filter cake is washed with methylene chloride (49 g) and then with hot water (55 g). The recovery is 6.4 g (first crop) and 0.6 g (second crop) of white crystals, corresponding to 99% purity 4,4-BHPF (33% recovery).

To the remainder of the mixture (70.3 g) is added 61 g of tetrachloroethylene. The crystals are removed by filtration and the filter cake is washed with 50 g of tetrachloroethylene and then with 115 g of hot water. The recovered product weighs 11.5 g (43% recovery, 99% as 4,4-BHPF, white solid).

These results show that use of tetrachloroethylene, in combination with methylene chloride, gives higher recovery of 99% pure 4,4-BHPF).

TABLE XII

| Time h:min | Temp. °C. | mm. Hg | Observations, Actions |
|---|---|---|---|
| 0:0 | 37 | 760 | Add MPSA; turns orange, then dark green brown |
| 0:20 | 36 | 760 | Color light brownish |
| 0:40 | 36 | 760 | Sample taken |
| 1:15 | 36 | 760 | Seed crystal added |
| 2:10 | 36 | 760 | Sample taken |
| 2:28 | 36 | 760 | Methylene chloride (15 g) and seed crystal added; no crystallization; temp. raised to 45° C. |
| 2:30 | 37 | ~180 | Sample taken; seed crystal not dissolving |
| 3:10 | 45 | ~180 | Heater set at 40° C. |
| 3:30 | 40 | ~180 | Seed crystals added |
| 3:50 | 40 | ~180 | Mixture hazy |
| 4:30 | 40 | ~180 | Mixture hazy |
| 5:10 | 40 | ~180 | Sample taken |
| 6:43 | 40 | 760 | Vacuum turned off, stirrer speed increased |
| 9:30 | 40 | 760 | Sample taken; methylene chloride (~20 g) added to mixture; stirrer speed increased; heater turned off |

B. USE OF METHYLENE CHLORIDE AZEOTROPE TO ACCELERATE REACTION; 5.75:1 MOLAR RATIO OF PHENOL TO 9-FLUORENONE

To a reactor (reactor design 5) is charged 75.0 g (0.80 mole) of phenol, 24.98 g (0.1386 mole) of 9-fluorenone and 15.0 g of methylene chloride. The mixture is heated to 40° C. Catalyst (3-mercaptopropanesulfonic acid, 0.757 g, 0.0049 mole) is charged to the reactor and the mixture is stirred. The reaction is followed by HPLC (analytical method 3).

At the end of the reaction, methylene chloride is added to produce a mixture of about 30:30:~30% by weight of methylene chloride:BHPF:phenol and the mixture is heated to dissolve the crystalline material. Additional methylene chloride is added to the solution and the solution is cooled to promote crystalliza-tion.

The progress of the reaction is shown in Table XIII.

At the end of the reaction, half of the resulting mixture is filtered and the filter cake is washed with 64 g of methylene chloride. The first crop of BHPF weighs 7.0 g (dried overnight at 40° C.) and is white with very little pink coloration. A second crop of crystals is collected and washed with 28 g of methylene chloride. Weight, 4.1 g (dried overnight at 40° C., slightly pink), about 99% purity after a further washing with water.

The remainder of the reaction mixture is filtered and the filter cake is washed with methylene chloride and hot water and dried overnight at 40° C. The recovery is 14 g (51% overall recovery), about 99% purity by HPLC.

TABLE XIII

| Time h:min | Temp. °C. | mm. Hg | Observations, Actions |
|---|---|---|---|
| 0:0 | 45 | 760 | Add MPSA, turns dark |
| 0:09 | 45 | 760 | Add about 20 g of methylene chloride; color is dark brownish |
| 0:30 | 45 | 760 | Lighter brown; reduce pressure to ~180 mm |
| 1:00 | 45 | ~180 | Seed crystal added; no crystallization observed |
| 2:00 | 45 | ~180 | Seed crystal added; no crystallization observed |
| 3:00 | 45 | ~180 | Sample taken; seed crystal added; crystal not dissolving |
| 3:45 | 45-> | ~180 | Heater set at 40° C.; crystals forming |
| 4:00 | 40 | ~180 | More crystals forming |
| 6:30 | 40 |  | Sample taken; solid crystalline mass; stirring ineffective; yellowish color; vacuum turned off |
| 19:00 | 40 | 760 | Sample taken; ~50–70% of BHPF crystallized; 33% by weight of methylene chloride added; temperature increased to 58° C. |
| ~20:30 | 58 | 760 | Temperature lowered to <40° C.; methylene chloride added to 80% make up by weight of mixture |
|  | 24 | 760 | Cooled to room temperature |

C. REACTION USING METHYLENE CHLORIDE AS SOLVENT: 3.5:1 MOLAR RATIO OF PHENOL TO FLUORENONE

Phenol (30.0 g, 0.32 mole), 9-fluorenone (16.41 g, 0.0911 mole) and 15.0 g of methylene chloride are charged to a reactor (reactor design 4). The mixture is stirred and heated at 40° C. and 1.122 g (0.0072 mole) of MPSA is added over 1 min. Heating is continued at 41° C. for the duration of the reaction. The following observations are made during the run:

| Time (h) | Temp. (°C.) | Observations, Actions |
|---|---|---|
| 0 | 41 | MPSA added; turns orange to brown to dark brown within about 30 sec |
| 0.18 | 41 | purple color |
| 0.5 | 41 | sample taken |
| 1.5 | 41 | sample taken |
| 1.67 | 41 | orange mixture seeded with crystals |
| 3 | 41 | sample taken; heater off; left overnight |
| 4 | 41 | heater off |
| 6 | room | sample taken; ~80% conversion; more 2:3 adduct than 2,4 adduct |

The crystalline solid is removed by filtration and the filter cake is washed with methylene chloride. A second crop of crystals is recovered from the mother liquors. The yield is 0.86 g (first crop), 8.66 g (second crop), 3.5 g (third crop), overall 13 g (41%), >99% purity by HPLC (method 3).

C. PHENOL:FLUORENONE MOLAR RATIO OF 15:1; MPSA CATALYST; PHENOL REMOVED BY DISTILLATION; CRYSTALLIZED FROM METHYLENE CHLORIDE

To a mixture of phenol and fluorenone (15:1 molar ratio), heated to about 65° C., is added about 0.0498 equivalent of 3-mercaptopropanesulfonic acid (with respect to fluorenone). The resulting mixture is heated at about 65° C. for 2 h, after which the reaction mixture is washed with water (14 times the volume of the mixture) to remove MPSA. The washed reaction mixture is distilled to a phenol:BHPF weight ratio of 1:1 and cooled to bring about crystallization of BHPF. Crystalline material is removed by filtration, washed with methylene chloride, washed with water and dried to give BHPF (99.8% by weight of 4,4-isomer).

EXAMPLE 26

CONDENSATION OF PHENOL AND ACETONE TO PRODUCE 2,2-BIS-(4-HYDROXYPHENYL) PROPANE

A. FEED CONTAINING 6% BY WEIGHT OF ACETONE, PLUS WATER, SOLUBLE CATALYST; BATCH REACTION

The reaction is carried out in a 2-L jacketed baffled resin pot, equipped with a condenser and nitrogen purge. Isothermal temperature control is provided by a fluid material, circulated through the reactor jacket. Stirring is provided by a Lightnin Labmaster TS2510 stirrer, equipped with an A-310 impeller.

To the reactor is charged 1200 g of feed, containing 90.0% by weight of phenol, 6.0% by weight of acetone, 1.8% by weight of water and 2.2% by weight of MPSA. The mixture is heated at 35° C. At the end of 2 hours' heating, crystallization occurs in the reaction mixture. The reaction is continued 1 h more, at the end of which 80% of the acetone is reacted (HPLC). The reaction mixture is removed from the reactor and filtered. The weight of recovered crystals is 17%, consisting of a 1:1 adduct of BPA:phenol (molar ratio). The crystalline adduct is washed with phenol. The washed adduct contains 57.7% by weight of 4,4-bisphenol, 160 ppm of 2,4-bisphenol, 200 ppm of trisphenol, 2270 ppm of other trace bisphenolic impurities and 1170 ppm of MPSA, the balance being phenol. The mother liquor contains 8.44% by weight of 4,4-bisphenol, 0.26% by weight of 2,4-bisphenol, 0.13% by weight of trisphenol 0.62% by weight of other bisphenolic impurities, 0.81% by weight of acetone, 2.95% by weight of water and 2.78% by weight of MPSA, the balance being phenol.

B. REACTION USING RECYCLED MOTHER LIQUORS

The mother liquor from (A) is charged to a rotary evaporator with make-up phenol (181 g). The evaporator is heated at 50° C. for about 30 min, at the end of which the conversion of acetone is 90%. Pressure is reduced to 10 mm Hg absolute for 30 min, at the end of which the mixture contains 1.4% by weight of water. The acetone content is below the detection limit.

The dried mother liquor is returned to the reactor, along with make-up phenol, acetone, water and MPSA to give a mixture containing 92.0% by weight of phenol, 4.0% by weight of acetone, 1.8% by weight of water and 2.2% by weight of MPSA. The total mass corresponds to (A), minus the weight of samples removed. The mixture is stirred and heated at 35° C. for 3 hr. Crystallization of BPA is observed after the initial 30 min of heating. At the end of 3 hours' heating, acetone conversion is 80%. The reaction mixture is processed as in (A). Recycling of the mother liquors is repeated for 12 cycles. Results are given in Tables XIV and XV.

These experiments demonstrate that catalyst and unreacted materials can be recovered and recycled without adversely affecting the process and that results for successive runs are generally consistent and predictable.

C. REACTION USING 10% BY WEIGHT OF ACETONE IN THE FEED WITH 3% BY WEIGHT OF WATER

An experiment is done as in (A), using 1200 g of feed, containing 85.5% by weight of phenol, 10.0% by weight of acetone, 3.0% by weight of water and 2.2% by weight of MPSA. The reaction is done at 25° C. Crystalline BPA is visible after 13 h at this temperature. At the end of 24 h, the conversion of acetone is 40%.

Crystalline product, removed from the reaction mixture by filtration, constitutes 15% of the mixture. The crystals, a 1:1 adduct of BPA:phenol, are washed with phenol. The washed crystals contain 51.8% by weight of the 4,4-isomer, 60 ppm of 2,4-isomer, <20 ppm of trisphenol, 690 ppm of other trace bisphenols and 840 ppm of MPSA, the remainder being phenol. The mother liquors contains 6.73% by weight of 4,4-isomer, 0.15% by weight of 2,4-isomer, 0.08% by weight of trisphenol, 0.76% by weight of other bisphenols, 5.71% by weight of acetone, 4.97% by weight of water and 2.66% by weight of MPSA, the remainder being phenol.

TABLE XIV

COMPOSITION OF WASHED BISPHENOL A CRYSTALS

| Cycle No. | Crystal % | 4,4-isomer wt. % | 2,4-isomer ppm | Tris-phenol ppm | Other bis-phenol ppm | MPSA ppm |
|---|---|---|---|---|---|---|
| 1 | 17 | 57.7 | 160 | 200 | 2270 | 1170 |
| 2 | 22 | 60.4 | 420 | n/d* | 1730 | 1940 |
| 3 | 17 | 59.7 | 460 | 270 | 2380 | 670 |
| 4 | 18 | 60.7 | 560 | 260 | 2270 | 1440 |
| 5 | 26 | 57.9 | 870 | 410 | 1840 | 1070 |
| 6 | 18 | 59.3 | 790 | 330 | 2050 | 2110 |
| 7 | 18 | 59.3 | 790 | 390 | 2150 | 740 |
| 8 | 19 | 59.6 | 770 | 280 | 2100 | 750 |
| 9 | 22 | 59.4 | 840 | 390 | 2000 | 860 |
| 10 | 31 | 62.5 | 920 | 380 | 2210 | 1060 |
| 11 | 21 | 64.0 | 710 | 350 | 2020 | 1410 |
| 12 | 23 | 63.0 | 770 | 280 | 1900 | 1500 |
| Avg. Cycles 7–12 | 22 ± 5 | 61 ± 2 | 800 ± 70 | 350 ± 50 | 2100 ± 100 | 1100 ± 300 |

*n/d = not detected

TABLE XV

MOTHER LIQUOR COMPOSITIONS

| Cycle No. | 4,4-Isomer wt % | 2,4-Isomer wt % | Tris-phenol wt % | Other bisphen-olics wt % | Ace-tone wt % | Water wt % | MPSA wt % |
|---|---|---|---|---|---|---|---|
| 1 | 8.44 | 0.26 | 0.13 | 0.62 | 0.81 | 2.95 | 2.78 |
| 2 | 7.53 | 0.48 | 0.23 | 0.47 | 0.63 | 2.94 | 2.89 |
| 3 | 8.30 | 0.55 | 0.24 | 0.38 | 0.79 | 2.94 | 2.75 |
| 4 | 8.42 | 0.66 | 0.29 | 0.41 | 0.70 | 2.63 | 2.87 |
| 5 | 8.92 | 0.78 | 0.43 | 0.42 | 0.86 | 2.81 | 2.73 |
| 6 | 8.22 | 0.86 | 0.44 | 0.46 | 0.73 | 3.06 | 2.84 |
| 7 | 7.92 | 0.87 | 0.42 | 0.46 | 0.66 | 3.09 | 2.83 |
| 8 | 8.03 | 0.91 | 0.44 | 0.49 | 0.58 | 3.07 | 2.84 |
| 9 | 8.09 | 0.84 | 0.36 | 0.45 | 0.72 | 3.02 | 2.44 |
| 10 | 6.86 | 1.03 | 0.51 | 0.46 | 0.25 | 2.64 | 2.92 |
| 11 | 7.59 | 0.78 | 0.33 | 0.44 | 0.51 | 3.01 | 2.69 |
| 12 | 7.87 | 0.84 | 0.39 | 0.42 | 0.27 | 3.17 | 3.14 |
| Avg. Cycles 7–12 | 7.7 ± 0.5 | 0.88 ± 0.09 | 0.41 ± 0.06 | 0.45 ± 0.02 | 0.5 ± 0.2 | 3.0 ± 0.2 | 2.8 ± 0.2 |

EXAMPLE 27

Preparation of a Representative [(Mercaptoalkyl)(Sulfo)Phenylalkyl] Sulfonated Polystyrene Catalyst (Designated DPMSA-MER3C)

A. Alkylation

A 15.00 g sample of 200–400 mesh chloromethylated polystyrene/2% divinylbenzene co-polymer beads (approximately 4.3 mmol Cl/g resin, approximately 64.5 mmole Cl) known in the art as a Merrifield resin (commercially available from Fluka Chemie AG) is added to a round bottom glass flask (reactor) under a pad of plant nitrogen with a sodium hydroxide scrubber attached (to trap evolved HCl). (3-Bromopropyl)benzene (102.7 g, 78.4 mL, 8.0 equivalents) is added to the dry resin beads. Dried (over 3 Angstrom molecular sieves) nitrobenzene (50 mL) is added, and the beads are slowly stirred at room temperature to allow for swelling of the beads. The reactor is cooled to 0° C. in an ice water bath. A 20 mL sample of 1.0M aluminum chloride in nitrobenzene commercially available from Aldrich Chemical Co. is slowly added via syringe to the cold polymer slurry with rapid stirring over approximately 10 minutes. The mixture turns dark red as soon as the aluminum chloride solution is added and exotherms to approximately 4° C. within the first 15 minutes of reaction with HCl being evolved from the solution. After the addition of the $AlCl_3$/nitrobenzene solution is complete, the mixture is slowly stirred at 0° C. for 2–3 hours, then is removed to room temperature and slowly stirred overnight. The mixture is slowly poured onto ice to quench the aluminum chloride. Then the beads are separated using a glass-fritted funnel with vacuum filtration. The beads are sequentially washed with water, acetone, dichloromethane, methanol, dilute aqueous hydrochloric acid, water and methanol, then are dried overnight in a vacuum oven at 70° C. (dry mass 23.52 g).

B. Sulfonation

The polymer beads from Example 27A (23.30 g, estimated 161.3 mmole of phenyl groups) are added to a glass reactor with addition funnel and NaOH scrubber attached. Dichloromethane (100 mL) is added to the flask and the beads are allowed to swell (rapid swelling is observed). The slurry is cooled to 0° C. in an ice water bath. Chlorosulfonic acid (37.6 g, 21.4 mL, 320 mmole, approximately 2.0 equivalents per equivalent phenyl groups) is slowly added dropwise over approximately 2 hours to the polymer slurry at 0° C. The mixture is allowed to slowly warm to room temperature overnight in the water bath. The mixture is slowly poured onto ice to quench the excess chlorosulfonic acid, then the beads are separated using a glass-fritted funnel with vacuum filtration. The beads are then washed extensively with water. Water is added to make a slurry, then solid sodium bicarbonate is slowly added in small portions over approximately 2 hours until no more bubbling is observed (all active acid sites neutralized). The mixture is allowed to stand 3 days in the aqueous sodium bicarbonate solution (some additional bead swelling observed over this time period). The beads are washed with water and transferred to a glass reactor with 100 mL of water. The beads are then heated to 70–80° C. over 2 hours to ensure hydrolysis of any residual sulfonyl chloride groups.

C. Thiolation

The aqueous polymer slurry from Example 27B is cooled to room temperature. Sodium bicarbonate is slowly added until the slurry is neutral (no bubbling observed), then additional sodium bicarbonate (27.1 g, 323 mmol) is added to the aqueous bead slurry. Thiolacetic acid (24.6 g, 23.1 mL, 323 mmol) is added to an addition funnel. The reactor is evacuated and refilled with nitrogen several times to minimize the air content. The thiolacetic acid is slowly added over approximately 15–20 minutes to the aqueous bead slurry with rapid stirring. The addition rate is adjusted to control the effervescent evolution of carbon dioxide which is formed in the neutralization process. After the thiolacetic acid addition is complete, the mixture is heated to 70° C. and is allowed to react overnight with minimal stirring. The mixture is then cooled to room temperature and the beads are collected by filtration using a fritted-glass funnel. The beads are washed extensively with water, then with dichloromethane, and then washed again with water. The beads are transferred back to the glass reactor, then concentrated (12 molar) hydrochloric acid (100 mL) is added. The mixture is heated with mild stirring to 50° C. for 4–5 hours, then is cooled to room temperature. Deionized water (100 mL) is added and the beads are again collected by filtration using a fritted-glass funnel. The beads are washed with water, then are washed extensively (approximately 500 mL) with dilute (approximately 3 molar) aqueous hydrochloric acid. The beads are then washed again with deionized water and finally are washed with methanol to displace the water and shrink the polymer beads. The beads are dried overnight in a vacuum oven at 70° C. (dry mass 34.17 g). The final polymer catalyst is designated as DPMSA-MER3C.

D. Preparation of Three-Carbon DPMSA Polymer From Merrifield Resin Beads

Another mercaptosulfonic acid polymer is prepared using the procedure of steps A–C of Example 27, except using a chloromethylated polystyrene resin (2% divinylbenzene, 200–400 mesh, approximately 4.3 mmol Cl/g resin), a Merrifield resin commercially available from Fluka Chemie AG as the polymeric support and (3-bromopropyl)benzene in the alkylation step of the reaction. The resulting polymer is identified as DPMSA-MER3C.

E. Preparation of Three-Carbon DPMSA Polymer From Chloromethylated Gel-Resin Beads Another mercaptosulfonic acid polymer is prepared using the procedure of steps A–C of Example 27, except using a chloromethylated 1.5% crosslinked polystyrene gel-resin (−30+70 mesh, approximately 4.3 mmol Cl/g resin) as the polymeric support and (3-bromopropyl)benzene in the alkylation step of the reaction. This polymer is identified as DPMSA-1.5×3C.

F. Preparation of Two-Carbon DPMSA Polymer From Chloromethylated Gel-Resin Beads Another mercaptosulfonic acid polymer is prepared using the procedure of steps A–C of Example 27, except using a chloromethylated 1.5% crosslinked polystyrene gel-resin (−30+70 mesh, approximately 4.3 mmol Cl/g resin) as the polymeric support and (2-bromoethyl)benzene in the alkylation step of the reaction. This polymer is identified as DPMSA-1.5×2C.

G. Preparation of three Carbon DPMSA from 6% Crosslinked Macroporous Resin

Another mercaptosulfonic acid polymer is using the procedure of steps A–C of Example 27, except using a chloromethylated 6% crosslinked macroporous polystyrene resin (approximately 30–70 mesh, approximately 4.3 mmol Cl/g resin) as the polymeric support and (3-bromopropyl)benzene in the alkylation step of the reaction. This polymer is identified as DPMSA-6/42-3C.

H. Preparation of three Carbon DPMSA from 6.5% Crosslinked Gel Resin

Another mercaptosulfonic acid polymer is using the procedure of steps A–C of Example 27, except using a chloromethylated 6.5% crosslinked uniform particle size polystyrene gel-resin (380 micron, approximately 4.3 mmol Cl/g resin) as the polymeric support and (3-bromopropyl)benzene in the alkylation step of the reaction. This polymer is identified as DPMSA-6.5×3C.

EXAMPLE 28

EVALUATION OF CATALYSTS IN CONTINUOUS PROCESSES

A fixed bed downflow reactor, having a volume of 10-mL, is constructed from a vertical tube, filled with catalyst.

External to the catalyst bed is a preheater area, packed with glass wool. Ancillary equipment includes a pressure regulator, relief valve, pump and heater for the feed. The feed is heated by heating fluid, circulated through the feed pot, and is kept under a nitrogen pad.

The feed is phenol (99.9%) and fluorenone (~99%) in a 21:1 molar ratio.

The heating fluid, heating tape and reactor are turned on. The selected catalyst is slurried in phenol at ~45° C. Catalyst-phenol mixture is pipetted into the reactor, at the bottom of which a plug of glass wool/glass beads is placed to prevent catalyst from leaving the reactor. The phenol:fluorenone is added to the feed pot at 55° C. The pressure is adjusted to ~0.34 bars.

Phenol:fluorenone feed is introduced into the reactor and the composition of the effluent from the reactor is followed by HPLC.

The following results are obtained:

TABLE XVI

| conversion time (h) | % fluorenone conversion |
| --- | --- |
| PMBSA-Mer catalyst (Example 9C) at 50° C.: productivity 1.4 g BHPF/g cat h | |
| 0.33 | 99.7 |
| 28 | 100.0 |
| 53 | 100.0 |
| 69 | 99.7 |
| 89 | 99.9 |
| 113 | 100.0 |
| 137 | 99.8 |
| 144 | 99.6 |
| 162 | 99.6 |
| selectivity 98% 4,4-BHPF | |
| PMBSA-XEBr (Example 9D) at 69° C.: productivity 0.6 g BHPF/g cat h | |
| 2 | 99.8 |
| 15 | 100.0 |
| 39 | 100.0 |
| 63 | 98.9 |
| 79 | 99.0 |
| 103 | 95.5 |
| 127 | 87.1 |
| 164 | 83.4 |
| selectivity 98% 4,4-BHPF | |
| PMBSA-XECl (Example 9E) at 56° C.: productivity 1.48 g BHPF/g cat h | |
| 2 | 99.2 |
| 27 | 99.1 |
| 63 | 99.3 |
| 87 | 98.7 |
| 111 | 98.9 |
| 135 | 98.6 |
| 159 | 98.3 |
| 164 | 98.0 |
| selectivity 98% 4,4-BHPF | |
| XEMSA-11C (Example 22D) at 60° C.: | |
| 5 | 99.2 |
| 17 | 94.4 |
| 41 | 92.2 |
| 65 | 91.0 |
| DPMSA-MER3C (Example 27D) at 50° C.: selectivity 98% p,p-BHPF productivity 4 lb BHPF/lb catalyst/hour = 4 kg/kg/h | |
| 20 | 99.9 |
| 24 | 99.9 |
| 39 | 99.9 |
| 48 | 100.0 |
| 66.5 | 100.0 |
| 75.5 | 98.9 |

TABLE XVI-continued

| conversion time (h) | % fluorenone conversion |
| --- | --- |
| 99.5 | 99.1 |
| 103 | 98.6 |
| 104 | 98.7 |
| XEMSA-5C (Example 22) at 55° C.: selectivity 98% p,p-BHPF productivity 0.43 lb BHPF/lb catalyst/hour = 0.43 kg/kg/h | |
| 4 | 99.7 |
| 22 | 100.0 |
| 46 | 100.0 |
| 70 | 100.0 |
| 77 | 99.7 |
| 94 | 99.7 |
| 118 | 99.7 |
| 142 | 99.5 |
| 144 | 99.4 |
| 168 | 99.3 |
| 192 | 99.0 |
| 216 | 99.0 |
| 240 | 98.6 |
| 264 | 98.6 |
| DPMSA-XE3C (Example 27A-C) at 56° C.: selectivity 98% 4,4-BHPF | |
| 30 | 98.0 |
| 48 | 95.1 |
| 72 | 94.7 |
| 96 | 92.3 |
| 123 | 87.3 |
| 144 | 86.1 |
| 170 | 83.8 |
| 240 | 77.1 |

These results show that PMBSA, XEMSA, and DPMSA catalysts of the invention can exhibit stability over time, thus, have very useful lifetimes.

EXAMPLE 29

CONTINUOUS PROCESS FOR MAKING BHPF USING MERCAPTOPROPANESULFONIC ACID CATALYST

The reactor comprises a three-staged continuous reactor (isothermal perfectly stirred type). The reaction is run at 46° C. at a 21:1 molar ratio of phenol:fluorenone (98%, Aldrich), the amount of MPSA being 0.05–0.07 equivalent of MPSA:mole of fluorenone. The composition of the products is followed by HPLC.

The reaction is continued for 228 h, at the end of which fluorenone conversion is 99.95% (reactor 2) or 99.9% (reactor 1) and selectivity to 4,4-BHPF is 98.32% (reactor 2) or 95.2% (reactor 1).

EXAMPLE 30

EVALUATION OF CATALYST OF EXAMPLE 22D (XEMSA-5C) IN CONTINUOUS PROCESS FOR MAKING BISPHENOL A

The reactor comprises a vertical upflow column of stainless steel tubing, packed with resin atop a screen and glass beads. The column is heated by a water jacket. The progress of the reaction is followed as above by HPLC.

The following results are obtained:

TABLE XVII

| Test | | 25% promoted Dowex ™ 50Wx4 | XEMSA-5C Example 22D |
|---|---|---|---|
| Acid capacity | | | |
| dry | meq/g | 4.0 | 3.5 |
| wet | meq/mL | 0.84 | 1.17 |
| Swell test phenol/water vol. | | 0.55 | 0.72 |
| Reaction tests 30 min res. time | | | |
| 4% acetone, 65° C. | | | |
| 4,4 | % by wt | 12.7 | 14.0 |
| conversion | | 0.83 | >0.95 |
| productivity | | 8.2 | 9.0 ± 0.2 |
| 2,4/4,4 | | 0.28 | 0.024 ± 0.001 |
| 6% acetone, 65° C. | | | |
| 4,4 | % by wt | ~15 | 19.1 ± 0.6 |
| conversion | | ~0.7 | 0.92 |
| productivity | | ~10 | 12.2 ± 0.4 |
| 2,4/4,4 | | ~0.27 | 0.025 ± 0.003 |
| 4% acetone, 55° C. | | | |
| 4,4 | | 10.7 | 13.0 ± 0.1 |
| conversion | | 0.67 | 0.92 ± 0.01 |
| productivity | | 7.2 | 8.3 ± 0.06 |
| 2,4/4,4 | | 0.21 | 0.019 ± 0.001 |

EXAMPLE 31

PREPARATION OF BISPHENOL F

Phenol and formaldehyde are reacted to produce bisphenol F. Similar results are obtained.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and without departing from the spirit and scope thereof, can make various changes and modifications of the invention to adapt it to various usages and conditions.

EXAMPLE 32

Alternate Preparation of a Representative [(Mercaptoalkyl)(Sulfo)-Phenylalkyl] Sulfonated Polystyrene Catalyst (Designated DPMSAA-0.25–1.5×2C)

A Preparation of (2-Bromoethyl)benzyl Chloride (A1) In an extension of the procedure described by Selva, M; Trotta, F.; and Tundo, P. *Synthesis*, 1991, 1003–1004, (2-bromoethyl)benzylchloride is prepared by the following procedure:

Concentrated sulfuric acid (132 mL) is slowly added to ice cold deionized water (66 mL) in a 1 L three-necked glass reactor fitted with a mechanical stirrer, reflux condenser, and temperature probe. The reactor containing the sulfuric acid solution is cooled in an ice bath, then (2-bromoethyl) benzene (92.5 g, 0.50 mol) is added followed by 50 percent tetrabutylammonium chloride in water (10 g of solution), paraformaldehyde (20.0 g, 0.666 mol, 1.33 equivalents), and finally sodium chloride (80.0 g, 1.37 mol, 2.74 equivalents).

The slurry is stirred at approximately 1000 rpm (very vigorous) and heated to 80° C. for 2.25 hours. The reaction is less than 50 percent complete as determined by gas chromatographic analysis. Additional paraformaldehyde (20.0 g, 0.666 mol, 1.33 equivalents) is added and the mixture is stirred (600–700 rpm) an additional 3.5 hours at 80° C. The reaction is approximately 50 percent complete as determined by gas chromatographic analysis. The mixture is allowed to cool and is transferred to a separatory funnel. The organic phase is separated and saved for further reaction.

(A2) Alternatively, (2-Bromoethyl)benzene (92.5 g, 0.50 mol), concentrated (12 molar) hydrochloric acid (125 mL, 1.5 mole HCl, 3 equivalents HCl), and paraformaldehyde (22.5 g, 0.75 mol, 1.5 equivalents) are added to a 1 L three-necked glass reactor fitted with a mechanical stirrer, addition funnel, and temperature probe. Concentrated sulfuric acid (111 mL, approximately 205 g, approximately 4 equivalents of sulfuric acid) is added to the addition funnel. A small portion (approximately 10–15 mL) of the sulfuric acid is added to the reaction mixture from the addition funnel and the slurry is heated to 80° C. with stirring at approximately 1000 rpm. After the reaction reaches 80° C., the remaining concentrated sulfuric acid is added dropwise over 3 hours. After an addition 1 hour reaction time, the reaction is less than 50 percent complete as determined by gas chromatographic analysis. The mixture is allowed to cool and is transferred to a separatory funnel. The organic phase is separated and saved for further reaction.

The combined products from Example 32, parts A1 and A2 containing unreacted (2-bromoethyl)benzene and chloromethylated (2-bromoethyl)benzene products (mixture of isomers) are further chloromethylated according to the procedure-described in part A1. The reaction is performed using sufficient time and reagent (paraformaldehyde, sodium chloride, sulfuric acid) charges to completely consume the (2-bromoethyl)benzene starting material, giving a mixture of (2-bromoethyl)benzyl chloride isomers along with higher-boiling by-products. The mixture of (2-bromoethyl) benzyl chloride isomers is isolated by oil-pump vacuum bulb-to-bulb Kugelrohr distillation (up to 140–145° C.). The isolated product is a water-white oil which solidifies upon standing at room temperature. Gas chromatography analysis shows that unreacted (2-bromoethyl)benzene and the higher boiling by-products are essentially absent from the distilled (2-bromoethyl)benzyl chloride isomers product.

B. Alkylation

Styrene/divinylbenzene co-polymer resin beads (10.00 g, −30+70 mesh, 1.5 percent divinylbenzene, approximately 96.0 mmole styrene repeat units) are added to a round bottom glass flask (reactor) under a pad of nitrogen with a sodium hydroxide scrubber attached (to trap evolved HCl). A solution of (2-bromoethyl)benzyl chloride (mixture of aromatic ring isomers, predominately para) (10.0 g, 0.238 equivalents based upon styrene repeating units) in 1,2-dichloroethane (25 mL) is added to the dry resin beads. The beads are allowed to swell for approximately 5–10 minutes, then additional 1,2-dichloroethane (35 mL) is added to the swollen beads. Anhydrous tin(IV) chloride (2.5 mL, approximately 5.57 g, approximately 21.4 mmol) is slowly added via syringe to the polymer slurry at room temperature over approximately 10 minutes with rapid stirring. The mixture turns light yellow when the tin(IV) chloride is added. The mixture is slowly warmed (in 5° C. increments) to 40° C. over approximately 30 minutes and is allowed to react at 40° C. for 1 hour. At this time the light orange mixture is slowly warmed (in 5° C. increments) to 60° C. over approximately 1 hour 30 minutes and is allowed to react overnight at 60° C. with slow stirring. After overnight reaction, the mixture is cooled to room temperature and is quenched by slowly adding methanol to the well-stirred polymer slurry. The beads are separated from the solution using a glass-fritted funnel with vacuum filtration. The beads are sequentially washed (three portions each) with dichloromethane, water, tetrahydrofuran, and methanol, then the beads are dried overnight in a vacuum oven at 80° C. (dry mass 13.89 g). Theoretical mass yield=14.49 g. Alkylation yield (by mass uptake)=87 percent. Approximate degree of polymer functionalization (by mass yield)=0.21.

C. Sulfonation

The polymer beads from Example 32B (13.89 g, estimated 116 mmole of phenyl groups) are added to a glass reactor with addition funnel and NaOH scrubber attached. Dichloromethane (75 mL) is added to the flask and the beads are allowed to swell (rapid swelling is observed). The slurry is cooled to approximately 3–5° C. in an ice water bath. Chlorosulfonic acid (11.7 mL, approximately 20.5 g, approximately 176 mmol, approximately 1.5 equivalents per equivalent of phenyl groups) is slowly added dropwise over approximately 30 minutes to the cold polymer slurry with stirring. The mixture is allowed to react at approximately 3–5° C. in an ice water bath for 1 hour. The mixture is removed from the ice bath and allowed to warm to room temperature over 2 hours 45 minutes. At this time, the polymer slurry is again cooled to 3–5° C. in an ice water bath, and water is slowly added with rapid stirring to quench the excess chlorosulfonic acid. The beads are separated using a glass-fritted funnel with vacuum filtration. The beads are then washed extensively with water. Water is added to make a slurry, then solid sodium bicarbonate is slowly added in small portions with stirring until no more bubbling is observed (all active acid sites are neutralized). The beads are washed with water and transferred back to the glass reactor with 100 mL of water. The beads are then heated to 60–70° C. over 2 hours to ensure hydrolysis of any residual sulfonyl chloride groups.

D. Thiolation

The aqueous polymer slurry from Example 32C (estimated approximately 20 mmole Br) is cooled to room temperature. Sodium bicarbonate is slowly added until the slurry is neutral (no bubbling observed), then additional sodium bicarbonate (5.30 g, 63.0 mmol, approximately 3 equivalents relative to estimated bromine content in beads) is added to the aqueous bead slurry. Thiolacetic acid (4.5 mL, approximately 4.8 g, approximately 63 mmol, approximately 3 equivalents relative to estimated bromine content in beads) is added to an addition funnel. The reactor is evacuated and refilled with nitrogen several times to minimize the air content. The thiolacetic acid is slowly added over approximately 10–15 minutes to the aqueous bead slurry at room temperature with rapid stirring. The thiolacetic acid addition rate is adjusted to control the effervescent evolution of carbon dioxide which is formed in the neutralization process. After the thiolacetic acid addition is complete, the mixture is heated to 70° C. and is allowed to react overnight with minimal stirring. The mixture is then cooled to room temperature and the beads are collected by filtration using a fritted-glass funnel. The beads are washed extensively with water, then with dichloromethane (optional), and then washed again with water. The beads are transferred back to the glass reactor, then concentrated (12 molar) hydrochloric acid (100 mL) is added. The mixture is heated with mild stirring to 50° C. for 2–3 hours, then is cooled to room temperature. Deionized water (100 mL) is added and the beads are again collected by filtration using a fritted-glass funnel. The beads are washed with water, then are washed extensively (approximately 500 mL) with dilute (approximately 3 molar) aqueous hydrochloric acid. The beads are then washed again with deionized water and are transferred to a storage bottle without any additional drying. The final polymer catalyst has a titrated water-wet (water swollen) acid capacity of 0.80 milliequivalent/mL catalyst. The final polymer catalyst is designated as DPMSAA-0.25–1.5×2C E. Preparation of DPMSAA Resin with 0.71 Equivalents Alkylation Another mercaptosulfonic acid polymer is prepared from 1.5 percent crosslinked styrene/divinylbenzene co-polymer beads (−30+70 mesh) using the procedure described in steps B–D of Example 32, except using 0.71 equivalents of (2-bromoethyl)benzyl chloride in the alkylation reaction. Chlorosulfonic acid (2.0 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The mass yield of polymer obtained from the alkylation reaction corresponds to a 83 percent yield in the alkylation reaction and a degree of functionality of 0.59. The final polymer catalyst has a titrated water-wet (water swollen) acid capacity of 0.94 milliequivalent/mL catalyst. The final polymer catalyst is designated as DPMSAA-0.75–1.5×2C.

F. Preparation of DPMSAA Resin with 0.43 Equivalents Alkylation

Another mercaptosulfonic acid polymer is prepared from 1.5 percent crosslinked styrene/divinylbenzene co-polymer beads (−30+70 mesh) using the procedure described in steps B–D of Example 32, except using 0.43 equivalents of (2-bromoethyl)benzyl chloride in the alkylation reaction. Chlorosulfonic acid (2.0 equivalents relative to the calculated total equivalents of phenyl groups in the polymer) was is in the sulfonation reaction. Thiolacetic acid and sodium bicarbonate (3.0 equivalents of each reagent relative to the calculated amount of bromine in the polymer) are used in the thiolation reaction. The mass yield of polymer obtained from the alkylation reaction corresponds to a 81 percent yield in the alkylation reaction and a degree of functionality of 0.35. The final polymer catalyst has a titrated water-wet (water swollen) acid capacity of 0.85 milliequivalent/mL catalyst. The final polymer catalyst is designated as DPMSAA-0.45–1.5×2C.

G. Preparation of DPMSAA with 0.095 Equivalents Alkylation

Another mercaptosulfonic acid polymer is prepared from 1.5 percent crosslinked styrene/divinylbenzene co-polymer beads (−30+70 mesh) using the procedure described in steps B–D of Example 32, except using 0.095 equivalents of (2-bromoethyl)benzyl chloride in the alkylation reaction. Chlorosulfonic acid (1.5 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The mass yield of polymer obtained from the alkylation reaction corresponds to a 99 percent yield in the alkylation reaction and a degree of functionality of 0.094. The final polymer catalyst has a titrated water-wet (water swollen) acid capacity of 0.80 milliequivalent/mL catalyst. The final polymer catalyst is designated as DPMSAA-0.10–1.5×2C.

H. Preparation of DPMSAA with 0.42 Equivalents of (2-Bromoethyl)benzylchloride Alkylation and 0.30 Equivalents of Benzyl Chloride Alkylation Another mercaptosulfonic acid polymer is prepared from 1.5 percent crosslinked styrene/divinylbenzene co-polymer beads (−30+70 mesh) using the procedure described in steps B–D of Example 32, except using 0.42 equivalents of (2-bromoethyl)benzyl chloride and 0.30 equivalents of benzyl chloride in the alkylation reaction. Chlorosulfonic acid (2.0 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The final polymer catalyst has a titrated water-wet (water swollen) acid capacity of 0.94 milliequivalent/mL catalyst. The final polymer catalyst is designated as DPMSAA-0.45/0.30–1.5×2C.

I. Preparation of DPMSAA Resin having 0.423 Equivalents Alkylation

Another mercaptosulfonic acid polymer is prepared from 1.5 percent crosslinked styrene/divinylbenzene co-polymer beads (−30+70 mesh) using the procedure of steps B–D of Example 32, except using 0.423 equivalents of (2-bromoethyl)benzyl chloride in the alkylation reaction and directly carrying the polymer slurry obtained from the alkylation reaction directly on to the sulfonation reaction without any quenching, isolation, or washing steps after the alkylation reaction. Chlorosulfonic acid (1.25 equivalents relative to the total equivalents of phenyl groups present in all reactants) is added directly to the polymer slurry after the alkylation reaction is complete. Workup and subsequent isolation of the product after sulfonation is as in Example 32, except that more extensive washing is required to remove soluble reaction by-products from the polymer slurry. Thiolacetic acid and sodium bicarbonate (3.0 equivalents of each reagent relative to the estimated maximum amount of bromine present in the polymer) are used in the thiolation reaction. The final polymer catalyst has a titrated water-wet (water swollen) acid capacity of 0.78 milliequivalent/mL catalyst. The final polymer catalyst is designated as DPMSAA-0.45NW-1.5×2C.

J. Preparation of DPMSAA Resin with 0.238 Equivalents Alkylation

Another mercaptosulfonic acid polymer is prepared from 1.5 percent crosslinked styrene/divinylbenzene co-polymer beads (−30+70 mesh) using a variation of the procedure described in Example 32. The alkylation and sulfonation reactions are performed in one step utilizing chlorosulfonic acid as the alkylation catalyst and sulfonation reagent.

Styrene/divinylbenzene co-polymer resin beads (10.00 g, −30+70 mesh, 1.5% divinylbenzene, approximately 96.0 mmol styrene repeat units) are added to a round bottom glass flask (reactor) under a pad of plant nitrogen with a sodium hydroxide scrubber attached (to trap evolved HCl). A solution of (2-bromoethyl)benzyl chloride (mixture of aromatic ring isomers, predominately para) (5.32 g, 0.238 equivalents based upon styrene repeat units) in 1,2-dichloroethane (25 mL) is added to the dry resin beads. The beads are allowed to swell for approximately 5–10 minutes, then additional 1,2-dichloroethane (35 mL) is added to the swollen beads. The slurry is cooled 2–3° C. in an ice bath, then chlorosulfonic acid (12.0 mL, approximately 21.0 g, 1.5 equivalents based upon total equivalents of phenyl groups in the mixture) is added slowly dropwise over approximately 1 hour 45 minutes. The mixture is allowed to stir an additional 1 hour at 3–4° C., then is removed to room temperature and allowed to react an additional 1.5 hours. The mixture is then cooled in an ice water bath and water is slowly added to quench the excess chlorosulfonic acid. Thereafter the beads are isolated according to the procedure described in part C of Example 32. Likewise, the thiolation reaction is as in part D of Example 32 using thiolacetic acid and sodium bicarbonate (3.0 equivalents of each reagent relative to the estimated maximum amount of bromine in the polymer). The final polymer catalyst has a titrated water-wet (water swollen) acid capacity of 0.94 milliequivalent/mL catalyst. The final polymer catalyst is designated as DPMSAA-2S-0.25–1.5×2C.

K. Preparation of DPMSAA Resin Having 6.5 percent Crosslinking

Another mercaptosulfonic acid polymer is prepared from 6.5 percent crosslinked styrene/divinylbenzene co-polymer beads (380 micron uniform particle size spheres) using the procedure described in steps B–D of Example 32, except using 0.427 equivalents of (2-bromoethyl)benzyl chloride in the alkylation reaction. Chlorosulfonic acid (1.5 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The mass yield of polymer obtained from the alkylation reaction corresponds to a 57 percent yield in the alkylation reaction and a degree of functionality of 0.24. The final polymer catalyst has a titrated water-wet (water swollen) acid capacity of 1.75 milliequivalent/mL catalyst. The final polymer catalyst is designated as DPMSAA-0.45–6.5×2C.

L. Preparation of DPMSAA Resin with 0.25 Equivalents Alkylation and Having 1.8% Crosslinking Another mercaptosulfonic acid polymer is prepared from 1.8% crosslinked styrene/divinylbenzene co-polymer beads (−25+40 mesh) using the procedure described in steps B–D of Example 32, except using 0.25 equivalents of (2-bromoethyl)benzyl chloride in the alkylation reaction. Chlorosulfonic acid (1.5 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The mass yield of polymer obtained from the alkylation reaction corresponds to an 86% yield in the alkylation reaction and a degree of functionality of 0.22. The final polymer catalyst has a titrated water-wet (water swollen) acid capacity of 0.85 milliequivalent/mL catalyst. The final polymer catalyst is designated as DPMSAA-0.25–1.8×2C.

M. Preparation of DPMSAA Resin with 0.10 Equivalents Alkylation and Having 1.8% Crosslinking Another mercaptosulfonic acid polymer is prepared from 1.8% crosslinked styrene/divinylbenzene co-polymer beads (−25+40 mesh) using the procedure described in steps B–D of Example 32, except using 0.10 equivalents of (2-bromoethyl)benzyl chloride in the alkylation reaction. Chlorosulfonic acid (1.5 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The final polymer catalyst has a titrated water-wet (water swollen) acid capacity of 0.81 milliequivalent/mL catalyst. The final polymer catalyst is designated as DPMSAA-0.10–1.8×2C.

N. Preparation of 1.5% Crosslinked DPMSAA Resin with 0.10 Equivalents Alkylation and Using Sodium Hydrosulfide in the Thiolation Reaction Another mercaptosulfonic acid polymer is prepared from 1.5% crosslinked styrene/divinylbenzene co-polymer beads (−30+70 mesh) using a variation of the procedure described in steps B–D of Example 32, except using 0.10 equivalents of (2-bromoethyl)benzyl chloride in the alkylation reaction and sodium hydrosulfide in the thiolation reaction. Chlorosulfonic acid (1.5 equivalents relative to the calculated total equivalents of phenyl groups in the polymer) is used in the sulfonation reaction. Sodium hydrosulfide (6.4 equivalents relative to the calculated amount of bromine in the polymer) is used in the thiolation reaction. The mass yield of polymer obtained from the alkylation reaction corresponds to a degree of functionality of 0.10. The final polymer catalyst has a titrated water-wet (water swollen) acid capacity of 0.82 milliequivalent/mL catalyst. The final polymer catalyst is designated as DPMSAA-AT-0.10–1.5×2C.

O. Preparation of DPMSAA Resin with 0.25 Equivalents Alkylation and Having 4% Crosslinking Another mercaptosulfonic acid polymer is prepared from 4% crosslinked styrene/divinylbenzene co-polymer beads (360 micron uniform particle size spheres) using the procedure described in steps B–D of Example 32, except using 0.25 equivalents of (2-bromoethyl)benzyl chloride in the alkylation reaction. Chlorosulfonic acid (1.5 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The mass yield of polymer obtained from the alkylation reaction corresponds to a 73% yield in the alkylation reaction and a degree of functionality of 0.18. The final polymer catalyst is designated as DPMSAA-0.25–4×2C.

P. Preparation of DPMSAA Resin with 0.10 Equivalents Alkylation and Having 4% Crosslinking Another mercaptosulfonic acid polymer is prepared from 4% crosslinked styrene/divinylbenzene co-polymer beads (360 micron uniform particle size spheres) using the procedure described in steps B–D of Example 32, except using 0.10 equivalents of (2-bromoethyl)benzyl chloride in the alkylation reaction. Chlorosulfonic acid (1.5 equivalents relative to the calculated total equivalents of phenyl groups in the polymer) is used in the sulfonation reaction. Thiolacetic acid and sodium bicarbonate (3.0 equivalents of each reagent relative to the calculated amount of bromine in the polymer) are used in the thiolation reaction. The mass yield of polymer obtained from the alkylation reaction corresponds to an 74% yield in the alkylation reaction and a degree of functionality of 0.074. The final polymer catalyst is designated as DPMSAA-0.10–4×2C.

EXAMPLE 33

Evaluation of Catalysts in a Continuous Process

A three-stage up-flow reactor is constructed from three vertical stainless steel tubes with sampling ports between each section. Each reactor stage is water jacketed for temperature control with all connecting lines heat-traced to prevent reactor line plugging. Likewise the 2L reactor feed tank is jacketed so that precise control of the reactor feed can be obtained. From the feed tank, feed flows through an electrically heat-traced section of tubing for control of feed input temperature.

Each reactor section is packed with 10–20 mL of water-wet catalyst.

The reactor feed consists of a solution of 4 weight percent acetone in phenol. The acetone:phenol mixture is precisely metered into the temperature controlled reactor system at a defined combination of flow rate (1.0 mL/min to 2.0 mL/min) and reactor temperature (55° C. to 65° C.). Upon.start-up of each new loading of catalyst, the feed passes through the catalyst for at least 12 hours before measurements are recorded to remove water from the catalyst. Product composition of the reactor effluent from each of the three stages is analyzed by HPLC while gas chromatography is used to analyze for acetone and water. The results obtained from tests of the catalysts at various times of reaction (reactor residence times) are provided in Table XIX. Productivity is expressed in terms of pounds of bisphenol A produced per hour per cubic foot of water-swollen catalyst charged into the reactor. (NOTE: Unless otherwise noted, all of the catalyst results are obtained at 55° C.)

TABLE XIX

| CATALYST | Res. Time | Acetone Conv.(%) | Prod. lb/hr/ft3 | op/pp (%) | tris/pp (%) | Cyclics/pp (%) | tot imp/pp (%) |
|---|---|---|---|---|---|---|---|
| 65 CDOWEX 50Wx4, 25% Prom. | 10 | 61.47% | 18.03 | 2.524% | 0.702% | 0.535% | 5.393% |
| | 20 | 77.69% | 11.53 | 2.722% | 0.648% | 0.472% | 5.204% |
| | 30 | 84.52% | 8.34 | 2.826% | 0.628% | 0.455% | 5.149% |
| 55 CDOWEX 50Wx4, 25% Prom. | 10 | 49.28% | 13.83 | 1.983% | 0.783% | 0.328% | 5.297% |
| | 20 | 66.16% | 9.51 | 2.102% | 0.675% | 0.292% | 4.862% |
| | 30 | 73.02% | 7.06 | 2.163% | 0.692% | 0.257% | 4.838% |
| DPMSA-MER3C | 5 | 84.28% | 49.76 | 1.479% | 0.549% | 0.879% | 5.053% |
| | 10 | 97.63% | 29.92 | 1.456% | 0.491% | 0.828% | 3.829% |
| | 15 | 100.00% | 20.62 | 1.449% | 0.553% | 0.836% | 3.831% |
| DPMSA-1.5X3C | 7.5 | 46.34% | 18.12 | 1.884% | 0.855% | 0.929% | 5.803% |
| | 15 | 71.71% | 14.51 | 1.769% | 0.794% | 0.890% | 4.359% |
| | 22.5 | 81.41% | 11.21 | 1.733% | 0.730% | 0.819% | 4.951% |
| DPMSA-1.5X2C | 7.5 | 44.74% | 16.13 | 1.577% | 0.958% | 1.524% | 7.512% |
| | 15 | 74.84% | 14.31 | 1.537% | 0.800% | 1.298% | 4.840% |
| | 22.5 | 88.14% | 11.53 | 1.534% | 0.790% | 1.167% | 5.372% |
| DPMSA-6/42-3C | 7.5 | 11.34% | 3.08 | 2.519% | 0.000% | 2.096% | 12.918% |
| | 15 | 29.62% | 4.38 | 2.203% | 0.383% | 2.044% | 15.295% |
| | 22.5 | 52.79% | 6.12 | 1.946% | 0.296% | 1.999% | 12.032% |
| DPMSA-6.5X3C | 7.5 | 1.68% | 0.13 | 0.000% | 3.029% | 0.000% | 1.290% |
| | 15 | 1.11% | 0.05 | 0.000% | 2.166% | 0.000% | 2.166% |
| | 22.5 | 0.34% | 0.10 | 0.524% | 0.687% | 0.000% | 0.671% |
| DPMSAA-0.75-1.5X2C (0.75 funct.) | 7.5 | 90.84% | 34.65 | 1.583% | 0.992% | 0.570% | 4.298% |
| | 15 | 98.43% | 20.02 | 1.596% | 0.912% | 0.513% | 3.707% |
| | 22.5 | 100.00% | 13.30 | 1.521% | 0.922% | 0.677% | 3.478% |

TABLE XIX-continued

| CATALYST | Res. Time | Acetone Conv.(%) | Prod. lb/hr/ft3 | op/pp (%) | tris/pp (%) | Cyclics/pp (%) | tot imp/pp (%) |
|---|---|---|---|---|---|---|---|
| DPMSAA-0.75-1.5X2C (2ML) | 3.75 | 66.83% | 51.95 | 1.571% | 0.886% | 0.687% | 5.074% |
|  | 7.5 | 89.68% | 35.41 | 1.590% | 0.975% | 0.565% | 4.400% |
|  | 11.25 | 94.95% | 25.26 | 1.617% | 0.945% | 0.528% | 4.142% |
| DPMSAA-0.45-1.5X2C | 7.5 | 88.41% | 35.33 | 1.500% | 0.948% | 0.454% | 3.972% |
|  | 15 | 96.92% | 20.14 | 1.615% | 0.896% | 0.381% | 3.481% |
|  | 22.5 | 100.00% | 13.61 | 1.807% | 0.894% | 0.416% | 3.549% |
| DPMSAA-0.45-1.5X2C (2 ML) | 3.75 | 62.82% | 51.50 | 1.533% | 1.030% | 0.523% | 4.535% |
|  | 7.5 | 87.35% | 35.25 | 1.542% | 0.942% | 0.448% | 4.101% |
|  | 11.25 | 94.30% | 25.66 | 1.571% | 0.915% | 0.414% | 3.793% |
| DPMSAA-0.45/0.30-1.5X2C (2 ML) | 2.5 | 57.60% | 66.41 | 1.480% | 0.902% | 0.709% | 4.875% |
|  | 5 | 77.51% | 44.63 | 1.530% | 0.883% | 0.683% | 4.540% |
|  | 7.5 | 87.41% | 34.38 | 1.520% | 0.846% | 0.600% | 4.208% |
| DPMSAA-0.45NW-1.5X2C (2 ML) | 3.75 | 63.00% | 54.30 | 1.501% | 0.824% | 0.693% | 4.538% |
|  | 7.5 | 84.20% | 36.13 | 1.531% | 0.808% | 0.610% | 4.034% |
|  | 11.25 | 93.44% | 26.46 | 1.578% | 0.802% | 0.539% | 3.707% |
| DPMSAA-0.25-1.5X2C (2 ML) | 3.75 | 67.68% | 52.61 | 1.565% | 0.952% | 0.399% | 4.190% |
|  | 7.5 | 85.79% | 33.77 | 1.552% | 0.873% | 0.405% | 3.725% |
|  | 11.25 | 92.42% | 24.34 | 1.623% | 0.862% | 0.412% | 3.601% |
| DPMSAA-0.10-1.5X2C (2 mL) | 3.75 | 59.7% | 50.28 | 1.666% | 0.828% | 0.267% | 3.790% |
|  | 7.5 | 77.5% | 32.51 | 1.660% | 0.801% | 0.330% | 3.580% |
|  | 11.25 | 85.64% | 24.05 | 1.670% | 0.777% | 0.315% | 3.440% |

Note: "2 ML" means flow was 2 ml/min - otherwise flow is 1 ml/min
% is percent
conv. is conversion
prod. is product Bisphenol A
op/pp is the ratio of ortho, para bisphenol to para, parabisphenol tris is higher oligomeric adduct derived from the reaction of 2 acetone molecules with 3 phenol molecules
cyclics are by-products having dianins, spirobiindanols, and dihydroindanols.
tot. imp. is total impurities including ortho, para bishenol A, tris, cyclics as well as other unidentified product peaks.

We claim:

1. A catalytically-active material comprising an insoluble organic or inorganic support in which is incorporated a polystyrene resin having a mercaptosulfonic acid residue represented by the formula

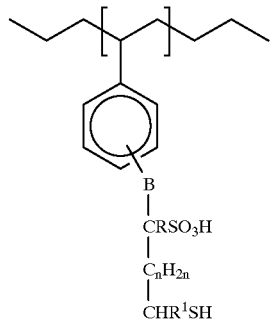

wherein B is a straight or branched chain alkylene bridging group, R and $R^1$ are independently selected from H, alkyl or aryl, $—C_nH_{2n}—$ is straight or branched chain alkylene and n is an integer from 0 to 20.

2. The catalytically-active material of claim 1, wherein B is $CH_2$ and $—C_nH_{2n}—$ is $—CH_2CH_2—$ or $—CH_2—$.

* * * * *